(12) United States Patent
Kagan

(10) Patent No.: US 9,650,427 B2
(45) Date of Patent: May 16, 2017

(54) MODULATORS OF ANTIVIRAL SIGNALING PATHWAYS AND THERAPEUTIC USES THEREOF

(75) Inventor: Jonathan C. Kagan, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/234,305

(22) PCT Filed: Jul. 23, 2012

(86) PCT No.: PCT/US2012/047838
§ 371 (c)(1),
(2), (4) Date: Oct. 6, 2014

(87) PCT Pub. No.: WO2013/016278
PCT Pub. Date: Jan. 31, 2013

(65) Prior Publication Data
US 2015/0037362 A1    Feb. 5, 2015

Related U.S. Application Data

(60) Provisional application No. 61/510,927, filed on Jul. 22, 2011.

(51) Int. Cl.
*A61K 38/00* (2006.01)
*C07K 14/705* (2006.01)
*C07K 14/47* (2006.01)
*A61K 39/00* (2006.01)

(52) U.S. Cl.
CPC ........ *C07K 14/705* (2013.01); *C07K 14/4702* (2013.01); *C07K 14/4703* (2013.01); *A61K 38/00* (2013.01); *A61K 39/00* (2013.01)

(58) Field of Classification Search
None
See application file for complete search history.

(56) References Cited

U.S. PATENT DOCUMENTS 7,625,724 B2 * 12/2009 Chen .................. A01K 67/0276
                                                                435/91.1
2008/0003614 A1    1/2008 Chen et al.

OTHER PUBLICATIONS

Lad et al., "Identification of MAVS splicing variants that interfere with RIGI/MAVS pathway signaling", Molecular Immunology, vol. 45, pp. 2277-2287 (2008).
Moore et al., "NLRX1 is a regulator of mitochondrial antiviral immunity", Nature, vol. 451, pp. 573-577 (2008).
Castanier et al., "Mitochondrial dynamics regulate the RIG-I-like receptor antiviral pathway", EMBO Reports, vol. 11, No. 2, pp. 133-138 (2010).

* cited by examiner

*Primary Examiner* — Thomas S Heard
(74) *Attorney, Agent, or Firm* — Mintz Levin Cohn Ferris Glovsky and Popeo, P.C.; Peter F. Corless; Christopher R. Cowles

(57) ABSTRACT

The invention provides methods, compositions, and kits featuring novel RIG-I like receptor activators or inhibitors for use in preventing or treating virus infection or autoimmune disease.

19 Claims, 3 Drawing Sheets

US 9,650,427 B2

MODULATORS OF ANTIVIRAL SIGNALING PATHWAYS AND THERAPEUTIC USES THEREOF

RELATED APPLICATIONS

This application is a 35 U.S.C. §371 U.S. national entry of International Application PCT/US2012/047838 (WO 2013/01627) having an International filing date of Jul. 23, 2012, which claims the benefit of U.S. Provisional Application No. 61/510,927, filed Jul. 22, 2011, the entire contents of which are hereby incorporated by reference in its entirety.

GOVERNMENT SUPPORT

This invention was made with Government support under Grant Number A1093589 awarded by the National Institutes of Health. The Government has certain rights in the invention.

BACKGROUND OF THE INVENTION

RIG-I like receptors (RLRs) are a type of intracellular pattern recognition receptor involved in the detection of viruses by the innate immune system. RLRs are critical sentinels of viral infection, surveying the cytosol of all mammalian cell types for the presence of viruses containing RNA genomes. In addition, RLRs play a role in autoimmunity. Factors induced by RLRs are responsible for activating autoreactive T-cells, and as such, RLRs have emerged as important regulators for a growing list of non-infectious immunopathologies resulting from inappropriate host response to self RNA. Thus, depending on the clinical symptoms, some patients will benefit from inhibition of the RLR signaling pathways (e.g., patients with autoimmune disease) whereas others will benefit from activation of these pathways (e.g., patients suffering from RNA viral infection).

Despite a clinical utility for such therapeutic molecules, few RLR specific inhibitors and activators are currently available. Accordingly, there is a need for developing novel RLR specific inhibitors and activators for treating viral infection and autoimmune disorders.

SUMMARY OF THE INVENTION

As described below, the present invention is based upon the discovery of novel RIG-I like receptor (RLR) specific activators and inhibitors. The invention features compositions and kits containing the novel RLR activators or inhibitors. The invention also features methods for using these novel therapeutic molecules to treat a subject having or at risk of viral infection and/or autoimmune disease.

In aspects, the invention provides RLR inhibitors that inhibit the MAVS adaptor protein.

In embodiments, the RLR inhibitor comprises a polypeptide fragment of the MAVS protein (e.g., human MAVS protein). In related embodiments, the polypeptide fragment is a competitive inhibitor or dominant negative of the MAVS protein.

In embodiments, the RLR inhibitor comprises amino acids 10-77, 15-77, 20-77, 25-77, 30-77, 35-77, 40-77, 45-77, 50-77, 10-73, 15-73, 20-73, 25-73, 30-73, 35-73, 40-73, 45-73, and 50-73. In related embodiments, the RLR inhibitor further comprises amino acids from the PRR (any amino acids from 107-173) and/or the TM (any amino acids from 514-535). In some embodiments, the RLR inhibitor comprises amino acids 50-73 of the MAVS protein (GNRDTLWHLFNTLQRRPGWVEYFI; SEQ ID NO: 1).

In aspects, the invention provides RLR activators that activate the MAVS adaptor protein.

In any of the above aspects and embodiments, the RLR inhibitor or activator further contains a targeting moiety. In embodiments, the targeting moiety facilitates delivery of the RLR inhibitor or activator to the cytosol of a cell. In related embodiments, the targeting moiety contains a cell penetrating domain of the *Drosophila* antennapedia protein. The cell penetrating domain can contain amino acids RQIKIWFQNRRMKWKK (SEQ ID NO: 2).

In embodiments, the targeting moiety is TAT or Pep-1.

In any of the above aspects and embodiments, the RLR inhibitor or activator further contains a detectable moiety. Detectable moieties are well known in the art and can be detected by spectroscopic, photochemical, biochemical, immunochemical, physical, or chemical means. Exemplary moieties include, but are not limited to, enzymes, fluorescent molecules, particle labels, electron-dense reagents, radiolabels, biotin, digoxigenin, or a hapten or a protein that has been made detectable.

The RLR inhibitor or activator can be covalently or non-covalently linked to a moiety (e.g., targeting moiety and/or detectable moiety). In embodiments, the RLR inhibitor or activator are covalently linked to the moiety. In related embodiments, the covalent linkage of the moiety is N-terminal to the polypeptide fragment. In related embodiments, the covalent linkage of the moiety is C-terminal to the peptide fragment.

In aspects, the invention provides an RLR inhibitor containing GNRDTLWHLFNTLQRRPGWVEYFI (SEQ ID NO: 1). In embodiments, the RLR inhibitor further comprises RQIKIWFQNRRMKWKK (SEQ ID NO: 2). In related embodiments, the RLR inhibitor is the fusion protein GNRDTLWHLFNTLQRRPGWVEYFI-RQIKIWFQNRRMKWKK (SEQ ID NO: 3).

In any of the above aspects and embodiments, the polypeptide can be an isolated polypeptide.

In aspects, the invention provides isolated polynucleotides encoding any of the inhibitors described herein.

In aspects, the invention provides expression vectors contain the isolated polynucleotides.

In aspects, the invention provides host cells expressing the expression vectors.

In aspects, the invention provides pharmaceutical compositions contain any of the inhibitors described herein. In embodiments, the pharmaceutical compositions contain a pharmaceutically acceptable carrier, diluent, or excipient. In some embodiments, the pharmaceutical compositions contain at least on additional therapeutic agent (e.g., an antiviral agent, an immunosuppressive agent, or an anti-inflammatory).

In aspects, the invention provides methods for inhibiting RLR-induced signaling (e.g., RLR-induced antiviral signaling) in a cell. The methods involve contacting the cell with an inhibitor or a pharmaceutical composition described herein. In embodiments, the methods inhibit the MAVS adaptor protein in the cell.

In embodiments, the cell is in a subject. In related embodiments, the cell is a pancreatic beta cell.

In aspects, the invention provides methods for inhibiting RLR-induced signaling (e.g., RLR-induced antiviral signaling) in a subject. The methods involve administering to the subject an effective amount of an inhibitor or a pharmaceutical composition described herein. In embodiments, the methods inhibit the MAVS adaptor protein in the subject (e.g., a cell in the subject).

In embodiments, the subject has or is at risk of developing a disease or disorder associated with an inappropriate host response to self RNA and/or inappropriate activation of antiviral response. In related embodiments, the disease or disorder is autoimmune disease (e.g., type 1 diabetes).

In aspects, the invention provides methods for treating a subject for a disease or disorder associated with an inappropriate host response to self RNA. The methods involve administering to the subject an effective amount of an inhibitor or a pharmaceutical composition described herein. In embodiments, the methods inhibit RLR-induced signaling in the subject and thereby treat the disease or disorder. In related embodiments, the disease or disorder is autoimmune disease (e.g., type 1 diabetes).

In aspects, the invention provides methods for preventing autoimmune disease in a subject. The methods involve administering to the subject an effective amount of an inhibitor or a pharmaceutical composition described herein. In related embodiments, the autoimmune disease is type 1 diabetes.

In any of the above aspects and embodiments, the subject can be a mammal (e.g., human).

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated herein and constitute a part of this specification, illustrate several embodiments of the invention and, together with the description, serve to explain the principles of the invention.

DEFINITIONS

To facilitate an understanding of the present invention, a number of terms and phrases are defined below.

The terms "RIG-I like receptor" or "RLR" as used herein refer to a family of dsRNA helicase enzymes. There are three members of the RLR family: RIG-I (retinoic acid-inducible gene 1); MDA5 (melanoma differentiation-associated protein 5); and LGP2 (Laboratory of Genetics and Physiology 2; also known as Probable ATP-dependent RNA helicase DHX58 and RIG-1-like receptor 3). These molecules are involved in recognition of viruses by the innate immune system. For example, RIG-I and MDA5 activate MAVS (mitochondrial antiviral-signaling protein; also known as VISA (virus-induced signaling adapter), IPS-1 and Cardif), which triggers antiviral signaling pathways that result in the expression of cytokines, interferons (IFNs) and interferon stimulated genes (ISGs).

The terms "mitochondrial antiviral-signaling protein," "MAVS," "VISA," "virus-induced signaling adapter," "IPS-1," and "Cardif" as used herein refer to an intracellular adaptor protein encoded by the MAVS gene. In embodiments, the terms refer to a polypeptide or fragment thereof having at least 85%, 90%, 95%, 99%, or more amino acid identity to NCBI Accession Nos. Q7Z434, Q7Z434.2, and NP_065797.2.

The exemplary sequence at NCBI Accession No. Q7Z434 is (SEQ ID NO: 4):

```
  1 mpfaedktyk yicrnfsnfc nvdvveilpy lpcltardqd rlratctlsg nrdtlwhlfn
 61 tlqrrpgwve yfiaalrgce lvdladevas vyqsyqprts drppdplepp slpaerpgpp
121 tpaaahsipy nscrekepsy pmpvqetqap espgenseqa lqtlspraip rnpdggples
181 ssdlaalspl tssghqeqdt elgsthtaga tssltpsrgp vspsysfqpl arstprasrl
241 pgptgsvvst gtsfsssspg lasagaaegk qgaesdqaep iicssgaeap anslpskvpt
301 tlmpvntval kvpanpasvs tvpsklptss kppgavpsna ltnpapsklp instragmvp
361 skvptsmvlt kvsastvptd gssrneetpa aptpagatgg ssawldssse nrglgselsk
421 pgvlasqvds pfsgcfedla isastslgmg pchgpeeney ksegtfgihv aenpsiqlle
481 gnpgppadpd ggprpqadrk fgerevpchr pspgalwlqv avtgvlvvtl lvvlyrrrlh
```

The exemplary sequence at NCBI Accession No. Q7Z434.2 is (SEQ ID NO: 5):

```
  1 mpfaedktyk yicrnfsnfc nvdvveilpy lpcltardqd rlratctlsg nrdtlwhlfn
 61 tlqrrpgwve yfiaalrgce lvdladevas vyqsyqprts drppdplepp slpaerpgpp
121 tpaaahsipy nscrekepsy pmpvqetqap espgenseqa lqtlspraip rnpdggples
181 ssdlaalspl tssghqeqdt elgsthtaga tssltpsrgp vspsysfqpl arstprasrl
241 pgptgsvvst gtsfsssspg lasagaaegk qgaesdqaep iicssgaeap anslpskvpt
301 tlmpvntval kvpanpasvs tvpsklptss kppgavpsna ltnpapsklp instragmvp
361 skvptsmvlt kvsastvptd gssrneetpa aptpagatgg ssawldssse nrglgselsk
```

-continued

```
421 pgvlasqvds pfsgcfedla isastslgmg pchgpeeney ksegtfgihv aenpsiqlle 481 gnpgppadpd ggprpqadrk fqerevpchr pspgalwlqv avtgvlvvtl lvvlyrrrlh
```

The exemplary sequence at NCBI Accession No. NP_065797.2 is (SEQ ID NO: 6):

```
  1 mpfaedktyk yicrnfsnfc nvdvveilpy lpcltardqd rlratctlsg nrdtlwhlfn 61 tlqrrpgwve yfiaalrgce lvdladevas vyqsyqprts drppdplepp slpaerpgpp 121 tpaaahsipy nscrekepsy pmpvqetqap espgenseqa lqtlspraip rnpdggples 181 ssdlaalspl tssghqeqdt elgsthtaga tssltpsrgp vspsysfqpl arstprasrl 241 pgptgsvvst gtsfsssspg lasagaaegk qgaesdqaep iicssgaeap anslpskvpt 301 tlmpvntval kvpanpasys tvpsklptss kppgavpsna ltnpapsklp instragmvp 361 skvptsmvlt kvsastvptd gssrneetpa aptpagatgg ssawldssse nrglgselsk 421 pgvlasqvds pfsgcfedla isastslgmg pchgpeeney ksegtfgihv aenpsiqlle 481 gnpgppadpd ggprpqadrk fqerevpchr pspgalwlqv avtgvlvvtl lvvlyrrrlh
```

By "MAVS," "VISA," "IPS-1," "Cardif," and the like are meant a polynucleotide encoding a MAVS polypeptide or fragment thereof (e.g., a polynucleotide encoding the amino acid sequence of NCBI Accession Nos. Q7Z434, Q7Z434.2, and NP_065797.2). An exemplary sequence is provided at NCBI Accession No. NC_000020 (Gene ID: 57506).

The exemplary sequence at NCBI Accession No. NC_000020 is (SEQ ID NO: 7):

```
   1 acatggccaa tggccgcgcg ctctgcccgc cccgcctcct cgctgcggga agggtcctgg 61 gccccgggcg gcggtcgcca ggtctcaggg ccggggtac ccgaggtaag atcgcttccc 121 gggcgttggg tcctttcggc tcagcacgca cggacgcctt tagggaaggt ggctgcagcg 181 gcaggacgga gtccgccggg acgccctggg tctggggtgc gcggggggcc caggagggga 241 caggacgcgc ggggatccgg aagagcgggc cctgtcgcaa gagtttcggg aacactgagg 301 gctccaggcg ccgcatccag catccgggga aaaggggta ggtggcgctg ggcgtctgct 361 caggctgggg gaaaggtagg gccagaaggg gacgggcagc ggccgctgac ctcctcctgc 421 cgcccgcggg cccagggtga cgctaaggtg gggccgagcc tcgaccgggt gcgcctagag 481 gtcgagtgct gccgccctcc gctgggtctg gacagttctc ggcggcgaca ccagctcaaa 541 acggcctccc cgccctccgc ggacctgggt cgcgcccagg aatccgatcc aaggctgtga 601 ggcctgtccc tttgggaagg gtgggtgttt atttccggga tgcactcaga gcctctggac 661 agtcaggtcg gaaactttgc tgtattggga acactctgtc acctacttcc ttctcagttg 721 ggaaggaagt gccaagaaaa catgaaacaa accaaaaaca cgaaaaaggg attctctgta 781 tggaagccgt gaagcctcaa aaatatctag gaggacagcc agcgacctgg gacctgtggc 841 agccatgtga aagcagggtt aatgtctgga ctaaatgttg cttccaccta agtgcaccct 901 cagcctccct cccgccaagt gaccttgggt cctctttggg cttgaaggca ggtggctgtg 961 tgggtctcgc tgcaggggtc tctgtgccct gcaaggtgta tgaccagttg cagtgaggca 1021 gcaggttttg ggttcaaatc ctgtgctagc ctctggccag ctgtgcacct tggcaacact 1081 ttccctgtca cgggattggg gaaggattaa ctgaaagaac cttaggatgt gcctgtctac 1141 aatgggccct ccataaatgt gaacaaatgt gggcttcctt tccttttgtt tgggccacat 1201 catcccttcc cctccatctg tggctgaagc tggaatgcag aagagtgcct catctgactg 1261 ccttctggta cctggctgat gccatgagaa aggaaggaga aaggggtctt tttttttttg 1321 aaatggagtc tcactctctt gcccaggctg gagcgcagtg gtccaatctt ggctcactgc
```

-continued

```
1381  aacctctgcc tcctgggtct agagattctc ctgcctcagc ctcctgagta gctgggacta
1441  caggtgtgtg ccaccatgcc tggctaattt ttgcattttt agtagagacg gggtttcacc
1501  atgttggcca ggctggtctc aaactcctga cctcaagtga tctgcctgcc tcggcctccc
1561  aaagtgctgg gattccaggc gtgagccacc gcgcccggcc gagaaaggga tctattaact
1621  cccatagagt tgttctttgc taatttcttg aaggctcaga ggaccccgc ctcaccttcc
1681  tgattctcct gacctgtcat tagtacttgc cccacgagga atgtagcagg gcctgctggc
1741  tggcaaagca actcatgcat gtgaggctct gaggccagtg acaggactgc ttcccctgtg
1801  aggaaggtct ggtggcccaa cagcttttag gtgctgtctg ctctacagca ctgcctcctg
1861  agagaggtct catgcctgcc tgatgcccac ttggtcctct cctgcctcct ccctccctg
1921  acaacccact tggaatccaa tagcatctca aacttcactt gttccgaact gagttctgga
1981  gtcccttctg agccactgct cctcccctgg cttctctggc ctggtaaaag ggcaccttcc
2041  atccacccag tgcccaagga gtcatgcttc ttttctctcc cttatctcct acaccctcaa
2101  aacaccagga atctggctgc ctcctgccat ctctgtggtt cccatcctga ccatagtcat
2161  cctgtctcct gggctgtggc ctccttactg gtctcccagt tttcatcctg gcccctccaa
2221  agtcctcaca accaccagag aagtctttaa tgtaaatcag atcctcttct ttccctgccg
2281  gaaccttcca gtggttccct gtttcactcc aactaaaacc cagagtcctt cctacagca
2341  ctctacatga gtggccctg ccacctcctt gaccttgaca atctctgccc cttccctag
2401  cttgcttgct tttttttttt ttttcctat gatggagttt tgatcttgtc acccaggctg
2461  gagtgcaatg ggatgatttc agctcactgc aacctctgcc tcctgggttc aagcgattct
2521  cctgcctcag cctcccgagt agctgggatt acaggcgccc accaccatgc taattttgt
2581  attttagta gagaaagggt ttcaccatgt tggcgaggct ggtctcaacc tcctgagctc
2641  aggtgatcca cccgcctagg cctcccaaag tgctgggatt ataggcgtga gtcacgcagc
2701  cagccatccc tagctttctt gacctagacc acactgacct gctttctatt cttcaaacat
2761  gccaagctca ttcttgtttt aggactttg catttaccat gctctctgcc taaaacacca
2821  atcttctcag agcctgagaa cagctcagct gtgttctgca cgctagttca gaaaggcttc
2881  tttgaccccc tagttcaagt agcatgcctg tctccagggg ctctgtctca ttacctgctt
2941  tactttcttt agagccttta ttgctatctg gaactcttat ttgggtatta atttactgat
3001  ctgttatttg tcccacccca ttagaatata aattggatgt ggcatagacc ttgtctcttt
3061  tattccctgc agcactccct gatgggggcg gcagaaaagt aacgagcaaa tacatctata
3121  actgcaaatt gtggtaactc ctacataaac aactggcagc aattgcttat atttgaggca
3181  cttaaaaatt tttaagctgg ctgggcgcgg tggctcatgc ctgtaatccc agcactttgg
3241  gaggccgagg cgggcagatc acgaggtcag gagatcgaga ccatcctggc taacacggtg
3301  aaacctgtct ctactaaaaa tacaaaaaat tagccgagcg tggtagcagg cgcctgtagt
3361  cccagctact tgggaggctg aggcaggaga atggtgtgaa cccgggaggc ggagcttgca
3421  gtgagccgag attgcaccac tgcactccag cctgggtgaa ggagcgagac tgtctcaaaa
3481  aaaaaaaaaa aaaaaaaaa agaaattttt ttaagctgct gggcgcggtg gctcacgcct
3541  gtaaatctca gcactttggg aggccgaggt gagcggatca cctgaggtcg ggagttcgag
3601  accggaacat ggtgaaaccc tgtctctact aaaaatacaa aattagcggg gcgtggtggc
3661  tcatgcctgt aatcccagct acttgggagg ctgaggcagg agaatcgctt gaacccagga
3721  ggcagaggtt gcagtgagcc gagatcgcgc cattgtactc cagcctgggc aaaaagagtg
```

-continued

```
3781  aactccattt caaaaaaaaa aaaaaaggcc aggcgcagtg gctcacgcct gtaatcccag
3841  cactttggga ggccgaggca ggcggatcac gagttcagga gattgagacc atcctggcta
3901  acacggtgaa accctatctc tactaaaaat acaaaaaatt agccgggtgt ggtggcgggc
3961  gcctgtggtc ccagctactc gggaggctga ggcaggagaa tggtgtgaac caggaggtg
4021  gagcttgcag tgagccgaga ttgcaccaca gcactccagc tttggtgaca gagcgaaact
4081  ccgtctcaaa aaaaaaaaa aaaaaatttt aagcttagag gccggccaca gtggctcagc
4141  actgtgcagg ccaaggcaag aggatcactt gaggtcaaga gttcgagacc agcctggcca
4201  acatggtgaa accctgtctc tactaaaaaa tacaaaaatt ggccaggcgc gttggctggc
4261  gcctgtaatc ctagcaactt gggagaccaa ggcaggcaga tcacctgggg tcaggagttc
4321  aggaccggcc tggccaacat taaaacatat aaaaacccgt ctctactaaa aatataaaaa
4381  ttatccaggc atggtggcgt gtacccgtaa tcccagctac tcgggaggct gaggtaggag
4441  aattgcttaa acccgagaag cagaggttgc agtgaaccga gattacgcca ctgcactcca
4501  gcctgggcaa cagagcgaga ctctttctca aaaacaacaa caacaacaaa caaacaaatt
4561  agccaggcat gatggtgggc acgtgtaatc ccagctactc gggaggctga ggcaggagaa
4621  ttgcttgaat gtgggagatg gaggctgcag tgagccgaga tcacaccact gcactccagc
4681  ctgggcgaca gggagactct gtctcaaaaa aaaaaaaaa aaaaaagtt tataaggctg
4741  aattaccgta ctgtcaaaac aagctgctat ctgagccgtt ttaagggtga ggaagtctgg
4801  aaactgataa cttgcccagg acacacagtg agttcaaggc atggaactca gtctcctatc
4861  ttaagaatgt atgtgggccg ggcatggtgg ctcacgcctg taatcccagc gctttgggag
4921  gccaaggcag gcagatcatc tgaggtcagg agttcaagac cagcctgacc aacatggaga
4981  aaccctgtct ctactaaaaa tacaaaaatta accaggtgtg gtggtgcatg tctgtaattc
5041  cagctactca ggaggctgag gcagaagaat cacttgaacc cggaaggcag aggttgcgat
5101  gagccgagat tgtgccattg tactccagcc tgggcaacaa gagtctgaa ctctgtctca
5161  aaaaagaaaa aaagaatgta tgtgtagcag gcttttttt tttttttttc ccccgagacg
5221  gaatctggct ctgtcgccca ggctggagtg cagtggcgca atcttggctc actgcaagct
5281  ccgcctccca ggttcacgcc attctcctgc ctcagcctcc cgagtagctg ggactacagg
5341  caccgccag tacgccgggc taatttttg tatttttagt agagacgggg tttcaccgtg
5401  ttagccagga tggtcttgat ctcctgacct cgtgatccac ccgcctcggc ctcccaaagt
5461  gctgggatta caggcgtgag ccaccgtgcc cggcctatgt gtagcaggct ttaatggtgg
5521  gcctgcagcc atgtcatgga agaagctga cctgaagatc tcagttcttt cttcttctac
5581  taactagcaa gcatacctca gtttcttctt taaagcggga tgatccgatt attatcatgt
5641  tggggttcac tttttatttt ttcagtgtgt cccaaagcag cagcacgttt aggtatagcc
5701  ctcttgctat cagcttgagg gccttagagc caggaaggga gccaggacat ttataggcac
5761  agaaactagg gtcacataca gatcccccca ccgcatgtgc tagggtaca tgcagacctt
5821  cccagtgctg accaacctgc agagaagaaa tgggccctag gtattctgga tctgattctt
5881  tttggtcttc aattattttt atttttattt ttttagagac agggtctcgc tgtgttgccc
5941  aggctggcct cgaacagctg ggctcaagcg atcctcctgc cctagcttct tgagtagctg
6001  gtggtcatca attcattttt agcaaattct gcagaatttt ttttttttt ttttttttg
6061  agacggagtc tcactctgcc gcccaggctg gagtgcagtg gcgtgatctc ggctcactac
6121  aacctccgcc tcttgggttc aagcaattct ctgtctcagc ttcctgaata gctgggactg
6181  caggcgcccg ccaccatgct tggctaattt ttttgtattt tcagtagaga cggggtttca
```

-continued

```
6241  ccatcttggc caagttggta ttgaactcct gacctcgtga tccatccgcc tcggcctccc
6301  aacgtgctgg ggttacaggc gtgagccacc gcgcccgggt tctgcaggaa ttttggagag
6361  actcaggcag taataaaata ggatgtttac agaaattaaa gatggcggcc gggcgcggtg
6421  gctcacgcct gtaatcccag cactttggga ggccgaggcg ggcgcatcac gaggtcagta
6481  aatcgagacc atcctggcta accccgtgaa accccgtctc tactaaaata caaaaaaatt
6541  agccgggcgt ggtggcgggc gcctgtcgtc ccagctactc aggaggctga ggcaggagaa
6601  tggcgtgaac ccgagaggcg gagcttgcag tgagccgaga tcgcgccacc gcactccagc
6661  ctgggcgaca gagaaagact ccgtctcaaa aaaaaaaaa agaaattaaa ggtggctgga
6721  cacattggct ggtgcttgtc atccgagcta cttgacaggc ggaggcaggg ggatcgcttg
6781  aggccaggcg tttgagacca gcctgggcag catcatgaga ccctgtctct agaaaaaata
6841  aaaaaattag ctgggcatag tggcgcaggt ttgtagttcc agctaccggg gatgctgagg
6901  cgggaggatt gcttgagccc acgagttcga ggctgcagtg aactattatt gcaccactgc
6961  acccaacttg ggtgacagag accccatctg tttgtttgtt tgttttgag acagagtttc
7021  gctcttgttg cccaggctgg agtgcaatgg tgcaatcttg gctcaccgca acctctgccc
7081  ccaggttcaa gcaattctcc tgcctcaacc tcccgagtag ctgggattac aggcatgcgc
7141  caccatgccc agctattttt tttttttttt tgtatttttta gtagagacgg gattttctcc
7201  atgttggtca gtctggtctc caactcccga cctcagttaa tcccccaaat tggcctccca
7261  aagtgctggg attataggcg tgaaccactg tgcccagccc gagacccccat ctcttaaaaa
7321  caaaataaaa caaaacaaaa acggccaggt gtggtggctc acacctgtaa tccccaaact
7381  tgggaggccg aggcgggtgg accacttgag gtcaggagtc tgtgaccagc ttgccaacat
7441  ggtgaaaccc catctctact aaaaatacaa aaattagctg gcatggtgg tgcgcacctg
7501  taatcccagc tactcagaag ggaggctgag gcaagagact caattgaacc caggaggcgg
7561  aggttgcagt gagccgagat tgccccactg cactccagcc tgggtgacaa agtgagactc
7621  gctctcaaaa aaaaaaaaaa gaagaaatta aagatgaaag aaaacaaaca ttccaaaaag
7681  ttgagaaaga attgcctttt gtccagcccc actcccaacc ccccaaccct gttgtaatgt
7741  gtgatctgtt ttcttccagt ctcgtttcct ctcagtccat ccaccttca tggggccaga
7801  gccctctctc cagaatctga gcagcaatgc cgtttgctga agacaagacc tataagtata
7861  tctgccgcaa tttcagcaat ttttgcaatg tggatgttgt agagattctg ccttacctgc
7921  cctgcctcac agcaagagac caggtgagca agggaagtga cagcccgaca ctggcctggg
7981  ggcagggctg tggaattcaa agctcagccc catcctagtt cctcacccaa gctgggctg
8041  gctccttcct tcttcctctt gctgtgtctt gctccttgtc cttgctgctt tcttttttt
8101  tttttttttt tgagattgag tctcgttctg tcgccaggct ggagtgcagt ggcacgatct
8161  tggctcattg caacctccgc ctcctgggtt caagtgattc tcctgcctca gcctcctgag
8221  tagctgggat tacaggtgcg tgccaccacg cccagctaat ttttttgttt ttaatagaga
8281  cggggtttca ccatgttggc caggatggtc ttgatctctt gaccttgtga tccgcctgcc
8341  tcggcctccc aaagtgctgg gattacaggc gtgagccacc gcacccttgc tgcttttcta
8401  acttttggat ggagtgtggc tcagggtggc gttgctgact tcgccgagct ccccccttgtg
8461  ttgcttttgt gcactgctca aaaatatggc gctggctctc tgagatttcc tggctctggt
8521  ccacttgccc acttttttg gaacctccta tttccttcat ctctcttgcc cttccttgtc
8581  ctgctcagtt ttgattccat tctccttgtc atggggccct gtcctggcac ggagctggga
```

```
                                                 -continued
 8641  ctcaggtttg agagctggca ggatcagggt cgctctagcc ccaacagaac ttgctgcagg 8701  cccctggcac tcactagctg gtgaaacggg cacaacccct cccgttgta gctgctgttc 8761  tcagattgga cccctgtgct ccagagggta cctgttggct cttttgggc tcctgtcct 8821  cagatttctc aggagcccca ttgttgtctc cgctgtcctc ccacacagat cgcattagta 8881  tgcaggtctg tttggagttt gctcctccct cttgtatttt ggggtttata gggatatctt 8941  gttttatagt aaatattttc tgtgggtttt ctttatttc tttaaaaaat ttttttttga 9001  gacggagtct cgctgtgttg cccaggctgc agtgcaatgg catgatctca gctcactgca 9061  acctctgcct cctgggttca agtgattctc gcgcctcagc ctcctgagta gctggggtta 9121  caggcgcatg ccaccacacc tggctgattt tgtatttgta gtagagatgg agtttcacca 9181  tgttggccag gctggtcttt attttattt ttgagacaga gtcttgctct gtcactcagg 9241  ctggagtgca gtggcacgat ttttttttt ttttgagacg gagtctcact ctgtcgccca 9301  ggctggagtg cagtggtgtg atctcggctc actgcaagct ctgcctcctg ggttcacgcc 9361  attctcctgc ctcagcctct tgagtagatg ggactacagg cgcctgccac catgcccggc 9421  taattttttg tatttttaat agagacgggg tttcactgtg ttagccagga ttgtctcgat 9481  ctcctgacct catgatccac ccgcctcggc ctcccaaagt gctgggatta caggcgtgag 9541  ccactgcgcc cagcattttt ttttttttt ttttgagat ggagtctcgc tgtgtcttcc 9601  aggctggagt tgcagtggtg ccatcttggg tcaacctctg cctcctgggt tcaagcaatt 9661  ctcctgcttc agcctcctga gtagctggga ttacaggtat atgctaccac acccggctaa 9721  tttttgtgtt tttagtagag acggactttc accatgttgg tcaggctggt cttgaactcc 9781  tgaccttgtg atcctcggcc ttccaaagtg ctgggattac gggtgtgagc taccgcacct 9841  ggctattttc cttttctaa aaatctagct cctgcaggat tctgtgggtt tttgtttctg 9901  ctgtctggtt gcttgttttt atgtgagaat tcaggtagac ataaaaactc tagggctggg 9961  cacggtggct cacgcctgta atcccagcgc tttgggaggc caaggcgggt ggatcacctg 10021  aggtcaggag ttcgagacca gcctggccaa catggcgaaa ccatgtctct actaaaaata 10081  caaaaaaatt agccgggtgt ggtggtgggc tcctgtaatc ccagctactc gggaggctga 10141  ggcaggagaa tcgcttgaac tcaggaggca gaggttgcag taagctgata tcacggcact 10201  gcactccagc ctgggcgacg gagtgggact ccgtctgaaa aaaaaaaaa aaaagaaac 10261  aaaaaaactc tgcagccact gtcatctgcc cacaatctcc ccagcattct cagcttcctt 10321  gtttgttatt gtcggccccc tctctttccg tcttttgccc cttcatcat acttttgcta 10381  tctaccttt ccttctctcc taatccaaac ctttcttttt gccctggggg ccatattaat 10441  ccaaggcttt tgtatcagat taactgggtt tggattcctg ccccactgtt ttaggatctt 10501  tgctacagta ctttgcttct gctaagcctc agtttcctca ttagtaaagt ggagataata 10561  atggcattaa ataaagatga tacatgcaaa gcccttaatg gagagcccag acatagtta 10621  attccagtt tccggcagct gcctttattg atgtggctgc taattgctct tcctcactcc 10681  atacctggcc ctgtcctggg ctccgatcca gtttcacgtg gctgccttgc ccttgtggct 10741  ttcttggcac ccctcccccc gctgtggctt cattctgggt ggggaagtgg caggggccac 10801  ctggcttgag caggacagtg gcattgtgtc ttccaggatc gactgcggc cacctgcaca 10861  ctctcaggga accggacac cctctggcat ctcttcaata cccttcagcg gcggcccggc 10921  tgggtggagt acttcattgc ggcactgagg ggctgtgagc tagttgatct cgcggacgaa 10981  gtgcctctg tctaccagag ctaccagcct cgtgagcgtc ctgcccttgc cctcctggac 11041  ccccagcctg ctccctggcc tccgctctcc ttttctctct ccctgtactt cctgcctttc
```

-continued

```
11101  tctgtcatcc tctttcttgt cactgtgaag cgatgaataa acctgggtgt agatccaggc
11161  tgagccactt accagctgtg tcccttggc caagtccctt aatttccctg agcctcaggc
11221  ctctcttctg taaaatgaag ctcatggcag catctgccgc ggggagctgc agtgggtgat
11281  actgcgggac gatgcgtgtt gagtattgag ctgggctggg cacttcctgt atgcccagca
11341  catggagtct cccctaactt tcacggctgt agcattcgcc tcccacctt cctcatttct
11401  tctcccccac ctactcattc accctccctc tcctcctt ctcttccct cccctggttt
11461  accctgagag ccttcgacgc cctctatcag ctgcccagtt attctttaag tccctctcag
11521  tgtccctgcc actctgagtg ctcggaggcg atttgatgag attgagtttg atcctgagtg
11581  agatcaagac atgggaggag gctgggcgcg gtgtttcaca cctgtaatcc cagcactttg
11641  ggaggccgag gcaggcggat catgaggtca ggagatggag accaccctgg ctaaaacagt
11701  gaaaccccgt ctctactaaa aatacagaaa attagccggg catgttgtcc cagctactca
11761  ggaggccgag gcaggagaat cacttgaacc agggaggcag aggttgcagt gagctgagat
11821  cgcgccactg cactccagcc tgggcgacag agtgggattc catctcaaaa aaaaaaaaa
11881  aaagacatgg gaaaaaaat caagccagcc ctatttatat ttcaaactag aggtaacccc
11941  cgagaccctg gtcacattta tagctgtggg acatccatgt ttttcttttc tttctctctc
12001  ttttttttt ttcctttag agacagagtc ttgctgcgcc acccaggctg cagtgcagtg
12061  gtgcaatcat agctcactgc agccttgacc tcctggactc aagtgatcct tctacctcag
12121  cctccagagt agctgggact acaggcatgg acaactacac ctggctaatt tttaaatttt
12181  ttgtagagat gacatctcac tatgttgccc aggctggtct caaactcctg gctgaagcg
12241  atcggcctcc cagagtgctg ggatcatagg tgtgagccac cgcgtctggc tctcatgctt
12301  gcttttctct ccttttttccc ttccttgctt ttcctccctc cctccctccc ttcctctctt
12361  ccttccttttt tttccttcct tcttttttaaa tatgtctctt catgtgtgga gattaatagt
12421  gatccctggc tgggcacggt ggctcacgcc tgtaatccca gcactttggg aggccgaggc
12481  gggcggatca aaggtcagg agttcgagac cagcctggcc aatatggtga aaccctgtct
12541  gtaccaaaaa tacaaaaaaa ttagctgcgc atggtggtgc aagcctgtaa tcccagctac
12601  ttgggaggct gaggcaggag aattgcttga accggggagg tggaggttgc agtgagccga
12661  gattgcgcca ctgcactcca gcctggatga cagagtgaga ctccgtctcc aaaaaaaaa
12721  aacccaaaaa tagtgatccc ctgaatacaa tggctgtggt agggcctgat gaggggtggg
12781  ggcaaagggg aggggctcag gtggcagcat cagggcaggg gtcagtgagc aatgatagtc
12841  atgtggagga gaaagccact gggtcctagg atgcctgggg acagagaaga gtgactgctg
12901  acacggcgtg ggtgactaga gaccacgag gcccccccat actcccttc ctcccttgct
12961  accttgtcct ccatctgctc tcaccctccc actcctgccc ccttgccaag tgatgcttgt
13021  cactcctttt tttttgaaa tggagtttcg ctctgtcgcc caggctggag tgcagtggtg
13081  ccatctcagc tcactgcaag ctccgcctcc cgggttcacg ccattcctct gcctcagcct
13141  cccgagtagc tgggactaca ggcgcctgca accatgcccg gctaactttt tgtattttt
13201  agtagagatg gggtttcacc gtgttagcca ggatggtctc gatctcctga cctcgtgatc
13261  cacccgcctc ggcctcccaa agtgctggga ttacaggcgt gagccaccaa gcccagccct
13321  gcttgtcact cttgaggagt gggcccacat cagaacagct tttggaccta tgggtggggc
13381  gggggtgta cccaagagca cccaagcctc tttaatcatg aggagaaccc ccaattcctt
13441  ttttttgag acagagtctt gctcagtcgc ccaggctgga gtgcagtggc atgacttcgg
```

-continued

```
13501  ctcaccacaa cctctgcctc ccggggttcaa gtggttctcc ttcctcagcc tccctatagt
13561  ccctgattcc ttctattttt tttttttttt tttgagacgg agtctcgctc ttgttgccca
13621  ggctggagtg caatggtgca atctcaggtc atggcaacct tcacttccca ggttcaagca
13681  attctcctgc ctcagcctct cgagtagctg ggattacagg catgcgcctc cacgcctggc
13741  taattttgtt attttagta gagacagggt ttctccatgt tggtcaggct ggtctcgaac
13801  tcacgacctc aggtgatcca cccacttcgg cctcccaaag tgctgggatt acaggcgtga
13861  gccaccacgt ctggcttctt tttctttttt tcccccgaga cggagtcttg ctctgttgcc
13921  caggctggag tgcagtggcg cgatctcagc tcactgcaac ctccgtctcc caggttcaag
13981  caattcttct gcctcagcct cctgagtagc tgggattaca ggtgcttgcc agcacgcctg
14041  gctaatttt gtattttag tagagacggg gtttcactat gttggccagg ctggtcttga
14101  actcctgacc tcctaatcca cctgccttgg cctccccaaa tcctgggatt acaggcatga
14161  gccatcgtgc ccagcccctg attccttctt tttttttctt tcttttttt tttagacgga
14221  gtctcgctct gtcgcccagg ctggagtgca gtggcgcgat cttggcttac tgcaagctcc
14281  gcctcccggg ttcacgccat tctcctgcct cagcctcctg agtagctggg actacagggg
14341  cccgccacca tgcccggcta ataataatgt tgtatttta gtagagatgg gttttcactg
14401  tgttagccag ggtggtctcg atctgacctc gtgatctgcc tgccttggcc tcccaaagtg
14461  ctgagattac aggcatgagc cactgtgccc agccctgatt ccttcttgat atcactacat
14521  ctttgtcctc tagggacctc ggaccgtccc ccagacccac tggagccacc gtcacttcct
14581  gctgagaggc cagggccccc cacacctgct gcggcccaca gcatcccta caacagctgc
14641  agagagaagg agccaagtta ccccatgcct gtccaggaga cccaggcgcc agagtcccca
14701  ggagaggtct gtcctcatag tctaccttga gccaccactt ttgtgttcct atctgcccac
14761  ttctgcccat tgagccttcc agaaaccctc tcccgtcccc tataaatcac gcctaatctc
14821  tgctcagaac cctagggctt cctcagtggg gatctgcccc agaccagctt ccaggctgct
14881  gaccaggtct tcaccctgtg gcagccctaa tcctctgtca gcaaccagct gggagaccac
14941  agttttgtgt gtgtgtgtgt gtgtgtgt gacagtgtct cattctgtca cccaggctgg
15001  agtgcagtgg agtgatcttg gctcactgca acctctgcct cctgggttca ggtcattctc
15061  ctgcctcagc ctcctgagta gctgggatta caggcaccca ccaccacgcc cagctaattt
15121  ttgtatttt agtagagatg gggttttgcc gtgtcagcca ggctggtctc gaactcctga
15181  cctcaggtga tctgcccacc tttgcctccc aaagtgctgg gattacaggc gtgagccacc
15241  gcacctggca atgctgtgtg ttttctgtga ggtagacgta aggacacctg tggacagagg
15301  gtctgggaat taccagaacc caggcaaggg ctcccctggc tcctgtgctc catggtgtgg
15361  gctgaggcct ataggagatg ccccaagagc acaagctgcc ctttgtgagc tcttgggaga
15421  ggcaactgcc ttattcatat tttccctcat tgcagaattc agagcaagcc ctgcagacgc
15481  tcagccccag agccatccca aggaatccag atggtggccc cctggagtcc tcctctgacc
15541  tggcagccct cagccctctg acctccagcg ggcatcagga gcaggacaca gaactgggca
15601  gtacccacac agcaggtatg catggaatct ggaattatag ggtccttctg atctctcaag
15661  tgagggtaag aattagagtt gccccatctg gcttccttga acaggagaca aggtgggaat
15721  aaagggagtt caaccccagga agcaaaccag ttccttagtg ggtgtatcag ttagcatttg
15781  ctgtgtaaca aatagtccac tccagttttc caaatttttt ttttagtagc ttaaaataca
15841  gccatttatt tagcatatga tcctgtgggt caggcatttg ggctacctac atgggcattt
15901  cttctggtct tggctgaatt tcctctcaag tactcaccgg tatatacata agttctgcct
```

-continued

```
15961  ctggctgttt gctgagcacc ttggttctct tctatgtagt ctctcatcct ccagcacaca
16021  aacccatcat ggcagctggg cagagttctc agagagggct caaaactggc acagtgtccc
16081  ctgtgctcca ttctgtgggc aaaagcaagt tataaggcca gcctagattc aaggagtagg
16141  gaaatagact ccctccctag acgggaggac tgacaggcac agtgcagtgg ggctgggtgg
16201  agatgagcga gataagtagg gccatttttg cgctctgcca aagggactgt agggaacagc
16261  cagggcctat agggcagtgg gagagggaca gtgaagggct gcatcagctg ttggcagggg
16321  aacctttagg cactgtctta ccgcagagat ctccagttcc cagtgaatca tgaaaacttc
16381  tcagtcccca gaggaagtaa ggtcttcatc atccagtggc ctggactcaa ctccagatgt
16441  cagtgctccc cctcagaaat atatagttgt ccatctggac ctctcaggcc agcatgtctc
16501  tttcctactt cccaaactat tccacatgac gctggtgccc agtcagccct cagtgccctg
16561  ggacagccac aagacacatg agcagttaga ggctgggaga cgtcatctta gtacttttgt
16621  catccccaaa ctgctccaag cacctgtctg ctttgcagtg tcacctggcc acgggatgcc
16681  tttcaggagt tgctgtagac cacagaggca gagggcgctt aggtttcagt acgtttgtag
16741  acacaggtcc catgagattc tgtggtatta gattgtggtg ggggagctgt acatcagaat
16801  caccctgact tttgccagct gtggggcttg gcatgtgcat tccgagttcc gtggagagtc
16861  ctgctgcaac tgcctttaca gaccatcacc acctgctatc ctctgcttcc cccacccagg
16921  tcaggcagcc tcccaggggt ggctttgtcc ttgtcccctc tcttcccaag cctccgggat
16981  ggccaggcct ctcggctggt gtgagctgtt ctgcatgagc catcctgcca cccccttgccc
17041  tgatccatgg ctgctcccac tcatggtggt aggagaggga cagcagtggg ggaagtgtcc
17101  aggattgcat gaggctaagg tcaaagtaga aaaggtagac acaggagagg ggaggtttcc
17161  caggtgggag aggaaaaagc ggagagaata attaataatg gtcttcaggc tcctaggtac
17221  catttcactg tgtgccagga cagacctggg gctacaggtc aaggactgag ggcagctgtt
17281  gggctttcag gccaggaagc agtgaccaaa gggactgtgg catcctcctcc aagggcagga
17341  gatttggagg cctagacaca gtagggacca tgagatctgg gccagaggga cccttctcca
17401  ggcctcaagg taatggtctt tgggtctgtg tttccacttg tgttttttcca ccggcaggtg
17461  cgacctccag cctcacacca tcccgtgggc ctgtgtctcc atctgtctcc ttccagcccc
17521  tggcccgttc cacccccagg gcaagccgct tgcctggacc cacagggtca gttgtatcta
17581  ctggcacctc cttctcctcc tcatcccctg gcttggcctc tgcaggggct gcagagggta
17641  aacagggtgc agagagtgac caggccgagc ctatcatctg ctccagtggg cagaggcac
17701  ctgccaactc tctgccctcc aaagtgccta ccaccttgat gcctgtgaac acagtggccc
17761  tgaaagtgcc tgccaaccca gcatctgtca gcacagtgcc ctccaagttg ccaactagct
17821  caaagccccc tggtgcagtg ccttctaatg cgctcaccaa tccagcacca tccaaattgc
17881  ccatcaactc aacccgtgct ggcatggtgc catccaaagt gcctactagc atggtgctca
17941  ccaaggtgtc tgccagcaca gtccccactg acgggagcag cagaaatgag gtgagtcctc
18001  gcccttcctg gcagggatcc tggccccttc ccccgggaca gcttgcccac ctggccctgg
18061  ccttggcccc ttcccagtct gcattctgtg tccagcctgt gctgctctgt ggcctctcct
18121  tgagggcata cagacagttg agaaccagcc tcatgcaggc cccacaccat gttctccagg
18181  aggaacagtc attgagcttc taagtctgga caccctcagga gggtcagcca cagggggcac
18241  ccactggtca ggtgtataag ttcatttagg gctcgtagtt cctagtgaag ccgagcggtg
18301  ccgttttgca cataaggaag cagtgacggg gacagcacag tggcccatct gcctcttgcc
```

-continued

```
18361  ttgctcttca ccaggatgcc tggtgtgtcc ctccatggcc aggctttaca gaacgcagtc
18421  ccacctggag cagccactcg gacccagcag cccccccattg ttgcctgctc caagcctcac
18481  atctaaccct agctgcggct gtctgctggg aagagccaag tccatagggc cctttgggca
18541  catggccagg cctctgaccc tgtggctgct ctctagttct caggcccagg caggatgtca
18601  gtgcaggatg gagccccgcc ctaccaaagg cttccaggtg ggcatgagct cacaggcagg
18661  ccagggagta gggaaaggct gccctggagg aggccaccat tggtgcagat tcttggtccc
18721  ctctacccccc actgctccaa gaaaaggtgg cctagggggca ttatagattg ggaattgagg
18781  ggttggagtg ttagttcatg ccctggcctg ggaatgggac cgccctacca ggttcgtctc
18841  cctgccaacc ccagtccctt ccagtgctct cctttctttc ccaggagacc ccagcagctc
18901  caacacccgc cggcgccact ggaggcagct cagcctggct agacagcagc tctgagaata
18961  ggggccttgg gtcggagctg agtaagcctg gcgtgctggc atcccaggta gacagcccgt
19021  tctcgggctg cttcgaggat cttgccatca gtgccagcac ctccttgggc atggggccct
19081  gccatggccc agaggagaat gagtataagt ccgagggcac ctttgggatc cacgtggctg
19141  agaaccccag catccagctc ctggagggca accctgggcc acctgcggac ccggatggcg
19201  gccccaggcc acaagccgac cggaagttcc aggagaggga ggtgccatgc cacaggccct
19261  cacctggggc tctgtggctc caggtggctg tgacaggggt gctggtagtc acactcctgg
19321  tggtgctgta ccggcggcgt ctgcactagt gaagccctgg gctcttccca ccacccatct
19381  gttccgttcc tgcagtacac ctggcccctc tccgaagccc cttgtccctt tcttggggat
19441  tgtggaggct gggtcagagg ggagttaagg gactgcaggc ctggcagcag gacatgcctt
19501  ggctgaacca gtcctgaga gcagcatctc tgtccccacg gtgccttgtg tgggtccccg
19561  tccttggctt tctgggtcct gggctgcccc cagtgctcca gaccttccccc actggcaatc
19621  caggttatca tccatgtcct ccagaggagc ttcctcctcc aggcctcagc cctgttggcc
19681  caggtggagc aggagggacc actggaacat gtggtgcttg ggaatgcctc tcctgttgca
19741  ttggtccctg aaggcctcag ggcaggtatg tggtgtgtgg gcgactccac aagacctgcc
19801  tcccatcctg gcagcccagc ctgagaccgt tgcattgagg caggcaggag cggcagggtg
19861  gctgctctcc aggagcccaa ctgccttgag ttcctgcccc actgggcccc ctcccctgct
19921  gggcaatcct gggaaggtct ggaggttcct gtggacctca gggaagccag gggcagctgt
19981  caggcctgag aagacctgt ggagctcctc tccagcctcc tctttccctc ccctctggtc
20041  tccattctct tcagctccct acatgggctg ggggaggagac acctggtggg cagagctcag
20101  gcagaggttt ggatttcagc tccctcactt ccggggctgt gtggctttgg cagatgtcag
20161  acttctggtc ttgcttctcc acgtggacag tgagtatctg gctcattctt cactgggttc
20221  ttctgagatt gaacctacag gtgtttgcca agtgcctggc ccagagcaag tggccactgc
20281  ttctcccatc tctctcctgc ccaacctggt agagctgagg gcatgagagg cagagtgcac
20341  agtggtcaag ggtgcagctc tgcagcacag gcagcctagg cctgcgtccc aacctgcctc
20401  tcaccagctc tgtgaccttg ggcaagggat ttatctgtct gtcccttagt tttctcacct
20461  gtaaaaggag gataagtata tatatatatt tcccagtgtt gtgaagatta aggagttta
20521  tcgatgtagg tcttaggatg agtcctggca tttaccaagg gttggatata tgttattatc
20581  actattaagt gttgagggtc caggcatgct gggcaacagg gacccccatct ctacaaaaaa
20641  gtttaaaaaa ttagccaggc gtggtggtgc acctgtcgtc ttagctactt gggaggctga
20701  ggtgggagga tcacttgagc ccagaagctt gaagctgcag tgagctagga tcgtgccact
20761  gcactccaac ctgggtgaga gagcgagacc ctgtctcaag aaaaagaaaa atgcagagaa
```

-continued

```
20821  acaggagtct tggctactcc tttagaggca gactcagacc ctcctgcctc acagctttat
20881  ctttgtattt gccccttact ttatcttgtg ccttgagaaa ttgctgggga gagaggtatg
20941  tccactgggc agctgtacag gatggaggat atagggcgtt tccactccca gcagccaggt
21001  tccctcaccc caagctcacc cactgttggg gagattatct acaataacac cagaaacaca
21061  ttggggtgga ttgggggtat ccttatgggt tcttttcagg gaaccattgc tggacaaggc
21121  acaggagcca cctccatttc tgagctctgc aagggacaag aactagagcc atcaggggct
21181  gggctcactg tggccccacc ccaagccgtc agcctccagg gatctacacc ctgccttggc
21241  tgctacagct ttttcactcc actgccctag gggagttcag caacctaatg atctctatct
21301  ctgaacatct cttcatccca tgctccaagt ccagcaacct gcaccctgga accaggagtg
21361  gaccctaccc gagctgtctg tattaatccc catcccccac caccaatctt aaaaagccct
21421  ctgtccccct accctaaacc ccagttaggt acccatgctg ggcaggtcag ttaacaattt
21481  atgcacaggt actagtttta ttgtattacc gttccagggt agctttgaaa aaagtatctc
21541  aaaaaggcaa catgggccga gcgcagtggc tcacgcctgt aatcccagca ctttgggagg
21601  ccaaggtggg cagatcgcct gaggtctgga gttcaagacc agcctggcca cagggtgaa
21661  accccgtctc tacaaaaata agaaaattag ccaggtgtag tggcagacgt ctgtaatccc
21721  agctattcag gaggctgagg cacgagaatt ccatgaaccc aggatgcgga ggttgcagtg
21781  agccgagatt gtgccactgc gctccagcct gggcgacaga gtggtattct gtttcaaaaa
21841  aaaaaaaaaa ggcagtatgt agccccgaag actgttgccc aagtggtaga atgttagcac
21901  actaccagcc taggtaaaaa atacaaaaag taactgggca tggcggcgcc catctatagt
21961  cccagctaca tgggaggctg aggtgggaag ataagtcact tgagcccgcc aggaggcgga
22021  ggttgtagtg agctgagatc gcaccactgc actccagcct gggtgaccga gtgatactct
22081  gtctcaaaga aaaaaaatta taattttagc acagtaacca gccatgatgg gagatacct
22141  gggtaaggca tgtagaaagg gttgagggac cttcccagtc ccctagcccc gcctcccatc
22201  ctcccatctt tttctttttt cttttttta gagaatcacc cagcctggag cgaagtggtg
22261  caatcataac tcactgtatc cttaaactcc cgggcttaag cgatcctcct gcctcagcct
22321  tctgagtaac taggacttca ggtacctgtc accatgcctg gctaattaaa ttttttttc
22381  ttttttttt ttgagatgga gtcttgctct gtcacccagg ctggagtgca gtggcgcgat
22441  ctcagctcac tgcgacctcc acctcctggg ttcaggccat tctcccgcct cagcctccag
22501  agtagctggg actacaggcg cctgccacca cgcctggcta attttttgc acttttagta
22561  gagacggggt ttcactgtgt tagccaggat ggtctcgatc tcctgacctt gtgatccgcc
22621  cgcctcggcc tcccaaagtg ctgggattac aggcgtgagc caccgcgccc agccaaatta
22681  aatttttat agagatgagg tcatgctgtt atgttgccca ggttggcctc atgagatctt
22741  gccttagcct cccaaagtgc tgggattaca gatgtgagac actgcaccca aaccccacca
22801  ctttttttt tccttttct tttttgaga cagtcttact ccgttgccca ggctggagtg
22861  tagtggcatg atctcagctc actgcaacct ccgcctccg ggttcaagca attctcctgc
22921  ctcagcctcc cgagtagctg ggattacaga ggcctgccac cacacccgac taattttcgt
22981  attttagta gagacgggt ttctccatgt tggccaggct gttcttgaac tcctgacctc
23041  aagtgctcca cctgcgttgg cttcccaaag tgctgggata caggagtgag ccactgcgcc
23101  tggctgatcc cagcactttt caaatgatgc cgctcaaagc cgtgacttgg cctactttga
23161  acagcaaact tgttgctgct gttgtcaacc tgaaggcctc tcaaatgcca gcttcaagca
```

-continued

```
23221  gggtgtgaat tggccagtgt cagatctcag gagtcctgtg ttgagagtgt ggctttcagc
23281  tgcggggagc tgcacttggt ggggaaagcc aggcaggtca ccctcacagc cagataatgt
23341  ggaggtcaga acccaaggaa gggagtgaga cctccactcc cagtggggga cctggccacc
23401  catccttggg gacctgagaa agcgtacttc accttggggt gaaggctggg tggggccaga
23461  gggaccagtg ccctcctcag tgcttagggg cagagccacc tgcagcaatg gtatctgcat
23521  attagcccct ctccaccttc tttctcccgc tgaatcattt ccctcaaagc ccaagagctg
23581  tcactgcttc tttctccctg ggaagaatgc gtggactctg cctggtgata gactgaagcc
23641  agaacagtgc cacaccctcg ccttaattcc ttgctaggtg ttctcagatt tatgagactt
23701  cttagtcaaa tatgagggag gttggatgtg gtggcttgtg cctgtaatcc cagcattttg
23761  ggaagccgag gtgggaggat cccttgaagc caggagtttg agacaagcct gggcaacaaa
23821  gcaagaccct atctctaaaa aaaaaaaaaa aaaaaaaaaa aaaaaaaaaa aaaaaaatc
23881  taggagatgc tctttaccct gcctggcctc aaactattaa tagcttcctt tgagcaacat
23941  tatttattat gaactttcaa acacaaaaaa gtagagagag tagaataaca atccccatg
24001  agcccatcac ccaacttcag taattatcaa ttcatggcca tcttgttcac ccctgcctgc
24061  ttccctgctt cccctcattc tgcagaggtt cttttctttt gagacagagt gttgctctgt
24121  tgcccaggct ggagtgcagt ggtgcaactt cggctcactg caacctccgc ctcccaggtt
24181  caagtgattc tcctgcttca gcctctcaag tagctgggat tacagatgcc cgccaccaca
24241  cctggctaat tttcgtattt ttgttagaga tggggtttca ccatgttggc caggctggtc
24301  tcgaactcct gacctcaagt gatccgcccg ccttggcctc ccaaaatgct gggattacag
24361  gtgtgaacca cggtgcctgg ccactgtaca ggttatttat agaagttgga gagtgaaggg
24421  ttgagaaagc caaggggcag atgcgggtct ggaggatttt gtgcctaagg ccctctcttt
24481  gctcccagac agcatgaagt aacaatgagg catccacctc ttggttttgt ggcctctgtg
24541  gatgacgtct ctcaccttga accagttcag agttggagta gcgcaggatc ctgtcttcag
24601  aggaggggcc gaagcgggtt cctctgttgt caagctcttt ggaggtgcct ggctgctact
24661  actgtcccag agaggtgatg atgaatgatg ggtgtgtcca gtggcagttt gccccactga
24721  ggcaggggct tccactaggc cctgacagag cccttccagc aggcagaaat ccctgtgcta
24781  ggcaagattc aaactccgta gcatgtctcc tgctcccatc tcttaggaat ggagtccttc
24841  aggccttgag tcccacattt tccatgatgc tccattaagc agctgatagc accccccacct
24901  ccagggaaag tgagttcaga gtccttggtc taatgcatct gtgttgaaat tgaggccttc
24961  ccctgtgttc acctttctgc tctttttctt ttagcccaag gctatgaagg cctcattcgg
25021  tgctgggcat ggtcactcct agcattcctc actctgttgc taacagcaac agcaataata
25081  ataagggtta caacttactc cataccttac tgtctgccag gcattaagct aagtgcttta
25141  catatattaa gtcatttaat cctcataatg accctatgaa agagatacca tctcaaccca
25201  attgacagct ggtttgcaag attaggaggg atgaaggacc cagggacaa tgcgagggaa
25261  aactctgacc ccggggcccc aggctggatg ttctttatgc ctgtgaacca cagcttatca
25321  catgtctgga gttagggacc ccacttaaag tgagattttg gctggaggtg gtggatcata
25381  cctataatcc cagcactttg ggagaccaag gcagaaggac tgcttgaggc caggagttca
25441  aaaccagtgt aggtaacagc tagaccctat ctctacaaaa aatttaaaaa ttagctgggt
25501  gtggtggtat gtgcctcaag ttccagctac tcaggaggct gaggtgggag gatcacttga
25561  gcacaggagt ttgaagttac agtgagctat gatggcacca ctgcacttca gcctaggcaa
25621  cagagggaga ccctgtcttt aaagtacata gaggttttc acaccaacac atctctgccc
```

-continued

```
25681  agtgtgccaa catctgccac ctgctataat agtactataa cactcaatat gtaattaatg
25741  tagtctcagg gatgttatga caatatgatt acaactatca cgtgtgtgcc cagccaggct
25801  caatgcccca ggctgggcga ggtggggcag gggacacagc ctaaaatgcc aggcctcagg
25861  aagccatttg gtttagcaga cattgtttat taaaggagtt acctatgcca gatcgaaggc
25921  ctaagatgat taagacacta tgagtgcctt caagtggttg gggacgttca tgattgtggt
25981  acagacaaat aggctttcac atcattcttt tatgtaatca tacaacagat atttgcacct
26041  acatgtgcag agcactgtga taggcctcag tgacacagaa taatacggca aagaccccac
26101  ccgatgagcc ccctcccacc acccaccagt acagtagggg gtggtttaat ggagtgttcc
26161  tggaatatga agtgggggca ggcattaggg gtggcaaagg gacaagtgtt tatctgatca
26221  gttatgtact gtttataata agtaaatcag cagagggga ataatactta gaacctatag
26281  agagtaaatc tgacaagatg aaatgctgat gaaaatatgg aggaaatgaa actctcatgg
26341  gttttgcagg gaatctaagt cagtgctgtg ttgtgaatgt aggtgtaccc tttgaattca
26401  tatgttgaat cctaaccccc aaagcaatgg cattaagagg tggggccttt ggggctgggt
26461  atggtggctc atgactgtaa tcccagcact ttgggatgct ggcaggggc agatcacttg
26521  aagccaggag tctgagatca gcctggccaa catggtgaaa ccccatctgt actaaaaata
26581  caaaaattag ccaggtgtga tggcgtacac ctgtaatttc agccactcgg gaggctgaga
26641  caggagaata gcttgaaccc agtaggtgga gatttcagtg agccgagatc gtgccactgc
26701  actccagcct gggtgacaga gcgagactcc atctcaaaaa aataataaag atgtggggcc
26761  tgtgggaggt ggttaggtca tgagggtgga gatcatgaat ggggttagca ccttataaaa
26821  caggcttgag ggagcccttc tgtcccttct accatgtgtg gatgcagtga aaggcaccg
26881  tatctctgaa gcagagagcc cgccctggac actggatctg ctggcacctt gatcttggac
26941  ttcccagcct ctagaactgt gagaaataat ttttgttgt ttacaaatta cccaggctaa
27001  ggtgtttcat tgtaacctga atggaccaag ctggtgtgac cctgttggaa aactggcagt
27061  atctaccaaa agccgaacat acgtataaac tgatccagca gttccactcc tgggtatgta
27121  caccacagaa agctatgtcc accgagacat tggcaagaat gtttctaacc acacgctgac
27181  tgtagcccca aacctgaaac aacccaaatg tccatccacc aacccaaatg tccatccaca
27241  gttgaagcta cagtgaagtc acagggtcga atactactgc acagcaacga atatgaatga
27301  aaatatcgct atgcacagca acatggataa atttcacaga catgaggtca agcaaaagag
27361  gtcagagtcc tcatcatcaa gagagaattc attgtatgat tctcttccta caaaaagtac
27421  agaaataagc aaaactgatc catggtgtta aagccaggg gaacagttaa caggggaggg
27481  atactgggga ggggcatcct ggagtgctgg tctacctcat ctgggtgttg atttcacgag
27541  tattgtcagt ttgtttccag actccctgtt ggagatgtgg aaataaaaac cacctaaaca
27601  agagcagaga ggccatttgg tcaaagtttg caaaggagtc agccatgatt gcttgtattt
27661  ggcagggtc aaaggcaggc agggactgtg aaatgttata gtgaaaaaa agggaaggct
27721  ctgggtgtgc tgtgattgga gattgttggc atgggacag agcggactaa ctggaggggc
27781  atctttggtt ggttgggggg gtatatttgg ctttctctgg ttggtctgga gttggaagag
27841  ggggtgtggt ggctgggat tgggaagaag ctggcagcca ctaagttcag actgttctgg
27901  gtccgattgc tgctgaggct gtggtttggc ttccttggct tcccaggctg gtcatgggtt
27961  tctggccaga gtctattgtc atatgtggcc tggccattgt ccagttgtat gttcagtctc
28021  ttggaaggaa gggtattgac tctgagaggg gccaccatcg ctggaatggg ggacacacag
```

```
-continued
28081  tacttcctcc agctgcctac acccccctag ggtcagtggc gcctgcctgt gagggtgagc 28141  ccaatggcta gagggctctg ctccaagtca ttgcttacta cacccacaaa cattcttcgt 28201  tctttaaggc ctaacttaaa gcccagatcc tacaggaaac cttgattaga cccctctctt 28261  tattaagctt cctaagatca aaccctgctt ttgtgtaaat gctgacctcc ttgcctacat 28321  tttaaaaacc tagagctggg catgatggcc ccagcctgta atcccagtga ttcaggagac 28381  tgaggtggga ggattgctag aagccaggag ttcgagacca gcctgggtaa catagctaga 28441  ccacatctct taaaataaaa tagttaattt agccaggcat gatgatatat gcctgtagtc 28501  ccaactactt ggaaggctga ggtgtgagga tctttgagcc cgggaggtcg aggctacagt 28561  aagctatgat ctcaccactg tactccagcc tgggtgacag agcgagaccc agactcaaaa 28621  aataaaaata aaaaccctga atatcttcct tctacttctt cagtgctgtt tttatttaaa 28681  aaaaaaaaaa accagccaaa accacaactt tttactgaag tgtaatgtaa atgctgtaaa 28741  aggcagtgaa aggcacaagg gaggtggagg ggtaggaagg gtggaagtgg cgggaggaag 28801  tggcagggca ggcaaaatga agggaagccc tgggttcttg tcctgcatcc gcagccagct 28861  cccactttcc tcaccctcca ggacctgtaa actgtgaggc tggaccagtt atgtcaaatc 28921  tgtcctcccc cagagctcag tccctctgcc cttgggtgtc cttggcacaa ggcaggctag 28981  gctgcaccag cttcctccat ctccgtcctg cctcccccat ccccaggtgc cattcccaca 29041  ccatctgaat cactgatttc ctcgcaatca gacgctatct tccagttaat cacttcgctt 29101  gtatttaaca taagaaagaa aaacccttt c attatcacat acagctggaa atcggcttct 29161  tgcaggaggc gtatccaaag gaattggaga agagataaac tggtaattgg tgaaagaatt 29221  actttaattt tttttcctac ttgctgtcat gatgatgtcc ttagaattgt gagcccgtgg 29281  acacttctgt acaataaatc tgctattatt acttctagaa ctaca
```

By "RLR activator," "RLR specific activator," and the like are meant an agent that increases the effects associated with RLR activation (e.g., increase in antiviral activity). The increase in RLR activity is relative to a reference (e.g., an untreated control). Such activation can be by about 10%, 25%, 50%, 75% or more. In embodiments, the agent is a MAVS specific activator and enhances the activity of the MAVS protein. MAVS activity can be enhanced by increasing the strength or the time of an effect of MAVS (e.g., increase expression of anti-viral cytokines, IFNs, and ISGs). In related embodiments, the MAVS specific activator is a polypeptide or fragment thereof. The activator can be covalently or noncovalently linked to a moiety. Exemplary moieties can be any moiety well known in the art, including targeting moieties. A "targeting moiety" is a moiety that is capable of enhancing the ability of an agent to be targeted to, to bind with, or to enter a cell. For example, the targeting moiety can facilitate delivery of the activator into the cytosol of a cell. Exemplary moieties also include detectable labels that will allow tracking of the agent.

By "RLR inhibitor," "RLR specific inhibitor," and the like are meant an agent that decreases the effects associated with RLR activation (e.g., decrease in autoimmune effects). The decrease in RLR activity is relative to a reference (e.g., an untreated control). Such inhibition can be by about 10%, 25%, 50%, 75% or more. In embodiments, the agent is a MAVS specific inhibitor and decreases the activity of the MAVS protein. MAVS activity can be decreased by decreasing the strength or the time of an effect of MAVS (e.g., decrease activation of autoreactive T-cells). In related embodiments, the MAVS specific inhibitor is a polypeptide or fragment thereof. The inhibitor can be covalently or noncovalently linked to a moiety. Exemplary moieties can be any moiety well known in the art, including targeting moieties. The targeting moiety is capable of enhancing the ability of an agent to be targeted to, to bind with, or to enter a cell. For example, the targeting moiety can facilitate delivery of the inhibitor into the cytosol of a cell. Exemplary moieties also include detectable labels that will allow tracking of the agent.

As used herein, the singular forms "a", "an", and "the" include plural forms unless the context clearly dictates otherwise. Thus, for example, reference to "an RLR inhibitor" includes reference to more than one RLR inhibitor.

Unless specifically stated or obvious from context, as used herein, the term "or" is understood to be inclusive.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "activate" is meant an increase in activity, level, or other measurable parameter relative to a reference (i.e., an untreated control). Such activation can be by about 10%, 25%, 50%, 75% or more.

"Administering" is defined herein as a means of providing an agent or a composition containing the agent to a subject in a manner that results in the agent being inside the subject's body. Such an administration can be by any route including, without limitation, oral, transdermal (e.g., vagina, rectum, oral mucosa), by injection (e.g., subcutaneous, intravenous, parenterally, intraperitoneally, intrathecal), or by inhalation (e.g., oral or nasal). Pharmaceutical preparations are, of course, given by forms suitable for each administration route.

By "agent" is meant any small molecule chemical compound, antibody, nucleic acid molecule, or polypeptide, or fragments thereof.

By "analog" is meant a molecule that is not identical, but has analogous functional or structural features. For example, an amide, ester, carbamate, carbonate, ureide, or phosphate analog of an RLR activator or inhibitor is a molecule that either: 1) does not destroy the biological activity of the RLR activator or inhibitor and confers upon that RLR activator or inhibitor advantageous properties in vivo, such as uptake, duration of action, or onset of action; or 2) is itself biologically inactive but is converted in vivo to a biologically active compound. Analogs include prodrug forms of an RLR activator or inhibitor. Such a prodrug is any compound that when administered to a biological system generates the RLR activator or inhibitor as a result of spontaneous chemical reaction(s), enzyme catalyzed chemical reaction(s), and/or metabolic chemical reaction(s).

By "control" is meant a standard or reference condition.

The term "derivative" means a pharmaceutically active compound with equivalent or near equivalent physiological functionality to a given agent (e.g., an RLR activator or inhibitor). As used herein, the term "derivative" includes any pharmaceutically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antivirally active metabolite or residue thereof.

By "disease" is meant any condition or disorder that damages or interferes with the normal function of a cell, tissue, or organ.

By "enhances" or "increases" is meant a positive alteration of at least about 10%, 25%, 50%, 75%, or 100% relative to a reference.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "inhibit" is meant a reduction in activity, level, or other measurable parameter relative to a reference (i.e., an untreated control). Such inhibition need not be complete, but can be by about 10%, 25%, 50%, 75% or more.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In embodiments, the preparation is at least 75%, at least 90%, or at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, HPLC analysis, and the like.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of an RLR activator or inhibitor recited herein is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the RLR activators and inhibitors provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

As used herein, the terms "prevent," "preventing," "prevention," "prophylactic treatment," and the like, refer to reducing the probability of developing a disease or condition in a subject, who does not have, but is at risk of or susceptible to developing a disease or condition.

By "reduces" is meant a negative alteration of at least about 10%, 25%, 50%, 75%, or 100% relative to a reference.

By "reference" is meant a standard or control condition.

As used herein, the terms "treat," treating," "treatment," and the like refer to reducing or ameliorating a disorder and/or symptoms associated therewith. By "ameliorate" is meant decrease, suppress, attenuate, diminish, arrest, or stabilize the development or progression of a disease. It will be appreciated that, although not precluded, treating a disorder or condition does not require that the disorder, condition or symptoms associated therewith be completely eliminated.

The term "therapeutic effect" refers to some extent of relief of one or more of the symptoms of a disorder or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., $ED_{50}$) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

Typically a therapeutically effective dosage should produce a serum concentration of compound of from about 0.1 ng/ml to about 50-100 μg/ml. The pharmaceutical compositions typically should provide a dosage of from about 0.001 mg to about 2000 mg of compound per kilogram of body weight per day. For example, dosages for systemic administration to a human patient can range from 1-10 μg/kg, 20-80 μg/kg, 5-50 μg/kg, 75-150 μg/kg, 100-500 μg/kg, 250-750 μg/kg, 500-1000 μg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

The phrase "combination therapy" embraces the administration of an RLR activator or inhibitor and a second therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days, or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention comprises an RLR activator or inhibitor and at least one additional therapeutic agent (e.g., an antiviral agent, an immunosuppressive agent, an anti-inflammatory, and the like) at the same or different times or they can be formulated as a single, co-formulated pharmaceutical composition comprising the two compounds. As another example, a combination of the present invention (e.g., an RLR activator or inhibitor and at least one additional therapeutic agent) is formulated as separate pharmaceutical compositions that can be administered at the same or different time. Sequential or substantially simultaneous administration of each therapeutic agent can be effected by any appropriate route including, but not limited to, oral routes, intravenous routes, intramuscular routes, and direct absorption through mucous membrane tissues (e.g., nasal, mouth, vaginal, and rectal). The therapeutic agents can be administered by the same route or by different routes. For example, one component of a particular combination may be administered by intravenous injection while the other component(s) of the combination may be administered orally. The components may be administered in any therapeutically effective sequence.

The phrase "combination" embraces groups of compounds or non-drug therapies useful as part of a combination therapy.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

Figure 1:
FIG. 1 is a schematic showing a novel RLR/MAVS signaling inhibitor. A peptide corresponding to amino acids 50-73 of MAVS (GNRDTLWHLFNTLQRRPGWVEYFI; SEQ ID NO: 1) was synthesized in frame with the cell penetrating domain of the antennapedia protein (RQIKIW- FQNRRMKWKK; SEQ ID NO: 2), forming fusion peptide GNRDTLWHLFNTLQRRPGWVEYFI-RQIKIWFQN-RRMKWKK (SEQ ID NO: 3). The underlined amino acid is the threonine that is necessary for MAVS signaling.

The invention is based, at least in part, on the discovery of novel RIG-I like receptor (RLR) specific activators and inhibitors. The invention features compositions and kits containing the novel RLR activators or inhibitor. The invention also features methods for using these novel therapeutic molecules to treat a subject having or at risk of viral infection and/or autoimmune disease.

RIG-I Like Receptors

RIG-I like receptors (RLRs) are a family of pattern recognition receptors that are responsible for detecting viral pathogens. RLRs detect pathogen-associated molecular pattern (PAMP) motifs present on viral antigens and initiate a cascade of events that activates the innate immune response. There are three members of the RLR family: RIG-I (retinoic acid-inducible gene 1); MDA5 (melanoma differentiation-associated protein 5); and LGP2 (Laboratory of Genetics and Physiology 2). RIG-I, MDA5, and LGP2 each share a common functional RNA helicase domain near the C terminus (HELICc) that specifically binds to RNA molecules with viral origin. However, two caspase activation and recruitment domains (CARDs) are present at the N terminal region of RIG-I and MDA5, but not LGP2, which trigger the host interferon response via activation of interferon regulatory factor 3 and NFκB.

RIG-I and MDA5 are expressed in all mammalian cells (e.g., immune and nonimmune cells) and provide the only known comprehensive immune-surveillance network operating to detect viral infections. Upon activation (e.g., detection of viral nucleic acids), RIG-I and MDA5 recruit specific intracellular adaptor proteins to initiate signaling pathways that lead to the synthesis of immunomodulatory molecules that are important for eliminating viruses (e.g., cytokines, interferons (IFNs), interferon stimulated genes (ISGs), and the like). One such adaptor protein is mitochondrial antiviral-signaling protein (MAVS).

MAVS is a predicted 57 kDa protein consisting of three functional domains—a single N-terminal CARD domain (10-77 aa), a medial proline-rich region (PRR; 107-173 aa) and a C-terminal transmembrane domain (TM; 514-535 aa) that anchors it to the limiting membranes of mitochondria and peroxisomes. Full MAVS nucleotide and polypeptide sequences, and variants related thereto, are well known in the art. An exemplary nucleotide sequence can be found at NCBI Accession No. NC_000020 (SEQ ID NO: 7):

```
   1   acatggccaa tggccgcgcg ctctgcccgc cccgcctcct cgctgcggga agggtcctgg
  61   gccccgggcg gcggtcgcca ggtctcaggg ccggggtac  ccgaggtaag atcgcttccc
 121   gggcgttggg tcctttcggc tcagcacgca cggacgcctt tagggaaggt ggctgcagcg
 181   gcaggacgga gtccgccggg acgccctggg tctggggtgc gcgggggggcc caggagggga
 241   caggacgcgc ggggatccgg aagagcgggc cctgtcgcaa gagtttcggg aacactgagg
 301   gctccaggcg ccgcatccag catccgggga aaaggggggta ggtggcgctg ggcgtctgct
 361   caggctgggg gaaaggtagg gccagaaggg gacgggcagc ggccgctgac ctcctcctgc
 421   cgcccgcggg cccagggtga cgctaaggtg gggccgagcc tcgaccgggt gcgcctagag
 481   gtcgagtgct gccgccctcc gctgggtctg gacagttctc ggcggcgaca ccagctcaaa
 541   acggcctccc cgccctccgc ggacctgggt cgcgcccagg aatccgatcc aaggctgtga
 601   ggcctgtccc tttgggaagg gtgggtgttt atttccggga tgcactcaga gcctctggac
 661   agtcaggtcg gaaactttgc tgtattggga acactctgtc acctacttcc ttctcagttg
 721   ggaaggaagt gccaagaaaa catgaaacaa accaaaaaca cgaaaaaggg attctctgta
 781   tggaagccgt gaagcctcaa aaatatctag gaggacagcc agcgacctgg gacctgtggc
 841   agccatgtga aagcagggtt aatgtctgga ctaaatgttg cttccaccta agtgcaccct
 901   cagcctccct cccgccaagt gaccttgggt cctctttggg cttgaaggca ggtggctgtg
 961   tgggtctcgc tgcaggggtc tctgtgccct gcaaggtgta tgaccagttg cagtgaggca
1021   gcaggttttg ggttcaaatc ctgtgctagc ctctggccag ctgtgcacct tggcaacact
1081   ttccctgtca cgggattggg gaaggattaa ctgaaagaac cttaggatgt gcctgtctac
1141   aatgggccct ccataaatgt gaacaaatgt gggcttcctt tcctttttgtt tgggccacat
```

```
1201  catcccttcc cctccatctg tggctgaagc tggaatgcag aagagtgcct catctgactg
1261  ccttctggta cctggctgat gccatgagaa aggaaggaga aagggggtctt ttttttttg
1321  aaatggagtc tcactctctt gcccaggctg gagcgcagtg gtccaatctt ggctcactgc
1381  aacctctgcc tcctgggtct agagattctc ctgcctcagc ctcctgagta gctgggacta
1441  caggtgtgtg ccaccatgcc tggctaattt ttgcattttt agtagagacg gggtttcacc
1501  atgttggcca ggctggtctc aaactcctga cctcaagtga tctgcctgcc tcggcctccc
1561  aaagtgctgg gattccaggc gtgagccacc gcgcccggcc gagaaaggga tctattaact
1621  cccatagagt tgttctttgc taatttcttg aaggctcaga ggaccccgc ctcaccttcc
1681  tgattctcct gacctgtcat tagtacttgc cccacgagga atgtagcagg gcctgctggc
1741  tggcaaagca actcatgcat gtgaggctct gaggccagtg acaggactgc ttcccctgtg
1801  aggaaggtct ggtggcccaa cagcttttag gtgctgtctg ctctacagca ctgcctcctg
1861  agagaggtct catgcctgcc tgatgcccac ttggtcctct cctgcctcct tccctccctg
1921  acaacccact tggaatccaa tagcatctca aacttcactt gttccgaact gagttctgga
1981  gtcccttctg agccactgct cctcccctgg cttctctggc tggtaaaag ggcaccttcc
2041  atccacccag tgcccaagga gtcatgcttc ttttctctcc cttatctcct acaccctcaa
2101  aacaccagga atctggctgc ctcctgccat ctctgtggtt cccatcctga ccatagtcat
2161  cctgtctcct gggctgtggc ctccttactg gtctcccagt tttcatcctg gcccctccaa
2221  agtcctcaca accaccagag aagtctttaa tgtaaatcag atcctcttct ttccctgccg
2281  gaaccttcca gtggttccct gtttcactcc aactaaaacc cagagtcctt cctacagca
2341  ctctacatga gtggcccctg ccacctcctt gaccttgaca atctctgccc cttccctag
2401  cttgcttgct ttttttttt ttttcctat gatggagttt tgatcttgtc acccaggctg
2461  gagtgcaatg ggatgatttc agctcactgc aacctctgcc tcctgggttc aagcgattct
2521  cctgcctcag cctcccgagt agctgggatt acaggcgccc accaccatgc taatttttgt
2581  attttagta gagaaagggt ttcaccatgt tggcgaggct ggtctcaacc tcctgagctc
2641  aggtgatcca cccgcctagg cctcccaaag tgctgggatt ataggcgtga gtcacgcagc
2701  cagccatccc tagctttctt gacctagacc acactgacct gctttctatt cttcaaacat
2761  gccaagctca ttcttgtttt aggacttttg catttaccat gctctctgcc taaaacacca
2821  atcttctcag agcctgagaa cagctcagct gtgttctgca cgctagttca gaaaggcttc
2881  tttgaccccc tagttcaagt agcatgcctg tctccagggg ctctgtctca ttacctgctt
2941  tactttcttt agagcccttta ttgctatctg gaactcttat ttgggtatta atttactgat
3001  ctgttatttg tcccacccca ttagaatata aattggatgt ggcatagacc ttgtctcttt
3061  tattccctgc agcactccct gatgggggcg gcagaaaagt aacgagcaaa tacatctata
3121  actgcaaatt gtggtaactc ctacataaac aactggcagc aattgcttat atttgaggca
3181  cttaaaaatt tttaagctgg ctgggcgcgg tggctcatgc ctgtaatccc agcactttgg
3241  gaggccgagg cgggcagatc acgaggtcag gagatcgaga ccatcctggc taacacggtg
3301  aaaccctgtct ctactaaaaa tacaaaaaat tagccgagcg tggtagcagg cgcctgtagt
3361  cccagctact gggaggctg aggcaggaga atggtgtgaa cccggggagc ggagcttgca
3421  gtgagccgag attgcaccac tgcactccag cctgggtgaa ggagcgagac tgtctcaaaa
3481  aaaaaaaaaa aaaaaaaaaa agaaattttt ttaagctgct gggcgcggtg gctcacgcct
3541  gtaaatctca gcactttggg aggccgaggt gagcggatca cctgaggtcg ggagttcgag
3601  accggaacat ggtgaaaccc tgtctctact aaaaatacaa aattagcggg gcgtggtggc
```

-continued

```
3661  tcatgcctgt aatcccagct acttgggagg ctgaggcagg agaatcgctt gaacccagga
3721  ggcagaggtt gcagtgagcc gagatcgcgc cattgtactc cagcctgggc aaaaagagtg
3781  aactccattt caaaaaaaaa aaaaaaggcc aggcgcagtg gctcacgcct gtaatcccag
3841  cactttggga ggccgaggca ggcggatcac gagttcagga gattgagacc atcctggcta
3901  acacggtgaa accctatctc tactaaaaat acaaaaaatt agccgggtgt ggtggcgggc
3961  gcctgtggtc ccagctactc gggaggctga ggcaggagaa tggtgtgaac caggaggtg
4021  gagcttgcag tgagccgaga ttgcaccaca gcactccagc tttggtgaca gagcgaaact
4081  ccgtctcaaa aaaaaaaaa aaaaaattt aagcttagag gccggccaca gtggctcagc
4141  actgtgcagg ccaaggcaag aggatcactt gaggtcaaga gttcgagacc agcctggcca
4201  acatggtgaa accctgtctc tactaaaaaa tacaaaaatt ggccaggcgc gttggctggc
4261  gcctgtaatc ctagcaactt gggagaccaa ggcaggcaga tcacctgggg tcaggagttc
4321  aggaccggcc tggccaacat taaaacatat aaaaccccgt ctctactaaa aatataaaaa
4381  ttatccaggc atggtggcgt gtacccgtaa tcccagctac tcgggaggct gaggtaggag
4441  aattgcttaa acccgagaag cagaggttgc agtgaaccga gattacgcca ctgcactcca
4501  gcctgggcaa cagagcgaga ctctttctca aaaacaacaa caacaacaaa caaacaaatt
4561  agccaggcat gatggtgggc acgtgtaatc ccagctactc gggaggctga ggcaggagaa
4621  ttgcttgaat gtgggagatg gaggctgcag tgagccgaga tcacaccact gcactccagc
4681  ctgggcgaca gggagactct gtctcaaaaa aaaaaaaaa aaaaaagtt tataaggctg
4741  aattaccgta ctgtcaaaac aagctgctat ctgagccgtt ttaagggtga ggaagtctgg
4801  aaactgataa cttgcccagg acacacagtg agttcaaggc atggaactca gtctcctatc
4861  ttaagaatgt atgtgggccg ggcatggtgg ctcacgcctg taatcccagc gctttgggag
4921  gccaaggcag gcagatcatc tgaggtcagg agttcaagac cagcctgacc aacatggaga
4981  aaccctgtct ctactaaaaa tacaaaatta ccaggtgtg gtggtgcatg tctgtaattc
5041  cagctactca ggaggctgag gcagaagaat cacttgaacc cggaaggcag aggttgcgat
5101  gagccgagat tgtgccattg tactccagcc tgggcaacaa gagtctggaa ctctgtctca
5161  aaaagaaaa aaagaatgta tgtgtagcag cttttttt tttttttttc ccccgagacg
5221  gaatctggct ctgtcgccca ggctggagtg cagtggcgca atcttggctc actgcaagct
5281  ccgcctccca ggttcacgcc attctcctgc ctcagcctcc cgagtagctg ggactacagg
5341  cacccgccag tacgccgggc taatttttg tatttttagt agagacgggg tttcaccgtg
5401  ttagccagga tggtcttgat ctcctgacct cgtgatccac ccgcctcggc ctcccaaagt
5461  gctgggatta caggcgtgag ccaccgtgcc cggcctatgt gtagcaggct ttaatggtgg
5521  gcctgcagcc atgtcatgga aagaagctga cctgaagatc tcagttcttt cttcttctac
5581  taactagcaa gcatacctca gtttcttctt taaagcggga tgatccgatt attatcatgt
5641  tggggttcac tttttatttt ttcagtgtgt cccaaagcag cagcacgttt aggtatagcc
5701  ctcttgctat cagcttgagg gccttagagc caggaaggga gccaggacat ttataggcac
5761  agaaactagg gtcacataca gatcccccca ccgcatgtgc tagggtaca tgcagacctt
5821  cccagtgctg accaacctgc agagaagaaa tgggccctag gtattctgga tctgattctt
5881  tttggtcttc aattattttt atttttattt tttagagac agggtctcgc tgtgttgccc
5941  aggctggcct cgaacagctg ggctcaagcg atcctcctgc ctagcttct tgagtagctg
6001  gtggtcatca attcatttt agcaaattct gcagaatttt tttttttttt tttttttttg
```

```
6061  agacggagtc tcactctgcc gcccaggctg gagtgcagtg gcgtgatctc ggctcactac
6121  aacctccgcc tcttgggttc aagcaattct ctgtctcagc ttcctgaata gctgggactg
6181  caggcgcccg ccaccatgct tggctaattt ttttgtattt tcagtagaga cggggtttca
6241  ccatcttggc caagttggta ttgaactcct gacctcgtga tccatccgcc tcggcctccc
6301  aacgtgctgg ggttacaggc gtgagccacc gcgcccgggt tctgcaggaa ttttggagag
6361  actcaggcag taataaaata ggatgtttac agaaattaaa gatgcggcc gggcgcggtg
6421  gctcacgcct gtaatcccag cactttggga ggccgaggcg ggcgcatcac gaggtcagta
6481  aatcgagacc atcctggcta acccgtgaa accccgtctc tactaaaata caaaaaaatt
6541  agccgggcgt ggtggcgggc gcctgtcgtc ccagctactc aggaggctga ggcaggagaa
6601  tggcgtgaac ccgagaggcg gagcttgcag tgagccgaga tcgcgccacc gcactccagc
6661  ctgggcgaca gagaaagact ccgtctcaaa aaaaaaaaa agaaattaaa ggtggctgga
6721  cacattggct ggtgcttgtc atccgagcta cttgacaggc ggaggcaggg ggatcgcttg
6781  aggccaggcg tttgagacca gcctgggcag catcatgaga ccctgtctct agaaaaaata
6841  aaaaaattag ctgggcatag tggcgcaggt ttgtagttcc agctaccggg gatgctgagg
6901  cgggaggatt gcttgagccc acgagttcga ggctgcagtg aactattatt gcaccactgc
6961  acccaacttg ggtgacagag accccatctg tttgtttgtt tgttttgag acagagtttc
7021  gctcttgttg cccaggctgg agtgcaatgg tgcaatcttg gctcaccgca acctctgccc
7081  ccaggttcaa gcaattctcc tgcctcaacc tcccgagtag ctgggattac aggcatgcgc
7141  caccatgccc agctattttt tttttttttt tgtattttta gtagagacgg gattttctcc
7201  atgttggtca gtctggtctc caactcccga cctcagttaa tcccccaaat tggcctccca
7261  aagtgctggg attataggcg tgaaccactg tgcccagccc gagacccat ctcttaaaaa
7321  caaaataaaa caaaacaaaa acggccaggt gtggtggctc acacctgtaa tccccaaact
7381  tgggaggccg aggcgggtgg accacttgag gtcaggagtc tgtgaccagc ttgccaacat
7441  ggtgaaaccc catctctact aaaaatacaa aaattagctg gcatggtgg tgcgcacctg
7501  taatcccagc tactcagaag ggaggctgag gcaagagact caattgaacc caggaggcgg
7561  aggttgcagt gagccgagat tgccccactg cactccagcc tgggtgacaa agtgagactc
7621  gctctcaaaa aaaaaaaaaa gaagaaatta agatgaaag aaaacaaaca ttccaaaaag
7681  ttgagaaaga attgcctttt gtccagcccc actcccaacc ccccaaccct gttgtaatgt
7741  gtgatctgtt ttcttccagt ctcgtttcct ctcagtccat ccaccccttca tggggccaga
7801  gccctctctc cagaatctga gcagcaatgc cgtttgctga agacaagacc tataagtata
7861  tctgccgcaa tttcagcaat tttgcaatg tggatgttgt agagattctg ccttacctgc
7921  cctgcctcac agcaagagac caggtgagca agggaagtga cagcccgaca ctggcctggg
7981  ggcagggctg tggaattcaa agctcagccc catcctagtt cctcacccaa gcctgggctg
8041  gctccttcct tcttcctctt gctgtgtctt gctccttgtc cttgctgctt ttctttttt
8101  ttttttttt tgagattgag tctcgttctg tcgccaggct ggagtgcagt ggcacgatct
8161  tggctcattg caacctccgc ctcctgggtt caagtgattc tcctgcctca gcctcctgag
8221  tagctgggat tacaggtgcg tgccaccacg cccagctaat tttttgttt ttaatagaga
8281  cggggtttca ccatgttggc caggatggtc ttgatctctt gaccttgtga tccgcctgcc
8341  tcggcctccc aaagtgctgg gattacaggc gtgagccacc gcacccttgc tgcttttcta
8401  acttttggat ggagtgtggc tcagggtggc gttgctgact tcgccgagct cccccttgtg
8461  ttgcttttgt gcactgctca aaaatatggc gctggctctc tgagatttcc tggctctggt
```

-continued

```
8521  ccacttgccc actttttttg gaacctccta tttccttcat ctctcttgcc cttccttgtc
8581  ctgctcagtt ttgattccat tctccttgtc atggggccct gtcctggcac ggagctggga
8641  ctcaggtttg agagctggca ggatcagggt cgctctagcc ccaacagaac ttgctgcagg
8701  cccctggcac tcactagctg gtgaaacggg cacaaccccct ccccgttgta gctgctgttc
8761  tcagattgga cccctgtgct ccagagggta cctgttggct cttttggggc ctcctgtcct
8821  cagatttctc aggagcccca ttgttgtctc cgctgtcctc ccacacagat cgcattagta
8881  tgcaggtctg tttggagttt gctcctccct cttgtatttt ggggtttata gggatatctt
8941  gttttatagt aaatattttc tgtgggtttt cttatttttc tttaaaaaat ttttttttga
9001  gacggagtct cgctgtgttg cccaggctgc agtgcaatgg catgatctca gctcactgca
9061  acctctgcct cctgggttca agtgattctc gcgcctcagc ctcctgagta gctggggtta
9121  caggcgcatg ccaccacacc tggctgattt tgtatttgta gtagagatgg agtttcacca
9181  tgttggccag gctggtcttt attttatttt ttgagacaga gtcttgctct gtcactcagg
9241  ctggagtgca gtggcacgat ttttttttttt ttttgagacg gagtctcact ctgtcgccca
9301  ggctggagtg cagtggtgtg atctcggctc actgcaagct ctgcctcctg ggttcacgcc
9361  attctcctgc ctcagcctct tgagtagatg ggactacagg cgcctgccac catgcccggc
9421  taattttttg tattttttaat agagacgggg tttcactgtg ttagccagga ttgtctcgat
9481  ctcctgacct catgatccac ccgcctcggc ctcccaaagt gctgggatta caggcgtgag
9541  ccactgcgcc cagcattttt ttttttttttt ttttgagat ggagtctcgc tgtgtcttcc
9601  aggctggagt tgcagtggtg ccatcttggg tcaacctctg cctcctgggt tcaagcaatt
9661  ctcctgcttc agcctcctga gtagctggga ttacaggtat atgctaccac acccggctaa
9721  tttttgtgtt tttagtagag acggactttc accatgttgg tcaggctggt cttgaactcc
9781  tgaccttgtg atcctcggcc ttccaaagtg ctgggattac gggtgtgagc taccgcacct
9841  ggctattttc ctttttctaa aaatctagct cctgcaggat tctgtgggtt tttgtttctg
9901  ctgtctggtt gcttgttttt atgtgagaat tcaggtagac ataaaaactc tagggctggg
9961  cacggtggct cacgcctgta atcccagcgc tttgggaggc caaggcgggt ggatcacctg
10021 aggtcaggag ttcgagacca gcctggccaa catggcgaaa ccatgtctct actaaaaata
10081 caaaaaaatt agccgggtgt ggtggtgggc tcctgtaatc ccagctactc gggaggctga
10141 ggcaggagaa tcgcttgaac tcaggaggca gaggttgcag taagctgata tcacggcact
10201 gcactccagc ctgggcgacg gagtgggact ccgtctgaaa aaaaaaaaa aaaagaaac
10261 aaaaaaactc tgcagccact gtcatctgcc cacaatctcc ccagcattct cagcttcctt
10321 gtttgttatt gtcggccccc tctctttccg tcttttgccc cttttcatcat acttttgcta
10381 tctaccttt ccttctctcc taatccaaac ctttctttttt gccctggggg ccatattaat
10441 ccaaggcttt tgtatcagat taactgggtt tggattcctg ccccactgtt ttaggatctt
10501 tgctacagta ctttgcttct gctaagcctc agtttcctca ttagtaaagt ggagataata
10561 atggcattaa ataaagatga tacatgcaaa gcccttaatg gagagcccag gacatagtta
10621 attgccagtt tccggcagct gcctttattg atgtggctgc taattgctct tcctcactcc
10681 atacctggcc ctgtcctggg ctccgatcca gtttcacgtg gctgccttgc ccttgtggct
10741 ttcttggcac ccctccccccc gctgtggctt cattctgggt ggggaagtgg caggggccac
10801 ctggcttgag caggacagtg gcattgtgtc ttccaggatc gactgcgggc cacctgcaca
10861 ctctcaggga accgggacac cctctggcat ctcttcaata cccttcagcg gcggcccggc
```

-continued

```
10921  tgggtggagt acttcattgc ggcactgagg ggctgtgagc tagttgatct cgcggacgaa
10981  gtggcctctg tctaccagag ctaccagcct cgtgagcgtc ctgcccttgc cctcctggac
11041  ccccagcctg ctccctggcc tccgctctcc ttttctctct ccctgtactt cctgcctttc
11101  tctgtcatcc tctttcttgt cactgtgaag cgatgaataa acctgggtgt agatccaggc
11161  tgagccactt accagctgtg tccctttggc caagtccctt aatttccctg agcctcaggc
11221  ctctcttctg taaaatgaag ctcatggcag catctgccgc ggggagctgc agtgggtgat
11281  actgcgggac gatgcgtgtt gagtattgag ctgggctggg cacttcctgt atgcccagca
11341  catggagtct ccctaactt tcacggctgt agcattcgcc tcccacccctt cctcatttct
11401  tctcccccac ctactcattc accctccctc tctcctcctt ctcttcccct ccctggtttt
11461  accctgagag ccttcgacgc cctctatcag ctgcccagtt attctttaag tccctctcag
11521  tgtccctgcc actctgagtg ctcggaggcg atttgatgag attgagtttg atcctgagtg
11581  agatcaagac atgggaggag gctgggcgcg gtgtttcaca cctgtaatcc cagcactttg
11641  ggaggccgag gcaggcggat catgaggtca ggagatggag accacccctgg ctaaaacagt
11701  gaaaccccgt ctctactaaa aatacagaaa attagccggg catgttgtcc cagctactca
11761  ggaggccgag gcaggagaat cacttgaacc agggaggcag aggttgcagt gagctgagat
11821  cgcgccactg cactccagcc tgggcgacag agtgggattc catctcaaaa aaaaaaaaaa
11881  aaagacatgg gaaaaaaaat caagccagcc ctatttatat ttcaaactag aggtaacccc
11941  cgagaccctg gtcacattta tagctgtggg acatccatgt ttttcttttc tttctctctc
12001  tttttttttt ttccttttag agacagagtc ttgctgcgcc acccaggctg cagtgcagtg
12061  gtgcaatcat agctcactgc agccttgacc tcctggactc aagtgatcct tctacctcag
12121  cctccagagt agctgggact acaggcatgg acaactacac ctggctaatt tttaaatttt
12181  ttgtagagat gacatctcac tatgttgccc aggctggtct caaactcctg ggctgaagcg
12241  atcggcctcc cagagtgctg ggatcatagg tgtgagccac cgcgtctggc tctcatgctt
12301  gcttttctct ccttttttccc ttccttgctt ttcctccctc cctccctccc ttcctctctt
12361  ccttccttt tttccttcct tcttttttaaa tatgtctctt catgtgtgga gattaatagt
12421  gatccctggc tgggcacggt ggctcacgcc tgtaatccca gcactttggg aggccgaggc
12481  gggcggatca aaggtcagg agttcgagac cagcctggcc aatatggtga accctgtctc
12541  gtaccaaaaa tacaaaaaaa ttagctgcgc atggtggtgc aagcctgtaa tcccagctac
12601  ttgggaggct gaggcaggag aattgcttga accggggagg tggaggttgc agtgagccga
12661  gattgcgcca ctgcactcca gcctggatga cagagtgaga ctccgtctcc aaaaaaaaaa
12721  aacccaaaaa tagtgatccc ctgaatacaa tggctgtggt agggcctgat gaggggtggg
12781  ggcaaagggg aggggctcag gtggcagcat cagggcaggg gtcagtgagc aatgatagtc
12841  atgtggagga gaaagccact gggtcctagg atgcctgggg acagagaaga gtgactgctg
12901  acacggcgtg ggtgactaga gacccacgag gccccccccat actcccccttc ctcccttgct
12961  accttgtcct ccatctgctc tcaccctccc actcctgccc ccttgccaag tgatgcttgt
13021  cactcctttt tttttttgaaa tggagtttcg ctctgtcgcc caggctggag tgcagtggtg
13081  ccatctcagc tcactgcaag ctccgcctcc cgggttcacg ccattctcct gcctcagcct
13141  cccgagtagc tgggactaca ggcgcctgca accatgcccg gctaacttt tgtatttttt
13201  agtagagatg gggtttcacc gtgttagcca ggatggtctc gatctcctga cctcgtgatc
13261  cacccgcctc ggcctcccaa agtgctggga ttacaggcgt gagccaccaa gcccagccct
13321  gcttgtcact cttgaggagt gggcccacat cagaacagct tttggaccta tgggtggggc
```

-continued

```
13381  gggggtgta cccaagagca cccaagcctc tttaatcatg aggagaaccc ccaattcctt
13441  ttttttgag acagagtctt gctcagtcgc ccaggctgga gtgcagtggc atgacttcgg
13501  ctcaccacaa cctctgcctc ccgggttcaa gtggttctcc ttcctcagcc tccctatagt
13561  ccctgattcc ttctattttt ttttttttt tttgagacgg agtctcgctc ttgttgccca
13621  ggctggagtg caatggtgca atctcaggtc atggcaacct tcacttccca ggttcaagca
13681  attctcctgc ctcagcctct cgagtagctg ggattacagg catgcgcctc acgcctggc
13741  taattttgtt attttagta gagacagggt ttctccatgt tggtcaggct ggtctcgaac
13801  tcacgacctc aggtgatcca cccacttcgg cctcccaaag tgctgggatt acaggcgtga
13861  gccaccacgt ctggcttctt tttctttttt tcccccgaga cggagtcttg ctctgttgcc
13921  caggctggag tgcagtggcg cgatctcagc tcactgcaac ctccgtctcc caggttcaag
13981  caattcttct gcctcagcct cctgagtagc tgggattaca ggtgcttgcc agcacgcctg
14041  gctaattttt gtattttag tagagacggg gtttcactat gttggccag ctggtcttga
14101  actcctgacc tcctaatcca cctgccttgg cctccccaaa tcctgggatt acaggcatga
14161  gccatcgtgc ccagcccctg attccttctt ttttttcttt tcttttttt tttagacgga
14221  gtctcgctct gtcgcccagg ctggagtgca gtggcgcgat cttggcttac tgcaagctcc
14281  gcctcccggg ttcacgccat tctcctgcct cagcctcctg agtagctggg actacagggg
14341  cccgccacca tgcccggcta ataataatgt tgtattttta gtagagatgg ggtttcactg
14401  tgttagccag ggtggtctcg atctgacctc gtgatctgcc tgccttggcc tcccaaagtg
14461  ctgagattac aggcatgagc cactgtgccc agccctgatt ccttcttgat atcactacat
14521  ctttgtcctc tagggacctc ggaccgtccc ccagacccac tggagccacc gtcacttcct
14581  gctgagaggc cagggccccc cacacctgct gcggcccaca gcatccccta caacagctgc
14641  agagagaagg agccaagtta ccccatgcct gtccaggaga cccaggcgca agagtcccca
14701  ggagaggtct gtcctcatag tctaccttga gccaccactt tgtgttcct atctgcccac
14761  ttctgcccat tgagccttcc agaaaccctc tcccgtcccc tataaatcac gcctaatctc
14821  tgctcagaac cctagggctt cctcagtggg gatctgcccc agaccagctt ccaggctgct
14881  gaccaggtct tcaccctgtg gcagccctaa tcctctgtca gcaaccagct gggagaccac
14941  agttttgtgt gtgtgtgtgt gtgtgtgtgt gacagtgtct cattctgtca cccaggctgg
15001  agtgcagtgg agtgatcttg gctcactgca acctctgcct cctgggttca ggtcattctc
15061  ctgcctcagc ctcctgagta gctgggatta caggcaccca ccaccacgcc cagctaattt
15121  ttgtattttt agtagagatg gggttttgcc gtgtcagcca ggctggtctc gaactcctga
15181  cctcaggtga tctgcccacc tttgcctccc aaagtgctgg gattacaggc gtgagccacc
15241  gcacctggca atgctgtgtg ttttctgtga ggtagacgta aggacacctg tggacagagg
15301  gtctgggaat taccagaacc caggcaaggg ctcccctggc tcctgtgctc catggtgtgg
15361  gctgaggcct ataggagatg ccccaagagc acaagctgcc ctttgtgagc tcttgggaga
15421  ggcaactgcc ttattcatat ttttccctcat tgcagaattc agagcaagcc ctgcagacgc
15481  tcagccccag agccatccca aggaatccag atggtggccc cctggagtcc tcctctgacc
15541  tggcagccct cagccctctg acctccagcg gcatcagga gcaggacaca gaactgggca
15601  gtacccacac agcaggtatg catggaatct ggaattatag ggtccttctg atctctcaag
15661  tgagggtaag aattagagtt gccccatctg gcttccttga acaggagaca aggtgggaat
15721  aaagggagtt caacccagga agcaaaccag ttccttagtg ggtgtatcag ttagcatttg
```

-continued

```
15781  ctgtgtaaca aatagtccac tccagttttc caaattttt ttttagtagc ttaaaataca
15841  gccatttatt tagcatatga tcctgtgggt caggcatttg gctacctac atgggcattt
15901  cttctggtct tggctgaatt tcctctcaag tactcaccgg tatatacata agttctgcct
15961  ctggctgttt gctgagcacc ttggttctct tctatgtagt ctctcatcct ccagcacaca
16021  aacccatcat ggcagctggg cagagttctc agagagggct caaaactggc acagtgtccc
16081  ctgtgctcca ttctgtgggc aaaagcaagt tataaggcca gcctagattc aaggagtagg
16141  gaaatagact ccctccctag acgggaggac tgacaggcac agtgcagtgg ggctgggtgg
16201  agatgagcga gataagtagg gccattttg cgctctgcca aagggactgt agggaacagc
16261  cagggcctat agggcagtgg gagagggaca gtgaagggct gcatcagctg ttggcagggg
16321  aacctttagg cactgtctta ccgcagagat ctccagttcc cagtgaatca tgaaaacttc
16381  tcagtcccca gaggaagtaa ggtcttcatc atccagtggc ctggactcaa ctccagatgt
16441  cagtgctccc cctcagaaat atatagttgt ccatctggac ctctcaggcc agcatgtctc
16501  tttcctactt cccaaactat tccacatgac gctggtgccc agtcagccct cagtgccctg
16561  ggacagccac aagacacatg agcagttaga ggctgggaga cgtcatctta gtacttttgt
16621  catccccaaa ctgctccaag cacctgtctg ctttgcagtg tcacctggcc acgggatgcc
16681  tttcaggagt tgctgtagac cacagaggca gagggcgctt aggtttcagt acgtttgtag
16741  acacaggtcc catgagattc tgtggtatta gattgtggtg ggggagctgt acatcagaat
16801  caccctgact tttgccagct gtggggcttg gcatgtgcat tccgagttcc gtggagagtc
16861  ctgctgcaac tgcctttaca gaccatcacc acctgctatc ctctgcttcc cccacccagg
16921  tcaggcagcc tcccaggggt ggctttgtcc ttgtcccctc tcttcccaag cctccgggat
16981  ggccaggcct ctcggctggt gtgagctgtt ctgcatgagc catcctgcca cccttgccc
17041  tgatccatgg ctgctccac tcatggtggt aggagaggga cagcagtggg ggaagtgtcc
17101  aggattgcat gaggctaagg tcaaagtaga aaaggtagac acaggagagg ggaggtttcc
17161  caggtgggag aggaaaaagc ggagagaata attaataatg gtcttcaggc tcctaggtac
17221  catttcactg tgtgccagga cagacctggg gctacaggtc aaggactgag ggcagctgtt
17281  gggctttcag gccaggaagc agtgaccaaa gggactgtgg catctcctcc aagggcagga
17341  gatttggagg cctagacaca gtagggacca tgagatctgg gccagaggga cccttctcca
17401  ggcctcaagg taatggtctt tgggtctgtg tttccacttg tgttttttcca ccggcaggtg
17461  cgacctccag cctcacacca tcccgtgggc ctgtgtctcc atctgtctct ttccagcccc
17521  tggcccgttc cacccccagg gcaagccgct tgcctggacc cacagggtca gttgtatcta
17581  ctggcacctc cttctcctcc tcatcccctg gcttggcctc tgcagggggct gcagagggta
17641  aacagggtgc agagagtgac caggccgagc ctatcatctg ctccagtggg gcagaggcac
17701  ctgccaactc tctgccctcc aaagtgccta ccaccttgat gcctgtgaac acagtggccc
17761  tgaaagtgcc tgccaaccca gcatctgtca gcacagtgcc ctccaagttg ccaactagct
17821  caaagccccc tggtgcagtg ccttctaatg cgctcaccaa tccagcacca tccaaattgc
17881  ccatcaactc aacccgtgct ggcatggtgc catccaaagt gcctactagc atggtgctca
17941  ccaaggtgtc tgccagcaca gtccccactg acgggagcag cagaaatgag gtgagtcctc
18001  gcccttcctg gcagggatcc tggccccttc cccgggaca gcttgcccac ctggccctgg
18061  ccttggcccc ttcccagtct gcattctgtg tccagcctgt gctgctctgt ggcctctcct
18121  tgagggcata cagacagttg agaaccagcc tcatgcaggc cccacaccat gttctccagg
18181  aggaacagtc attgagcttc taagtctgga caccctcagga gggtcagcca caggggcac
```

-continued

```
18241  ccactggtca ggtgtataag ttcatttagg gctcgtagtt cctagtgaag ccgagcggtg
18301  ccgttttgca cataaggaag cagtgacggg gacagcacag tggcccatct gcctcttgcc
18361  ttgctcttca ccaggatgcc tggtgtgtcc ctccatggcc aggctttaca gaacgcagtc
18421  ccacctggag cagccactcg gacccagcag ccccccattg ttgcctgctc caagcctcac
18481  atctaaccct agctgcggct gtctgctggg aagagccaag tccatagggc cctttgggca
18541  catggccagg cctctgaccc tgtggctgct ctctagttct caggcccagg caggatgtca
18601  gtgcaggatg gagccccgcc ctaccaaagg cttccaggtg gcatgagct cacaggcagg
18661  ccagggagta gggaaaggct gccctggagg aggccaccat tggtgcagat tcttggtccc
18721  ctctaccccc actgctccaa gaaaaggtgg cctaggggca ttatagattg ggaattgagg
18781  ggttggagtg ttagttcatg ccctggcctg gaatgggac cgccctacca ggttcgtctc
18841  cctgccaacc ccagtccctt ccagtgctct cctttctttc ccaggagacc ccagcagctc
18901  caacacccgc cggcgccact ggaggcagct cagcctggct agacagcagc tctgagaata
18961  ggggccttgg gtcggagctg agtaagcctg gcgtgctggc atcccaggta gacagcccgt
19021  tctcgggctg cttcgaggat cttgccatca gtgccagcac ctccttgggc atggggccct
19081  gccatggccc agaggagaat gagtataagt ccgagggcac ctttgggatc cacgtggctg
19141  agaaccccag catccagctc ctggagggca accctgggcc acctgcggac ccggatggcg
19201  gccccaggcc acaagccgac cggaagttcc aggagaggga ggtgccatgc cacaggccct
19261  cacctggggc tctgtggctc caggtggctg tgacaggggg gctggtagtc acactcctgg
19321  tggtgctgta ccggcggcgt ctgcactagt gaagccctgg gctcttccca ccacccatct
19381  gttccgttcc tgcagtacac ctggcccctc tccgaagccc cttgtccctt tcttggggat
19441  tgtggaggct gggtcagagg ggagttaagg gactgcaggc ctggcagcag gacatgcctt
19501  ggctgaacca agtcctgaga gcagcatctc tgtccccacg gtgccttgtg tgggtccccg
19561  tccttggctt tctgggtcct gggctgcccc cagtgctcca gaccttcccc actggcaatc
19621  caggttatca tccatgtcct ccagaggagc ttcctcctcc aggcctcagc cctgttggcc
19681  caggtggagc aggagggacc actggaacat gtggtgcttg gaatgcctc tcctgttgca
19741  ttggtccctg aaggcctcag ggcaggtatg tggtgtgtgg gcgactccac aagacctgcc
19801  tcccatcctg gcagcccagc ctgagaccgt tgcattgagg caggcaggag cggcagggtg
19861  gctgctctcc aggagcccaa ctgccttgag ttcctgcccc actgggcccc ctcccctgct
19921  gggcaatcct gggaaggtct ggaggttcct gtggacctca gggaagccag gggcagctgt
19981  caggcctgag gaagacctgt ggagctcctc tccagcctcc tctttccctc ccctctggtc
20041  tccattctct tcagctccct acatgggctg gggaggagac acctggtggg cagagctcag
20101  gcagaggttt ggatttcagc tccctcactt ccggggctgt gtggctttgg cagatgtcag
20161  acttctggtc ttgcttctcc acgtggacag tgagtatctg gtcattctt cactggggttc
20221  ttctgagatt gaacctacag gtgtttgcca agtgcctggc ccagagcaag tggccactgc
20281  ttctcccatc tctctcctgc ccaacctggt agagctgagg gcatgagagg cagagtgcac
20341  agtggtcaag ggtgcagctc tgcagcacag gcagcctagg cctgcgtccc aacctgcctc
20401  tcaccagctc tgtgaccttg gcaagggat ttatctgtct gtcccttagt tttctcacct
20461  gtaaaaggag gataagtata tatatatatt tcccagtgtt gtgaagatta aaggagttta
20521  tcgatgtagg tcttaggatg agtcctggca tttaccaagg gttggatata tgttattatc
20581  actattaagt gttgagggtc caggcatgct gggcaacagg gacccatct ctacaaaaaa
```

-continued

```
20641 gtttaaaaaa ttagccaggc gtggtggtgc acctgtcgtc ttagctactt gggaggctga
20701 ggtgggagga tcacttgagc ccagaagctt gaagctgcag tgagctagga tcgtgccact
20761 gcactccaac ctgggtgaga gagcgagacc ctgtctcaag aaaagaaaa atgcagagaa
20821 acaggagtct tggctactcc tttagaggca gactcagacc ctcctgcctc acagctttat
20881 ctttgtattt gccccttact ttatcttgtg ccttgagaaa ttgctgggga gagaggtatg
20941 tccactgggc agctgtacag gatggaggat atagggcgtt tccactccca gcagccaggt
21001 tccctcaccc caagctcacc cactgttggg gagattatct acaataacac cagaaacaca
21061 ttggggtgga ttgggggtat ccttatgggt tcttttcagg gaaccattgc tggacaaggc
21121 acaggagcca cctccatttc tgagctctgc aagggacaag aactagagcc atcagggct
21181 gggctcactg tggccccacc ccaagccgtc agcctccagg gatctacacc ctgccttggc
21241 tgctacagct ttttcactcc actgccctag gggagttcag caacctaatg atctctatct
21301 ctgaacatct cttcatccca tgctccaagt ccagcaacct gcaccctgga accaggagtg
21361 gaccctaccc gagctgtctg tattaatccc catcccccac caccaatctt aaaaagccct
21421 ctgtcccct accctaaacc ccagttaggt acccatgctg ggcaggtcag ttaacaattt
21481 atgcacaggt actagtttta ttgtattacc gttccagggt agctttgaaa aagtatctc
21541 aaaaaggcaa catgggccga gcgcagtggc tcacgcctgt aatcccagca ctttgggagg
21601 ccaaggtggg cagatcgcct gaggtctgga gttcaagacc agcctggcca acagggtgaa
21661 accccgtctc tacaaaaata gaaaattag ccaggtgtag tggcagacgt ctgtaatccc
21721 agctattcag gaggctgagg cacgagaatt ccatgaaccc aggatgcgga ggttgcagtg
21781 agccgagatt gtgccactgc gctccagcct gggcgacaga gtggtattct gtttcaaaaa
21841 aaaaaaaaaa ggcagtatgt agccccgaag actgttgccc aagtggtaga atgttagcac
21901 actaccagcc taggtaaaaa atacaaaag taactgggca tggcggcgcc catctatagt
21961 cccagctaca tgggaggctg aggtgggaag ataagtcact tgagcccgcc aggaggcgga
22021 ggttgtagtg agctgagatc gcaccactgc actccagcct gggtgaccga gtgatactct
22081 gtctcaaaga aaaaaatta taattttagc acagtaacca gccatgatgg gagatacct
22141 gggtaaggca tgtagaaagg gttgagggac cttcccagtc ccctagccc gcctcccatc
22201 ctcccatctt tttcttttt ctttttttta gagaatcacc cagcctggag cgaagtggtg
22261 caatcataac tcactgtatc cttaaactcc cgggcttaag cgatcctcct gcctcagcct
22321 tctgagtaac taggacttca ggtacctgtc accatgcctg gctaattaaa ttttttttc
22381 ttttttttt ttgagatgga gtcttgctct gtcacccagg ctggagtgca gtggcgcgat
22441 ctcagctcac tgcgacctcc acctcctggg ttcaggccat tctcccgcct cagcctccag
22501 agtagctggg actacaggcg cctgccacca cgcctggcta atttttttgc acttttagta
22561 gagacggggt ttcactgtgt tagccaggat ggtctcgatc tcctgacctt gtgatccgcc
22621 cgcctcggcc tcccaaagtg ctgggattac aggcgtgagc caccgcgccc agccaaatta
22681 aatttttat agagatgagg tcatgctgtt atgttgccca ggttggcctc atgagatctt
22741 gccttagcct cccaaagtgc tgggattaca gatgtgagac actgcaccca accccacca
22801 ctttttttt tccttttct ttttttgaga cagtcttact ccgttgccca ggctggagtg
22861 tagtggcatg atctcagctc actgcaacct ccgcctccg ggttcaagca attctcctgc
22921 ctcagcctcc cgagtagctg ggattacaga ggcctgccac cacacccgac taattttcgt
22981 attttagta gagacggggt ttctccatgt tggccaggct gttcttgaac tcctgacctc
23041 aagtgctcca cctgcgttgg cttcccaaag tgctgggata caggagtgag ccactgcgcc
```

-continued

```
23101  tggctgatcc cagcactttt caaatgatgc cgctcaaagc cgtgacttgg cctactttga
23161  acagcaaact tgttgctgct gttgtcaacc tgaaggcctc tcaaatgcca gcttcaagca
23221  gggtgtgaat tggccagtgt cagatctcag gagtcctgtg ttgagagtgt ggctttcagc
23281  tgcggggagc tgcacttggt ggggaaagcc aggcaggtca ccctcacagc cagataatgt
23341  ggaggtcaga acccaaggaa gggagtgaga cctccactcc cagtggggga cctggccacc
23401  catccttggg gacctgagaa agcgtacttc accttggggt gaaggctggg tggggccaga
23461  gggaccagtg ccctcctcag tgcttagggg cagagccacc tgcagcaatg gtatctgcat
23521  attagcccct ctccaccttc tttctcccgc tgaatcattt ccctcaaagc ccaagagctg
23581  tcactgcttc tttctccctg ggaagaatgc gtggactctg cctggtgata gactgaagcc
23641  agaacagtgc cacaccctcg ccttaattcc ttgctaggtg ttctcagatt tatgagactt
23701  cttagtcaaa tatgagggag gttggatgtg gtggcttgtg cctgtaatcc cagcattttg
23761  ggaagccgag gtgggaggat cccttgaagc caggagtttg agacaagcct gggcaacaaa
23821  gcaagaccct atctctaaaa aaaaaaaaaa aaaaaaaaaa aaaaaaaaaa aaaaaaatc
23881  taggagatgc tctttaccct gcctggcctc aaactattaa tagcttcctt tgagcaacat
23941  tatttattat gaactttcaa acacaaaaaa gtagagagag tagaataaca aatccccatg
24001  agcccatcac ccaacttcag taattatcaa ttcatggcca tcttgttcac ccctgcctgc
24061  ttccctgctt cccctcattc tgcagaggtt cttttctttt gagacagagt gttgctctgt
24121  tgcccaggct ggagtgcagt ggtgcaactt cggctcactg caacctccgc ctcccaggtt
24181  caagtgattc tcctgcttca gcctctcaag tagctgggat tacagatgcc cgccaccaca
24241  cctggctaat tttcgtattt ttgttagaga tggggtttca ccatgttggc caggctggtc
24301  tcgaactcct gacctcaagt gatccgcccg ccttggcctc ccaaaatgct gggattacag
24361  gtgtgaacca cggtgcctgg ccactgtaca ggttatttat agaagttgga gagtgaaggg
24421  ttgagaaagc caaggggcag atgcgggtct ggaggatttt gtgcctaagg ccctctcttt
24481  gctcccagac agcatgaagt aacaatgagg catccacctc ttggttttgt ggcctctgtg
24541  gatgacgtct ctcaccttga accagttcag agttggagta gcgcaggatc ctgtcttcag
24601  aggaggggcc gaagcgggtt cctctgttgt caagctcttt ggaggtgcct ggctgctact
24661  actgtcccag agaggtgatg atgaatgatg ggtgtgtcca gtggcagttt gccccactga
24721  ggcaggggct tccactaggc cctgacagag cccttccagc aggcagaaat ccctgtgcta
24781  ggcaagattc aaactccgta gcatgtctcc tgctcccatc tcttaggaat ggagtccttc
24841  aggccttgag tcccacattt tccatgatgc tccattaagc agctgatagc accccccacct
24901  ccagggaaag tgagttcaga gtccttggtc taatgcatct gtgttgaaat tgaggccttc
24961  ccctgtgttc acctttctgc tcttttttctt ttagcccaag gctatgaagg cctcattcgg
25021  tgctgggcat ggtcactcct agcattcctc actctgttgc taacagcaac agcaataata
25081  ataagggtta caacttactc cataccttac tgtctgccag gcattaagct aagtgcttta
25141  catatattaa gtcatttaat cctcataatg accctatgaa agagatacca tctcaaccca
25201  attgacagct ggtttgcaag attaggaggg atgaaggacc caggggacaa tgcgagggaa
25261  aactctgacc ccggggcccc aggctggatg ttctttatgc ctgtgaacca cagcttatca
25321  catgtctgga gttagggacc ccacttaaag tgagattttg gctggaggtg gtggatcata
25381  cctataatcc cagcactttg ggagaccaag gcagaaggac tgcttgaggc caggagttca
25441  aaaccagtgt aggtaacagc tagaccctat ctctacaaaa aatttaaaaa ttagctgggt
```

```
                       -continued
25501  gtggtggtat gtgcctcaag ttccagctac tcaggaggct gaggtgggag gatcacttga
25561  gcacaggagt ttgaagttac agtgagctat gatggcacca ctgcacttca gcctaggcaa
25621  cagagggaga ccctgtcttt aaagtacata gaggtttttc acaccaacac atctctgccc
25681  agtgtgccaa catctgccac ctgctataat agtactataa cactcaatat gtaattaatg
25741  tagtctcagg gatgttatga caatatgatt acaactatca cgtgtgtgcc cagccaggct
25801  caatgcccca ggctgggcga ggtggggcag gggacacagc ctaaaatgcc aggcctcagg
25861  aagccatttg gtttagcaga cattgtttat taaaggagtt acctatgcca gatcgaaggc
25921  ctaagatgat taagacacta tgagtgcctt caagtggttg gggacgttca tgattgtggt
25981  acagacaaat aggctttcac atcattcttt tatgtaatca tacaacagat atttgcacct
26041  acatgtgcag agcactgtga taggcctcag tgacacagaa taatacggca aagaccccac
26101  ccgatgagcc ccctcccacc acccaccagt acagtagggg gtggtttaat ggagtgttcc
26161  tggaatatga agtgggggca ggcattaggg gtggcaaagg acaagtgtt tatctgatca
26221  gttatgtact gtttataata agtaaatcag cagaggggga ataatactta gaacctatag
26281  agagtaaatc tgacaagatg aaatgctgat gaaatatgg aggaaatgaa actctcatgg
26341  gttttgcagg gaatctaagt cagtgctgtg ttgtgaatgt aggtgtaccc tttgaattca
26401  tatgttgaat cctaaccccc aaagcaatgg cattaagagg tggggccttt ggggctgggt
26461  atggtggctc atgactgtaa tcccagcact ttgggatgct ggcaggggc agatcacttg
26521  aagccaggag tctgagatca gcctggccaa catggtgaaa ccccatctgt actaaaaata
26581  caaaaattag ccaggtgtga tggcgtacat ctgtaatttc agccactcgg gaggctgaga
26641  caggagaata gcttgaaccc agtaggtgga gatttcagtg agccgagatc gtgccactgc
26701  actccagcct gggtgacaga gcgagactcc atctcaaaaa ataataaaag atgtggggcc
26761  tgtgggaggt ggttaggtca tgagggtgga gatcatgaat ggggttagca ccttataaaa
26821  caggcttgag ggagcccttc tgtccccttct accatgtgtg gatgcagtga aaggcaccg
26881  tatctctgaa gcagagagcc cgccctggac actggatctg ctggcacctt gatcttggac
26941  ttcccagcct ctagaactgt gagaaatat tttttgttgt ttacaaatta cccaggctaa
27001  ggtgtttcat tgtaacctga atggaccaag ctggtgtgac cctgttggaa aactggcagt
27061  atctaccaaa agccgaacat acgtataaac tgatccagca gttccactcc tgggtatgta
27121  caccacagaa agctatgtcc accgagacat tggcaagaat gtttctaacc acacgctgac
27181  tgtagcccca aacctgaaac aacccaaatg tccatccacc aacccaaatg tccatccaca
27241  gttgaagcta cagtgaagtc acagggtcga atactactgc acagcaacga atatgaatga
27301  aaatatcgct atgcacagca acatggataa atttcacaga catgaggtca agcaaaagag
27361  gtcagagtcc tcatcatcaa gagagaattc attgtatgat tctcttccta caaaaagtac
27421  agaaataagc aaaactgatc catggtgtta gaagccaggg gaacagttaa caggggaggg
27481  atactgggga ggggcatcct ggagtgctgg tctacctcat ctgggtgttg atttcacgag
27541  tattgtcagt ttgtttccag actccctgtt ggagatgtgg aaataaaaac cacctaaaca
27601  agagcagaga ggccatttgg tcaaagtttg caaggagtc agccatgatt gcttgtattt
27661  ggcagggtc aaaggcaggc agggactgtg aaatgttata gtggaaaaaa agggaaggct
27721  ctgggtgtgc tgtgattgga gattgttggg atggggacag agcggactaa ctggaggggc
27781  atctttggtt ggttgggggg gtatatttgg cttctctgg ttggtctgga gttggaagag
27841  gggggtgtggt ggctgggat tgggaagaag ctggcagcca ctaagttcag actgttctgg
27901  gtccgattgc tgctgaggct gtggtttggc ttccttggct tcccaggctg gtcatgggtt
```

```
27961 tctggccaga gtctattgtc atatgtggcc tggccattgt ccagttgtat gttcagtctc
28021 ttggaaggaa gggtattgac tctgagaggg gccaccatcg ctggaatggg ggacacacag
28081 tacttcctcc agctgcctac accccctag ggtcagtggc gcctgcctgt gagggtgagc
28141 ccaatggcta gagggctctg ctccaagtca ttgcttacta cacccacaaa cattcttcgt
28201 tctttaaggc ctaacttaaa gcccagatcc tacaggaaac cttgattaga cccctctctt
28261 tattaagctt cctaagatca aaccctgctt ttgtgtaaat gctgacctcc ttgcctacat
28321 tttaaaaacc tagagctggg catgatggcc ccagcctgta atcccagtga ttcaggagac
28381 tgaggtggga ggattgctag aagccaggag ttcgagacca gcctgggtaa catagctaga
28441 ccacatctct taaaataaaa tagttaattt agccaggcat gatgatatat gcctgtagtc
28501 ccaactactt ggaaggctga ggtgtgagga tctttgagcc cgggaggtcg aggctacagt
28561 aagctatgat ctcaccactg tactccagcc tgggtgacag agcgagaccc agactcaaaa
28621 aataaaaata aaaaccctga atatcttcct tctacttctt cagtgctgtt tttatttaaa
28681 aaaaaaaaaa accagccaaa accacaactt tttactgaag tgtaatgtaa atgctgtaaa
28741 aggcagtgaa aggcacaagg gaggtggagg ggtaggaagg gtggaagtgg cgggaggaag
28801 tggcagggca ggcaaaatga agggaagccc tgggttcttg tcctgcatcc gcagccagct
28861 cccactttcc tcaccctcca ggacctgtaa actgtgaggc tggaccagtt atgtcaaatc
28921 tgtcctcccc cagagctcag tccctctgcc cttgggtgtc cttggcacaa ggcaggctag
28981 gctgcaccag cttcctccat ctccgtcctg cctcccccat ccccaggtgc cattcccaca
29041 ccatctgaat cactgatttc ctcgcaatca gacgctatct tccagttaat cacttcgctt
29101 gtatttaaca taagaaagaa aaacccttc attatcacat acagctggaa atcggcttct
29161 tgcaggaggc gtatccaaag gaattggaga agagataaac tggtaattgg tgaaagaatt
29221 actttaattt tttttcctac ttgctgtcat gatgatgtcc ttagaattgt gagcccgtgg
29281 acacttctgt acaataaatc tgctattatt acttctagaa ctaca
```

An exemplary polypeptide sequence can be found at NCBI Accession No. NP_065797.2 (SEQ ID NO: 6):

```
  1 mpfaedktyk yicrnfsnfc nvdvveilpy lpcltardqd rlratctlsg nrdtlwhlfn
 61 tlqrrpgwve yfiaalrgce lvdladevas vyqsyqprts drppdplepp slpaerpgpp
121 tpaaahsipy nscrekepsy pmpvqetqap espgenseqa lqtlspraip rnpdggples
181 ssdlaalspl tssghqeqdt elgsthtaga tssltpsrgp vspsysfqpl arstprasrl
241 pgptgsvvst gtsfssssspg lasagaaegk qgaesdqaep iicssgaeap anslpskvpt
301 tlmpvntval kvpanpasvs tvpsklptss kppgavpsna ltnpapsklp instragmvp
361 skvptsmvlt kvsastvptd gssrneetpa aptpagatgg ssawldssse nrglgselsk
421 pgvlasqvds pfsgcfedla isastslgmg pchgpeeney ksegtfgihv aenpsiqlle
481 gnpgppadpd ggprpqadrk fqerevpchr pspgalwlqv avtgvlvvtl lvvlyrrrlh
```

In addition to sensing viral nucleic acids, RLRs are important regulators of a growing list of non-infectious immunopathologies that result from inappropriate host response to self RNA. For example, the RLR family has been linked genetically to the development of Type 1 Diabetes (T1D). The gene encoding MDA5 has been found to be causative for T1D (Nejentsev et al., *Science* 324:387-389 (2009)), as patients that contain loss of function mutations in MDA5 are protected from this disease (Shigemoto et al., *J. Biol. Chem.* 284:13348-13354 (2009)).

Moreover, it is known that enterovirus infection is linked to T1D. As these viruses are specifically detected by MDA5 (Wang et al., *J. Virol.* 84:254-260 (2010); von Herrath, M., *Nature* 459:518-519 (2009)), enteroviral infection of pancreatic beta cells may result in RLR-mediated activation of immune responses that ultimately lead to T1D. Accordingly, RLRs play a role in activating autoreactive T-cells and RLR signaling can be deleterious in the context of autoimmunity.

RLR Activators and Inhibitors

In general, the invention features novel RLR activators and inhibitors that are useful in treating or preventing viral infection or autoimmune disorders. The RLR activators and inhibitors can be any agent (e.g., a small molecule chemical compound, antibody, nucleic acid molecule, or polypeptide) that increases or decreases the effects associated with RLR activation. In embodiments, the RLR activators and inhibitors are MAVS specific activators and inhibitors. In preferred embodiments, the MAVS specific activator or inhibitor is a polypeptide or polypeptide fragment. In related embodiments, the MAVS specific inhibitor is a polypeptide fragment that is a competitive inhibitor or dominant negative of the MAVS protein.

In aspects, the invention provides RLR inhibitors that inhibit the MAVS adaptor protein.

In embodiments, the RLR inhibitor comprises a polypeptide fragment of the MAVS protein (e.g., human MAVS protein). In related embodiments, the polypeptide fragment is a competitive inhibitor or dominant negative of the MAVS protein.

In embodiments, the RLR inhibitor comprises amino acids 10-77, 15-77, 20-77, 25-77, 30-77, 35-77, 40-77, 45-77, 50-77, 10-73, 15-73, 20-73, 25-73, 30-73, 35-73, 40-73, 45-73, and 50-73. In related embodiments, the RLR inhibitor further comprises amino acids from the PRR (any amino acids from 107-173, e.g., 3, 4, 5, 6, 7, 8, 9, 10, 11, 12, 13, 14, 15, 20, 25, 30, 35, 40, 45, 50, 55, 60, or 67 amino acids thereof (or any number therebetween)) and/or the TM (any amino acids from 514-535, e.g., 3, 4, 5, 6, 7, 8, 9, 10, 11, 12, 13, 14, 15, 16, 17, 18, 19, 20, 21, or 22 amino acids thereof). In some embodiments, the RLR inhibitor comprises amino acids 50-73 of the MAVS protein (GNRDTLWHLFNTLQRRPGWVEYFI; SEQ ID NO: 1).

In aspects, the invention provides RLR activators that activate the MAVS adaptor protein.

In any of the above aspects and embodiments, the RLR inhibitor or activator further contains a targeting moiety. In embodiments, the targeting moiety facilitates delivery of the RLR inhibitor or activator to the cytosol of a cell. In related embodiments, the targeting moiety contains a cell penetrating domain of the *Drosophila* antennapedia protein. The cell penetrating domain can contain amino acids RQIKIWFQNRRMKWKK (SEQ ID NO: 2).

Additional targeting moieties suitable for use in the present invention are well known in the art. Exemplary targeting moieties include, but are not limited to TAT (see Wadia et al., *Nat. Med.* 10:310-315 (2004); and Kameyama et al., *Bioconjugate Chem.* 17:597-602 (2006)) and Pep-1 (see Morris et al., *Nat. Biotechnol.* 19:1173-1176 (2001)).

In any of the above aspects and embodiments, the RLR inhibitor or activator further contains a detectable moiety. Detectable moieties are well known in the art and can be detected by spectroscopic, photochemical, biochemical, immunochemical, physical, or chemical means. Exemplary moieties include, but are not limited to, enzymes, fluorescent molecules, particle labels, electron-dense reagents, radiolabels, biotin, digoxigenin, or a hapten or a protein that has been made detectable.

The RLR inhibitor or activator can be covalently or non-covalently linked to a moiety (e.g., targeting moiety and/or detectable moiety). In embodiments, the RLR inhibitor or activator are covalently linked to the moiety. In related embodiments, the covalent linkage of the moiety is N-terminal to the polypeptide fragment. In related embodiments, the covalent linkage of the moiety is C-terminal to the peptide fragment.

In aspects, the invention provides an RLR inhibitor containing GNRDTLWHLFNTLQRRPGWVEYFI (SEQ ID NO: 1). In embodiments, the RLR inhibitor further comprises RQIKIWFQNRRMKWKK (SEQ ID NO: 2). In related embodiments, the RLR inhibitor is the fusion protein GNRDTLWHLFNTLQRRPGWVEYFI-RQIKIWFQN-RRMKWKK (SEQ ID NO: 3).

The invention further embraces variants and equivalents which are substantially homologous to the RLR inhibitors and activators described herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art The invention also provides isolated polypeptides of the inhibitors or activators of the invention, as well as isolated polynucleotides encoding the polypeptides. In addition, the invention further provides expression vectors comprising the isolated polynucleotides, as well as host cells containing the expression vectors.

The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the polynucleotides, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

In embodiments, the polynucleotides can comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In embodiments, the polynucleotides can comprise the coding sequence for the mature polypeptide fused in the same reading frame to a marker sequence that allows, for example, for purification of the encoded polypeptide. For example, the marker sequence can be a hexa-histidine tag (SEQ ID NO: 8) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the present invention provides isolated nucleic acid molecules having a nucleotide sequence at least 80% identical, at least 85% identical, at least 90% identical, at least 95% identical, or at least 96%, 97%, 98% or 99% identical to a polynucleotide encoding a polypeptide comprising an RLR activator or inhibitor of the present invention.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The polypeptides of the present invention can be recombinant polypeptides, natural polypeptides, or synthetic polypeptides comprising an RLR activator or inhibitor as described herein. It will be recognized in the art that some amino acid sequences of the invention can be varied without significant effect of the structure or function of the protein. Thus, the invention further includes variations of the polypeptides which show substantial activity or which include regions of the RLR activators or inhibitors of the present invention. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci. USA* 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors are used to amplify and express DNA encoding the RLR activators or inhibitors. Recombinant expression vectors are replicable DNA constructs which have synthetic or cDNA-derived DNA fragments encoding an RLR activator or inhibitor or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., *Cloning Vectors: A Laboratory Manual*, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine (SEQ ID NO: 8), maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods of Treatment

The invention includes methods for treating or preventing viral infection and/or autoimmune disease with the novel RLR activators or inhibitors described herein.

In aspects, the invention provides methods for inhibiting or preventing RLR-induced antiviral signaling in a cell. In embodiments, the methods involve inhibiting the MAVS adaptor protein in the cell. In related embodiments, the methods involve contacting the cell with an inhibitor of MAVS adaptor protein function (e.g., any of the RLR inhibitors that inhibit MAVS adaptor protein described herein).

In embodiments, the cell is in a subject. In related embodiments, contacting occurs by therapeutic administration of the inhibitor to the subject in the form of a pharmaceutical composition.

In aspects, the invention provides methods for inhibiting or preventing RLR-induced antiviral signaling in a subject. In embodiments, the method involves administering to the subject an RLR inhibitor that inhibits MAVS adaptor protein as described herein. In related embodiments, the RLR inhibitor contacts pancreatic beta cells in a subject.

In embodiments, the subject is at risk for, is suspected of having, or has been diagnosed with a disease or disorder associated with an inappropriate host response to self RNA and/or inappropriate activation of antiviral responses. In related embodiments, the disease or disorder is an autoimmune disease (e.g., type 1 diabetes).

In aspects, the invention provides methods for preventing or treating a subject for a disease or disorder associated with an inappropriate host response to self RNA. The methods involve administering to the subject an RLR inhibitor that inhibits MAVS adaptor protein as described herein. In related embodiments, the methods involve inhibiting RLR-induced antiviral signaling in the cells of the subject (e.g., pancreatic beta cells). In embodiments, the disease is an autoimmune disease.

In any of the above aspects and embodiments, the methods further involve contacting the cell with or administering to the subject an anti-viral agent, an immunosuppressive agent, or an anti-inflammatory.

In any of the above aspects and embodiments, the subject is a mammal (e.g., human) or the cell is from a mammal (e.g., human).

Methods for evaluating the therapeutic efficacy of the methods of the invention are standard in the art. For example, efficacy of treatment can be evaluated by assessing viral levels (antigenic levels, RNA levels, and the like), patient symptoms, autoantibody levels, and the like.

Pharmaceutical Compositions

The invention provides for pharmaceutical compositions containing at least one RLR activator or inhibitor described herein. In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing viral infection and/or autoimmune disease.

A thorough discussion of pharmaceutically acceptable carriers, diluents, and other excipients is presented in *Remington's Pharmaceutical Sciences* (17th ed., Mack Publishing Company) and *Remington: The Science and Practice of Pharmacy* (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

Methods for formulating the pharmaceutical compositions of the present invention are conventional and well known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in *Ansel's Pharmaceutical Dosage Forms and Drug Delivery Systems* (9th ed., Lippincott Williams & Wilkins), which is hereby incorporated by reference.

Methods of Delivery

The pharmaceutical compositions of the invention can be administered to a subject by oral and non-oral means (e.g., topically, transdermally, or by injection). Such modes of administration and the methods for preparing an appropriate pharmaceutical composition for use therein are described in *Gibaldi's Drug Delivery Systems in Pharmaceutical Care* (1st ed., American Society of Health-System Pharmacists), which is hereby incorporated by reference.

In embodiments, the pharmaceutical compositions are administered orally in a solid form.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well known in the art.

The pharmaceutical compositions can also be formulated so as to provide slow, extended, or controlled release of the active ingredient therein using, for example, hydroxypropylmethyl cellulose in varying proportions to provide the desired release profile, other polymer matrices, liposomes and/or microspheres. The pharmaceutical compositions can also optionally contain opacifying agents and may be of a composition that releases the active ingredient(s) only, or preferentially, in a certain portion of the gastrointestinal tract, optionally, in a delayed manner. Examples of embedding compositions include polymeric substances and waxes. The active ingredient can also be in micro-encapsulated form, if appropriate, with one or more pharmaceutically acceptable carriers, excipients, or diluents well known in the art (see, e.g., Remington and Remington's).

The pharmaceutical compositions can be sterilized by, for example, filtration through a bacteria-retaining filter, or by incorporating sterilizing agents in the form of sterile solid compositions which can be dissolved in sterile water, or some other sterile injectable medium immediately before use.

In embodiments, the pharmaceutical compositions are administered orally in a liquid form.

Liquid dosage forms for oral administration of an active ingredient include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. In addition to inert diluents, the liquid pharmaceutical compositions can include adjuvants such as wetting agents, emulsifying and suspending agents, sweetening, flavoring, coloring, perfuming and preservative agents, and the like.

Suspensions, in addition to the active ingredient(s) can contain suspending agents such as, but not limited to, ethoxylated isostearyl alcohols, polyoxyethylene sorbitol and sorbitan esters, microcrystalline cellulose, aluminum metahydroxide, bentonite, agar-agar and tragacanth, and mixtures thereof.

In embodiments, the pharmaceutical compositions are administered by non-oral means such as by topical application, transdermal application, injection, and the like. In related embodiments, the pharmaceutical compositions are administered parenterally by injection, infusion, or implantation (e.g., intravenous, intramuscular, intraarticular, subcutaneous, and the like).

Compositions for parenteral use can be presented in unit dosage forms, e.g. in ampoules or in vials containing several doses, and in which a suitable preservative can be added. Such compositions can be in form of a solution, a suspension, an emulsion, an infusion device, a delivery device for implantation, or it can be presented as a dry powder to be reconstituted with water or another suitable vehicle before use. One or more co-vehicles, such as ethanol, can also be employed. Apart from the active ingredient(s), the compositions can contain suitable parenterally acceptable carriers and/or excipients or the active ingredient(s) can be incorporated into microspheres, microcapsules, nanoparticles, liposomes, or the like for controlled release. Furthermore, the compositions can also contain suspending, solubilising, stabilising, pH-adjusting agents, and/or dispersing agents.

The pharmaceutical compositions can be in the form of sterile injections. To prepare such a composition, the active ingredient is dissolved or suspended in a parenterally acceptable liquid vehicle. Exemplary vehicles and solvents include, but are not limited to, water, water adjusted to a suitable pH by addition of an appropriate amount of hydrochloric acid, sodium hydroxide or a suitable buffer, 1,3-butanediol, Ringer's solution and isotonic sodium chloride solution. The pharmaceutical composition can also contain one or more preservatives, for example, methyl, ethyl or n-propyl p-hydroxybenzoate. To improve solubility, a dissolution enhancing or solubilising agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in *Transdermal Drug Delivery: Developmental Issues and Research Initiatives* (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well known in the art, including transscrotal patches. Pharmaceutical compositions in such transdermal patches can contain one or more absorption enhancers or skin permeation enhancers well known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects.

Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, Transcutol®, and Azone®.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone.

In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as Silastic™, or other silicone rubbers. Matrix materials can be insoluble polypropylene, polyethylene, polyvinyl chloride, ethylvinyl acetate, polystyrene and polymethacrylate, as well as glycerol esters of the glycerol palmitostearate, glycerol stearate, and glycerol behenate type. Materials can be hydrophobic or hydrophilic polymers and optionally contain solubilising agents.

Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active ingredient is released through the rate controlling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the above-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Dosages

When the agents described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with viral infection and/or autoimmune disease.

Exemplary dose ranges include 0.01 mg to 250 mg per day, 0.01 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In embodiments, the agent is administered at a concentration of about 10 micrograms to about 100 mg per kilogram of body weight per day, about 0.1 to about 10 mg/kg per day, or about 1.0 mg to about 10 mg/kg of body weight per day.

In embodiments, the pharmaceutical composition comprises an agent in an amount ranging between 1 and 10 mg, such as 1, 2, 3, 4, 5, 6, 7, 8, 9, or 10 mg.

In embodiments, the therapeutically effective dosage produces a serum concentration of an agent of from about 0.1 ng/ml to about 50-100 μg/ml. The pharmaceutical compositions typically should provide a dosage of from about 0.001 mg to about 2000 mg of compound per kilogram of body weight per day. For example, dosages for systemic administration to a human patient can range from 1-10

µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In embodiments, about 50 nM to about 1 µM of an agent is administered to a subject. In related embodiments, about 50-100 nM, 50-250 nM, 100-500 nM, 250-500 nM, 250-750 nM, 500-750 nM, 500 nM to 1 µM, or 750 nM to 1 µM of an agent is administered to a subject.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with viral infection or autoimmune disease) is observed in the treated subject, with minimal or acceptable toxic side effects. Applicable methods for determining an appropriate dose and dosing schedule for administration of a pharmaceutical composition of the present invention are described, for example, in *Goodman and Gilman's The Pharmacological Basis of Therapeutics*, Goodman et al., eds., 11th Edition, McGraw-Hill 2005, and *Remington: The Science and Practice of Pharmacy*, 20th and 21st Editions, Gennaro and University of the Sciences in Philadelphia, Eds., Lippencott Williams & Wilkins (2003 and 2005), each of which is hereby incorporated by reference.

Combination Therapies

The agents and pharmaceutical compositions described herein can also be administered in combination with another therapeutic molecule. The therapeutic molecule can be any compound used to treat viral infection, autoimmune disease, or symptoms thereof. Examples of such compounds include, but are not limited to, anti-viral agents, immunosuppressants, anti-inflammatories, and the like.

The RLR activator or inhibitor can be administered before, during, or after administration of the additional therapeutic agent. In embodiments, the c RLR activator or inhibitor is administered before the first administration of the additional therapeutic agent. In embodiments, the RLR activator or inhibitor is administered after the first administration of the additional therapeutic agent (e.g., 1, 2, 3, 4, 5, 6, 7, 8, 9, 10, 11, 12, 13, 14 days or more). In embodiments, the RLR activator or inhibitor is administered simultaneously with the first administration of the additional therapeutic agent.

The amount of therapeutic agent administered to a subject can readily be determined by the attending physician or veterinarian. Generally, an efficacious or effective amount of an RLR activator or inhibitor and an additional therapeutic is determined by first administering a low dose of one or both active agents and then incrementally increasing the administered dose or dosages until a desired effect is observed (e.g., reduced symptoms associated with viral infection or autoimmune disease), with minimal or no toxic side effects. Applicable methods for determining an appropriate dose and dosing schedule for administration of a combination of the present invention are described, for example, in *Goodman and Gilman's The Pharmacological Basis of Therapeutics*, 11th Edition., supra, and in *Remington: The Science and Practice of Pharmacy*, 20th and 21st Editions, supra.

Kits

The invention provides for kits containing at least one novel RLR activator or inhibitor as described herein. The kits are suitable for use in preventing or treating viral infection and/or autoimmune disease. In embodiments, the RLR activator or inhibitor is provided as a pharmaceutical composition. In embodiments, the kit provides instructions for use. The instructions for use can pertain to any of the methods described herein.

Kits according to this aspect of the invention may comprise a carrier means, such as a box, carton, tube or the like, having in close confinement therein one or more container means, such as vials, tubes, ampules, bottles and the like. In embodiments, the kit provides a notice in the form prescribed by a governmental agency regulating the manufacture, use, or sale of pharmaceuticals or biological products, which notice reflects approval by the agency of manufacture, use or sale of the kit and the components therein for human administration.

EXAMPLES

It should be appreciated that the invention should not be construed to be limited to the examples that are now described; rather, the invention should be construed to include any and all applications provided herein and all equivalent variations within the skill of the ordinary artisan.

Example 1

Design of a Peptide-Based Inhibitor of RLR Signaling

The study of the innate immune responses to viral infection has been greatly advanced by the use of reverse genetic approaches to dissect virus-induced signaling pathways (Akira et al., *Cell* 124:783-801 (2006)). In mammalian cells, these approaches have led to the identification of the two primary antiviral response systems known as the Toll-like Receptor (TLR) family and the RIG-I like Receptor (RLR) family. Among these, RLRs are unique in that they function in all mammalian cells, and thus, provide the only known comprehensive immune-surveillance network operating to detect infections (Beutler et al., *Annu. Rev. Immunol.* 24:353-389 (2006)).

There are currently no known inhibitors that specifically target the RLR-mediated antiviral signaling pathways. In considering how to create a RLR-specific inhibitor, focus was directed to the earliest-acting regulators of signal transduction because it is at the receptor proximal level that the RLR regulators differ from their TLR counterparts (Beutler et al., *Annu. Rev. Immunol.* 24:353-389 (2006); and Nakhaei et al., *Semin. Immunol.* 21:215-222 (2009)). The only factors that are unique to the RLR pathways are the receptors themselves, RIG-I and MDA5, and the MAVS adaptor. Since MAVS is essential for both receptors, an inhibitor of MAVS is likely to provide a simple way of blocking all RLR signaling without affecting TLR-mediated signal transduction.

To design an inhibitor that targets MAVS, peptides were designed that corresponded to regions that are important for protein-protein interactions. MAVS alleles that contain a threonine to alanine mutation at position 54 exhibit a dominant negative phenotype (Seth et al., *Cell* 122:669-682

(2005)). This mutation is present within the CARD-like domain of MAVS, which is responsible for interactions with other CARD-containing proteins such as the RLRs themselves (Meylan et al., Nature 437:1167-1172 (2005)). Thus, a fusion peptide that consists of a 23 mer that overlaps with this region of MAVS and the cell penetrating domain of the Drosophila antennapedia protein was generated (FIG. 1).

As antennapedia-containing peptides rapidly enter the cytosol of any mammalian cell (Joliot, A., Sci. STKE 2005: pe54 (2005)), the generated fusion peptide is an inhibitor that is capable of entering the cytosol of any mammalian cell and has the potential of altering the RLR/MAVS signaling pathways that cause various human diseases.

Example 2

Figure 2:
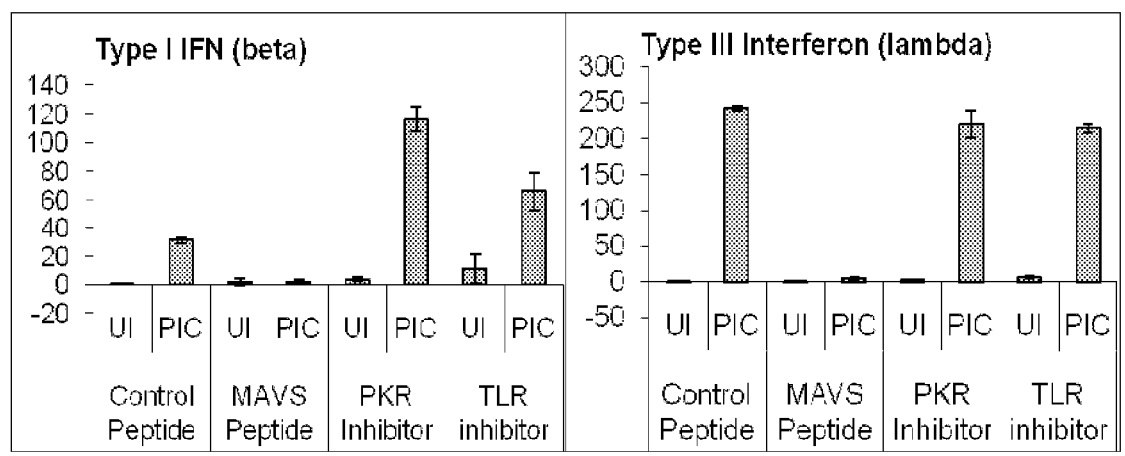
FIG. 2 includes graphs showing the inhibitory effects of the novel RLR/MAVS signaling inhibitor. The results are from T84 cells that were treated for 1 hr with the inhibitors shown and then treated with PolyIC (PIC) for 5 hours. Cytokine expression was then assessed by qPCR. The y-axis indicates fold induction over untreated cells (UI).

MAVS Peptide Inhibitor Specifically Blocks RLR-Induced Antiviral Signaling in Human Cells To determine if the MAVS peptide can block RLR signaling in human cells, experiments were performed in the human intestinal epithelial cell (IEC) line T84 comparing the peptide to a previously characterized antennapedia-peptide that targets the TLR adaptor MyD88. These cells were chosen because it is well-known that many viruses penetrate the intestinal epithelium and it has been shown that they respond naturally to both TLR and RLR ligands (FIG. 2 and data not shown). Polarized T84 cells were pretreated for 1 hour with each peptide and then treated for 5 hours with synthetic viral RNA PolyIC, which activates signaling by both RLRs. Quantitative RT-PCR analysis showed that PolyIC activated the expression of the Type I IFN (IFNβ) and Type III IFN IL-29, also known as IFN lambda (FIG. 2). Interestingly, the MAVS peptide completely abolished the expression of both IFNs in response to PolyIC. This inhibitory affect was specific, as the IFN expression was unaffected in cells treated with control peptides. Moreover, neither chloroquine (which blocks TLRs that detect viral RNA) nor inhibitors of the dsRNA dependent kinase PKR, affected polyIC-induced IFN expression. These results indicate that the RLR/MAVS pathway is primarily responsible for PolyIC induced IFN expression. Similar results were obtained when examining PolyIC-induced IFN expression in 293T human kidney cells, indicating that the inhibitory effects of the MAVS peptides are not restricted to T84 cells (not shown).

Figure 3:
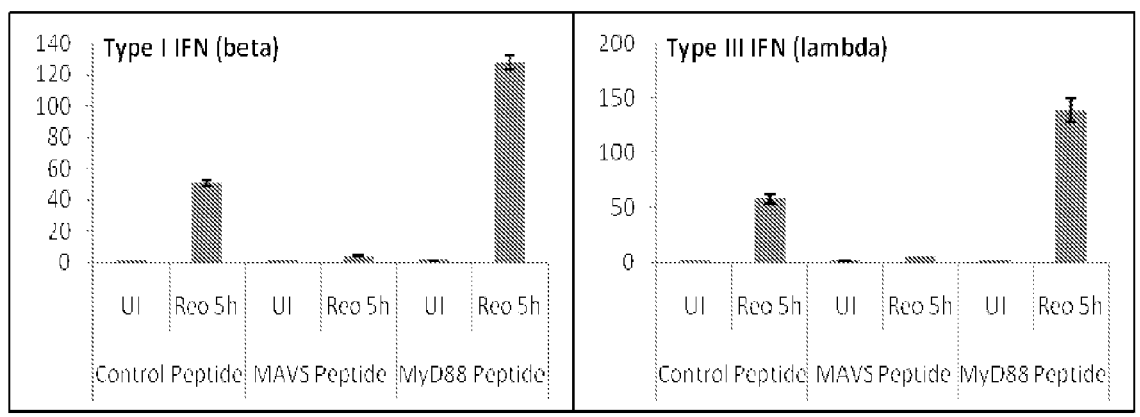
FIG. 3 includes graphs showing anti-viral effects of the novel RLR/MAVS signaling inhibitor. The results are from T84 cells that were pretreated for 1 hr with the inhibitors shown and infected with reovirus for 5 hours. Expression of the cytokines shown was assessed by qPCR. The y-axis indicates induction fold over untreated cells (UI).

Finally, to determine if the MAVS inhibitor could prevent RLR-mediated responses to an actual virus, Type III Dearing Strain of mammalian reovirus, which naturally infects human intestinal epithelial cells (Neutra, M. R., J. Infect. Dis. 179 Suppl 3:S441-443 (1999)), were utilized. Reovirus-induced Type I and Type III IFN expression was prevented by MAVS inhibitors, but not MyD88 inhibitors (FIG. 3). Collectively, these data demonstrate the potency of the MAVS peptide inhibitor, and indicates the importance of the RLR/MAVS pathway (as opposed to the TLR/MyD88) pathway in regulating antiviral responses in human cells.

Accordingly, described herein is a cell-permeable peptide inhibitor of antiviral pathways that operates in every human cell. It consists of the cell penetrating domain of the Drosophila antennapedia protein and amino acids 50-73 of the human MAVS protein. This peptide blocks antiviral responses in human cells at micromolar concentrations, and the responses blocked include the expression of Type I and III interferons and various interferon stimulated genes, including viperin. This peptide represents the first described means of blocking antiviral responses in human cells before or at any time after infection by a virus. Moreover, this molecule can serve as a therapeutic to treat inflammatory autoimmune diseases (e.g., those that are caused by inappropriate activation of antiviral responses). No other method currently exists to accomplish these goals.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents and publications mentioned in this specification are herein incorporated by reference to the same extent as if each independent patent and publication was specifically and individually indicated to be incorporated by reference.

What is claimed is:

1. An inhibitor of antiviral RIG-I like receptors (RLRs) activity comprising a polypeptide fragment of SEQ ID NO: 4, wherein the polypeptide fragment of SEQ ID NO: 4 is a fragment selected from the group consisting of residues 10-77 of SEQ ID NO: 4, residues 15-77 of SEQ ID NO: 4, residues 20-77 of SEQ ID NO: 4, residues 25-77 of SEQ ID NO: 4, residues 30-77 of SEQ ID NO: 4, residues 35-77 of SEQ ID NO: 4, residues 40-77 of SEQ ID NO: 4, residues 45-77 of SEQ ID NO: 4, residues 50-77 of SEQ ID NO: 4, residues 10-73 of SEQ ID NO: 4, residues 15-73 of SEQ ID NO: 4, residues 20-73 of SEQ ID NO: 4, residues 25-73 of SEQ ID NO: 4, residues 30-73 of SEQ ID NO: 4, residues 35-73 of SEQ ID NO: 4, residues 40-73 of SEQ ID NO: 4, residues 45-73 of SEQ ID NO: 4 and residues 50-73 of SEQ ID NO: 4, and a covalently linked moiety that facilitates delivery of the inhibitor to the cytosol of a cell.

2. The inhibitor of claim 1, wherein the polypeptide fragment consists of SEQ ID NO: 1 (GNRDTLWHLFNTLQRRPGWVEYFI).

3. The inhibitor of claim 1, wherein the inhibitor further comprises amino acids from the medial proline-rich region of SEQ ID NO: 4 (amino acids 107-173) or the C-terminal transmembrane domain of SEQ ID NO: 4 (amino acids 514-535).

4. The inhibitor of claim 1, wherein the covalent linkage of the moiety is N-terminal to the polypeptide fragment.

5. The inhibitor of claim 1, wherein the covalent linkage of the moiety is C-terminal to the peptide fragment.

6. The inhibitor of claim 1, wherein the moiety comprises a cell penetrating domain of the *Drosophila* antennapedia protein.

7. The inhibitor of claim 6, wherein the cell penetrating domain comprises SEQ ID NO: 2 (RQIKIWFQNRRMKWKK).

8. The inhibitor of claim 1, wherein the inhibitor comprises SEQ ID NO: 3 (GNRDTLWHLFNTLQRRPGWVEYFIRQIKIWFQNRRMKWKK).

9. The inhibitor of claim 1, wherein the inhibitor further comprises a detectable moiety.

10. A pharmaceutical composition comprising an inhibitor of claim 1.

11. The pharmaceutical composition of claim 10, wherein the pharmaceutical composition comprises a pharmaceutically acceptable carrier, diluent, or excipient.

12. The pharmaceutical composition of claim 10, wherein the pharmaceutical composition further comprises a therapeutic agent.

13. The pharmaceutical composition of claim 12, wherein the therapeutic agent is an antiviral agent or an immunosuppressive agent.

14. An isolated polynucleotide encoding the inhibitor of claim 1.

15. An expression vector comprising the isolated polynucleotide of claim 14.

16. A host cell comprising the expression vector of claim 15.

17. A method of inhibiting RLR-induced signaling in a cell comprising contacting the cell with an inhibitor of claim 1, thereby inhibiting the MAVS adaptor protein in the cell.

18. A method of inhibiting RLR-induced signaling in a subject, wherein the method comprises administering to the subject an effective amount of an inhibitor of claim 1, thereby inhibiting the MAVS adaptor protein in the subject.

19. A method of treating a subject for a disease or disorder associated with an inappropriate host response to self RNA, wherein the method comprises administering an effective amount of an inhibitor of claim 1, thereby inhibiting RLR-induced signaling in the subject and treating the disease or disorder.

* * * * *

SEQUENCE LISTING

```
<160> NUMBER OF SEQ ID NOS: 8

<210> SEQ ID NO 1
<211> LENGTH: 24
<212> TYPE: PRT
<213> ORGANISM: Homo sapiens

<400> SEQUENCE: 1

Gly Asn Arg Asp Thr Leu Trp His Leu Phe Asn Thr Leu Gln Arg Arg
1               5                   10                  15

Pro Gly Trp Val Glu Tyr Phe Ile
            20

<210> SEQ ID NO 2
<211> LENGTH: 16
```

<212> TYPE: PRT
<213> ORGANISM: Drosophila sp.

<400> SEQUENCE: 2

Arg Gln Ile Lys Ile Trp Phe Gln Asn Arg Met Lys Trp Lys Lys
1               5                   10                  15

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Asn Arg Asp Thr Leu Trp His Leu Phe Asn Thr Leu Gln Arg Arg
1               5                   10                  15

Pro Gly Trp Val Glu Tyr Phe Ile Arg Gln Ile Lys Ile Trp Phe Gln
                20                  25                  30

Asn Arg Arg Met Lys Trp Lys Lys
            35                  40

<210> SEQ ID NO 4
<211> LENGTH: 540
<212> TYPE: PRT
<213> ORGANISM: Homo sapiens

<400> SEQUENCE: 4

Met Pro Phe Ala Glu Asp Lys Thr Tyr Lys Tyr Ile Cys Arg Asn Phe
1               5                   10                  15

Ser Asn Phe Cys Asn Val Asp Val Val Glu Ile Leu Pro Tyr Leu Pro
                20                  25                  30

Cys Leu Thr Ala Arg Asp Gln Asp Arg Leu Arg Ala Thr Cys Thr Leu
            35                  40                  45

Ser Gly Asn Arg Asp Thr Leu Trp His Leu Phe Asn Thr Leu Gln Arg
    50                  55                  60

Arg Pro Gly Trp Val Glu Tyr Phe Ile Ala Ala Leu Arg Gly Cys Glu
65                  70                  75                  80

Leu Val Asp Leu Ala Asp Glu Val Ala Ser Val Tyr Gln Ser Tyr Gln
                85                  90                  95

Pro Arg Thr Ser Asp Arg Pro Pro Asp Pro Leu Glu Pro Pro Ser Leu
                100                 105                 110

Pro Ala Glu Arg Pro Gly Pro Pro Thr Pro Ala Ala Ala His Ser Ile
            115                 120                 125

Pro Tyr Asn Ser Cys Arg Glu Lys Glu Pro Ser Tyr Pro Met Pro Val
    130                 135                 140

Gln Glu Thr Gln Ala Pro Glu Ser Pro Gly Glu Asn Ser Glu Gln Ala
145                 150                 155                 160

Leu Gln Thr Leu Ser Pro Arg Ala Ile Pro Arg Asn Pro Asp Gly Gly
                165                 170                 175

Pro Leu Glu Ser Ser Ser Asp Leu Ala Ala Leu Ser Pro Leu Thr Ser
                180                 185                 190

Ser Gly His Gln Glu Gln Asp Thr Glu Leu Gly Ser Thr His Thr Ala
            195                 200                 205

Gly Ala Thr Ser Ser Leu Thr Pro Ser Arg Gly Pro Val Ser Pro Ser
    210                 215                 220

Val Ser Phe Gln Pro Leu Ala Arg Ser Thr Pro Arg Ala Ser Arg Leu

```
            225                 230                 235                 240
    Pro Gly Pro Thr Gly Ser Val Val Ser Thr Gly Thr Ser Phe Ser Ser
                    245                 250                 255

Ser Ser Pro Gly Leu Ala Ser Ala Gly Ala Ala Glu Gly Lys Gln Gly
                260                 265                 270

Ala Glu Ser Asp Gln Ala Glu Pro Ile Ile Cys Ser Ser Gly Ala Glu
            275                 280                 285

Ala Pro Ala Asn Ser Leu Pro Ser Lys Val Pro Thr Thr Leu Met Pro
        290                 295                 300

Val Asn Thr Val Ala Leu Lys Val Pro Ala Asn Pro Ala Ser Val Ser
    305                 310                 315                 320

Thr Val Pro Ser Lys Leu Pro Thr Ser Ser Lys Pro Pro Gly Ala Val
                    325                 330                 335

Pro Ser Asn Ala Leu Thr Asn Pro Ala Pro Ser Lys Leu Pro Ile Asn
                340                 345                 350

Ser Thr Arg Ala Gly Met Val Pro Ser Lys Val Pro Thr Ser Met Val
            355                 360                 365

Leu Thr Lys Val Ser Ala Ser Thr Val Pro Thr Asp Gly Ser Ser Arg
        370                 375                 380

Asn Glu Glu Thr Pro Ala Ala Pro Thr Pro Ala Gly Ala Thr Gly Gly
    385                 390                 395                 400

Ser Ser Ala Trp Leu Asp Ser Ser Glu Asn Arg Gly Leu Gly Ser
                    405                 410                 415

Glu Leu Ser Lys Pro Gly Val Leu Ala Ser Gln Val Asp Ser Pro Phe
                420                 425                 430

Ser Gly Cys Phe Glu Asp Leu Ala Ile Ser Ala Ser Thr Ser Leu Gly
            435                 440                 445

Met Gly Pro Cys His Gly Pro Glu Glu Asn Glu Tyr Lys Ser Glu Gly
        450                 455                 460

Thr Phe Gly Ile His Val Ala Glu Asn Pro Ser Ile Gln Leu Leu Glu
    465                 470                 475                 480

Gly Asn Pro Gly Pro Pro Ala Asp Pro Asp Gly Gly Pro Arg Pro Gln
                    485                 490                 495

Ala Asp Arg Lys Phe Gln Glu Arg Glu Val Pro Cys His Arg Pro Ser
                500                 505                 510

Pro Gly Ala Leu Trp Leu Gln Val Ala Val Thr Gly Val Leu Val Val
            515                 520                 525

Thr Leu Leu Val Val Leu Tyr Arg Arg Leu His
        530                 535                 540

<210> SEQ ID NO 5
<211> LENGTH: 540
<212> TYPE: PRT
<213> ORGANISM: Homo sapiens

<400> SEQUENCE: 5

Met Pro Phe Ala Glu Asp Lys Thr Tyr Lys Tyr Ile Cys Arg Asn Phe
    1               5                   10                  15

Ser Asn Phe Cys Asn Val Asp Val Val Glu Ile Leu Pro Tyr Leu Pro
                    20                  25                  30

Cys Leu Thr Ala Arg Asp Gln Asp Arg Leu Arg Ala Thr Cys Thr Leu
                35                  40                  45

Ser Gly Asn Arg Asp Thr Leu Trp His Leu Phe Asn Thr Leu Gln Arg
        50                  55                  60
```

```
Arg Pro Gly Trp Val Glu Tyr Phe Ile Ala Ala Leu Arg Gly Cys Glu
 65                  70                  75                  80

Leu Val Asp Leu Ala Asp Glu Val Ala Ser Val Tyr Gln Ser Tyr Gln
                 85                  90                  95

Pro Arg Thr Ser Asp Arg Pro Asp Pro Leu Glu Pro Pro Ser Leu
            100                 105                 110

Pro Ala Glu Arg Pro Gly Pro Thr Pro Ala Ala His Ser Ile
            115                 120                 125

Pro Tyr Asn Ser Cys Arg Glu Lys Glu Pro Ser Tyr Pro Met Pro Val
        130                 135                 140

Gln Glu Thr Gln Ala Pro Glu Ser Pro Gly Glu Asn Ser Glu Gln Ala
145                 150                 155                 160

Leu Gln Thr Leu Ser Pro Arg Ala Ile Pro Arg Asn Pro Asp Gly Gly
                165                 170                 175

Pro Leu Glu Ser Ser Ser Asp Leu Ala Ala Leu Ser Pro Leu Thr Ser
            180                 185                 190

Ser Gly His Gln Glu Gln Asp Thr Glu Leu Gly Ser Thr His Thr Ala
        195                 200                 205

Gly Ala Thr Ser Ser Leu Thr Pro Ser Arg Gly Pro Val Ser Pro Ser
210                 215                 220

Val Ser Phe Gln Pro Leu Ala Arg Ser Thr Pro Arg Ala Ser Arg Leu
225                 230                 235                 240

Pro Gly Pro Thr Gly Ser Val Val Ser Thr Gly Thr Ser Phe Ser Ser
                245                 250                 255

Ser Ser Pro Gly Leu Ala Ser Ala Gly Ala Ala Glu Gly Lys Gln Gly
            260                 265                 270

Ala Glu Ser Asp Gln Ala Glu Pro Ile Ile Cys Ser Ser Gly Ala Glu
        275                 280                 285

Ala Pro Ala Asn Ser Leu Pro Ser Lys Val Pro Thr Thr Leu Met Pro
        290                 295                 300

Val Asn Thr Val Ala Leu Lys Val Pro Ala Asn Pro Ala Ser Val Ser
305                 310                 315                 320

Thr Val Pro Ser Lys Leu Pro Thr Ser Ser Lys Pro Pro Gly Ala Val
                325                 330                 335

Pro Ser Asn Ala Leu Thr Asn Pro Ala Pro Ser Lys Leu Pro Ile Asn
            340                 345                 350

Ser Thr Arg Ala Gly Met Val Pro Ser Lys Val Pro Thr Ser Met Val
        355                 360                 365

Leu Thr Lys Val Ser Ala Ser Thr Val Pro Thr Asp Gly Ser Ser Arg
370                 375                 380

Asn Glu Glu Thr Pro Ala Ala Pro Thr Pro Ala Gly Ala Thr Gly Gly
385                 390                 395                 400

Ser Ser Ala Trp Leu Asp Ser Ser Glu Asn Arg Gly Leu Gly Ser
                405                 410                 415

Glu Leu Ser Lys Pro Gly Val Leu Ala Ser Gln Val Asp Ser Pro Phe
            420                 425                 430

Ser Gly Cys Phe Glu Asp Leu Ala Ile Ser Ala Ser Thr Ser Leu Gly
        435                 440                 445

Met Gly Pro Cys His Gly Pro Glu Glu Asn Glu Tyr Lys Ser Glu Gly
        450                 455                 460

Thr Phe Gly Ile His Val Ala Glu Asn Pro Ser Ile Gln Leu Leu Glu
465                 470                 475                 480

Gly Asn Pro Gly Pro Pro Ala Asp Pro Asp Gly Gly Pro Arg Pro Gln
```

```
                    485              490               495
Ala Asp Arg Lys Phe Gln Glu Arg Glu Val Pro Cys His Arg Pro Ser
                500             505             510

Pro Gly Ala Leu Trp Leu Gln Val Ala Val Thr Gly Val Leu Val Val
                515             520             525

Thr Leu Leu Val Val Leu Tyr Arg Arg Arg Leu His
                530             535             540

<210> SEQ ID NO 6
<211> LENGTH: 540
<212> TYPE: PRT
<213> ORGANISM: Homo sapiens

<400> SEQUENCE: 6

Met Pro Phe Ala Glu Asp Lys Thr Tyr Lys Tyr Ile Cys Arg Asn Phe
1               5                   10                  15

Ser Asn Phe Cys Asn Val Asp Val Val Glu Ile Leu Pro Tyr Leu Pro
                20                  25                  30

Cys Leu Thr Ala Arg Asp Gln Asp Arg Leu Arg Ala Thr Cys Thr Leu
            35                  40                  45

Ser Gly Asn Arg Asp Thr Leu Trp His Leu Phe Asn Thr Leu Gln Arg
        50                  55                  60

Arg Pro Gly Trp Val Glu Tyr Phe Ile Ala Ala Leu Arg Gly Cys Glu
65                  70                  75                  80

Leu Val Asp Leu Ala Asp Glu Val Ala Ser Val Tyr Gln Ser Tyr Gln
                85                  90                  95

Pro Arg Thr Ser Asp Arg Pro Pro Asp Pro Leu Glu Pro Ser Leu
            100                 105                 110

Pro Ala Glu Arg Pro Gly Pro Pro Thr Pro Ala Ala Ala His Ser Ile
            115                 120                 125

Pro Tyr Asn Ser Cys Arg Glu Lys Glu Pro Ser Tyr Pro Met Pro Val
        130                 135                 140

Gln Glu Thr Gln Ala Pro Glu Ser Pro Gly Glu Asn Ser Glu Gln Ala
145                 150                 155                 160

Leu Gln Thr Leu Ser Pro Arg Ala Ile Pro Arg Asn Pro Asp Gly Gly
                165                 170                 175

Pro Leu Glu Ser Ser Ser Asp Leu Ala Ala Leu Ser Pro Leu Thr Ser
            180                 185                 190

Ser Gly His Gln Glu Gln Asp Thr Glu Leu Gly Ser Thr His Thr Ala
        195                 200                 205

Gly Ala Thr Ser Ser Leu Thr Pro Ser Arg Gly Pro Val Ser Pro Ser
    210                 215                 220

Val Ser Phe Gln Pro Leu Ala Arg Ser Thr Pro Arg Ala Ser Arg Leu
225                 230                 235                 240

Pro Gly Pro Thr Gly Ser Val Val Ser Thr Gly Thr Ser Phe Ser Ser
                245                 250                 255

Ser Ser Pro Gly Leu Ala Ser Ala Gly Ala Ala Glu Gly Lys Gln Gly
            260                 265                 270

Ala Glu Ser Asp Gln Ala Glu Pro Ile Ile Cys Ser Ser Gly Ala Glu
        275                 280                 285

Ala Pro Ala Asn Ser Leu Pro Ser Lys Val Pro Thr Thr Leu Met Pro
    290                 295                 300

Val Asn Thr Val Ala Leu Lys Val Pro Ala Asn Pro Ala Ser Val Ser
305                 310                 315                 320
```

```
Thr Val Pro Ser Lys Leu Pro Thr Ser Ser Lys Pro Pro Gly Ala Val
            325                 330                 335

Pro Ser Asn Ala Leu Thr Asn Pro Ala Pro Ser Lys Leu Pro Ile Asn
            340                 345                 350

Ser Thr Arg Ala Gly Met Val Pro Ser Lys Val Pro Thr Ser Met Val
            355                 360                 365

Leu Thr Lys Val Ser Ala Ser Thr Val Pro Thr Asp Gly Ser Ser Arg
        370                 375                 380

Asn Glu Glu Thr Pro Ala Pro Thr Pro Ala Gly Ala Thr Gly Gly
385                 390                 395                 400

Ser Ser Ala Trp Leu Asp Ser Ser Glu Asn Arg Gly Leu Gly Ser
                405                 410                 415

Glu Leu Ser Lys Pro Gly Val Leu Ala Ser Gln Val Asp Ser Pro Phe
            420                 425                 430

Ser Gly Cys Phe Glu Asp Leu Ala Ile Ser Ala Ser Thr Ser Leu Gly
        435                 440                 445

Met Gly Pro Cys His Gly Pro Glu Glu Asn Glu Tyr Lys Ser Glu Gly
    450                 455                 460

Thr Phe Gly Ile His Val Ala Glu Asn Pro Ser Ile Gln Leu Leu Glu
465                 470                 475                 480

Gly Asn Pro Gly Pro Pro Ala Asp Pro Asp Gly Gly Pro Arg Pro Gln
                485                 490                 495

Ala Asp Arg Lys Phe Gln Glu Arg Glu Val Pro Cys His Arg Pro Ser
            500                 505                 510

Pro Gly Ala Leu Trp Leu Gln Val Ala Val Thr Gly Val Leu Val Val
            515                 520                 525

Thr Leu Leu Val Val Leu Tyr Arg Arg Arg Leu His
        530                 535                 540

<210> SEQ ID NO 7
<211> LENGTH: 29325
<212> TYPE: DNA
<213> ORGANISM: Homo sapiens

<400> SEQUENCE: 7
acatggccaa tggccgcgcg ctctgcccgc ccgcctcct cgctgcggga agggtcctgg      60
gccccgggcg gcggtcgcca ggtctcaggg ccggggtac ccgaggtaag atcgcttccc    120
gggcgttggg tcctttcggc tcagcacgca cggacgcctt tagggaaggt ggctgcagcg   180
gcaggacgga gtccgccggg acgccctggg tctggggtgc gcggggggcc caggagggga   240
caggacgcgc ggggatccgg aagagcgggc cctgtcgcaa gagtttcggg aacactgagg   300
gctccaggcg ccgcatccag catccgggga aaggggta ggtggcgctg gcgtctgct     360 caggctgggg gaaaggtagg gccagaaggg gacgggcagc ggccgctgac ctcctcctgc   420
cgcccgcggg cccagggtga cgctaaggtg gggccgagcc tcgaccgggt gcgcctagag   480
gtcgagtgct gccgccctcc gctgggtctg gacagttctc ggcggcgaca ccagctcaaa   540
acggcctccc cgccctccgc ggacctgggt cgcgcccagg aatccgatcc aaggctgtga   600
ggcctgtccc tttgggaagg gtgggtgttt atttccggga tgcactcaga gcctctggac   660
agtcaggtcg gaaactttgc tgtattggga acactctgtc acctacttcc ttctcagttg   720
ggaaggaagt gccaagaaaa catgaaacaa accaaaaaca cgaaaaaggg attctctgta   780
tggaagccgt gaagctcaa aaatatctag gaggacagcc agcgacctgg gacctgtggc    840
agccatgtga aagcagggtt aatgtctgga ctaaatgttg cttccaccta agtgcaccct   900
```

```
cagcctccct cccgccaagt gaccttgggt cctctttggg cttgaaggca ggtggctgtg      960
tgggtctcgc tgcagggggtc tctgtgccct gcaaggtgta tgaccagttg cagtgaggca    1020
gcaggttttg ggttcaaatc ctgtgctagc ctctggccag ctgtgcacct tggcaacact     1080
ttccctgtca cgggattggg gaaggattaa ctgaaagaac cttaggatgt gcctgtctac     1140
aatgggccct ccataaatgt gaacaaatgt gggcttcctt ccttttgtt tgggccacat      1200 catcccttcc cctccatctg tggctgaagc tggaatgcag aagagtgcct catctgactg     1260
ccttctggta cctggctgat gccatgagaa aggaaggaga aagggtctt ttttttttg       1320 aaatggagtc tcactctctt gcccaggctg gagcgcagtg gtccaatctt ggctcactgc     1380
aacctctgcc tcctgggtct agagattctc ctgcctcagc ctcctgagta gctgggacta     1440
caggtgtgtg ccaccatgcc tggctaattt ttgcatttttt agtagagacg gggtttcacc    1500
atgttggcca ggctggtctc aaactcctga cctcaagtga tctgcctgcc tcggcctccc    1560
aaagtgctgg gattccaggc gtgagccacc gcgcccggcc gagaaaggga tctattaact    1620
cccatagagt tgttctttgc taatttcttg aaggctcaga ggaccccgc ctcaccttcc      1680 tgattctcct gacctgtcat tagtacttgc cccacgagga atgtagcagg gcctgctggc    1740
tggcaaagca actcatgcat gtgaggctct gaggccagtg acaggactgc ttcccctgtg    1800
aggaaggtct ggtggcccaa cagcttttag gtgctgtctg ctctacagca ctgcctcctg     1860
agagaggtct catgcctgcc tgatgcccac ttggtcctct cctgcctcct tccctccctg    1920
acaacccact tggaatccaa tagcatctca aacttcactt gttccgaact gagttctgga   1980
gtcccttctg agccactgct cctcccctgg cttctctggc ctggtaaaag ggcaccttcc    2040
atccacccag tgcccaagga gtcatgcttc ttttctctcc cttatctcct acaccctcaa    2100
aacaccagga atctggctgc ctcctgccat ctctgtggtt cccatcctga ccatagtcat    2160
cctgtctcct gggctgtggc ctccttactg gtctcccagt tttcatcctg gcccctccaa    2220
agtcctcaca accaccagag aagtctttaa tgtaaatcag atcctcttct ttccctgccg    2280
gaaccttcca gtggttccct gtttcactcc aactaaaacc cagagtcctt tcctacagca    2340
ctctacatga gtggcccctg ccacctcctt gaccttgaca atctctgccc cttttccctag   2400 cttgcttgct ttttttttttt ttttccctat gatggagttt tgatcttgtc acccaggctg    2460
gagtgcaatg gatgatttc agctcactgc aacctctgcc tcctgggttc aagcgattct      2520
cctgcctcag cctcccgagt agctgggatt acaggcgccc accaccatgc taattttgt      2580 attttagta gagaaagggt ttcaccatgt tggcgaggct ggtctcaacc tcctgagctc      2640
aggtgatcca cccgcctagg cctcccaaag tgctgggatt ataggcgtga gtcacgcagc    2700
cagccatccc tagctttctt gacctagacc acactgacct gctttctatt cttcaaacat     2760
gccaagctca ttcttgtttt aggacttttg catttaccat gctctctgcc taaaacacca   2820
atcttctcag agcctgagaa cagctcagct gtgttctgca cgctagttca gaaaggcttc    2880
tttgaccccc tagttcaagt agcatgcctg tctccagggg ctctgtctca ttacctgctt    2940
tactttcttt agagccttta ttgctatctg gaactcttat ttgggtatta atttactgat     3000
ctgttatttg tcccacccca ttagaatata aattggatgt ggcatagacc ttgtctcttt    3060
tattccctgc agcactccct gatggggggcg gcagaaaagt aacgagcaaa tacatctata   3120
actgcaaatt gtggtaactc ctacataaac aactggcagc aattgcttat atttgaggca    3180
cttaaaaatt tttaagctgg ctgggcgcgg tggctcatgc ctgtaatccc agcactttgg     3240
```

```
gaggccgagg cgggcagatc acgaggtcag gagatcgaga ccatcctggc taacacggtg   3300
aaacctgtct ctactaaaaa tacaaaaaat tagccgagcg tggtagcagg cgcctgtagt   3360
cccagctact tgggaggctg aggcaggaga atggtgtgaa cccggaggc ggagcttgca    3420
gtgagccgag attgcaccac tgcactccag cctgggtgaa ggagcgagac tgtctcaaaa   3480
aaaaaaaaaa aaaaaaaaa agaaatttttt ttaagctgct gggcgcggtg gctcacgcct   3540
gtaaatctca gcactttggg aggccgaggt gagcggatca cctgaggtcg ggagttcgag   3600
accggaacat ggtgaaaccc tgtctctact aaaaatacaa aattagcggg gcgtggtggc   3660
tcatgcctgt aatcccagct acttgggagg ctgaggcagg agaatcgctt gaacccagga   3720
ggcagaggtt gcagtgagcc gagatcgcgc cattgtactc cagcctgggc aaaaagagtg   3780
aactccattt caaaaaaaaa aaaaaaggcc aggcgcagtg gctcacgcct gtaatcccag   3840
cactttggga ggccgaggca ggcggatcac gagttcagga gattgagacc atcctggcta   3900
acacggtgaa accctatctc tactaaaaat acaaaaaatt agccgggtgt ggtggcgggc   3960
gcctgtggtc ccagctactc gggaggctga ggcaggagaa tggtgtgaac ccaggaggtg   4020
gagcttgcag tgagccgaga ttgcaccaca gcactccagc tttggtgaca gagcgaaact   4080
ccgtctcaaa aaaaaaaaaa aaaaaattt aagcttagag gccggccaca gtggctcagc    4140
actgtgcagg ccaaggcaag aggatcactt gaggtcaaga gttcgagacc agcctggcca   4200
acatggtgaa accctgtctc tactaaaaaa tacaaaaatt ggccaggcgc gttggctggc   4260
gcctgtaatc ctagcaactt gggagaccaa ggcaggcaga tcacctgggg tcaggagttc   4320
aggaccggcc tggccaacat taaaacatat aaaaccccgt ctctactaaa aatataaaaa   4380
ttatccaggc atggtggcgt gtacccgtaa tcccagctac tcgggaggct gaggtaggag   4440
aattgcttaa acccgagaag cagaggttgc agtgaaccga gattacgcca ctgcactcca   4500
gcctgggcaa cagagcgaga ctctttctca aaaacaacaa caacaacaaa caaacaaatt   4560
agccaggcat gatggtgggc acgtgtaatc ccagctactc gggaggctga ggcaggagaa   4620
ttgcttgaat gtgggagatg gaggctgcag tgagccgaga tcacaccact gcactccagc   4680
ctgggcgaca gggagactct gtctcaaaaa aaaaaaaaa aaaaaagtt tataaggctg     4740
aattaccgta ctgtcaaaac aagctgctat ctgagccgtt ttaagggtga ggaagtctgg   4800
aaactgataa cttgcccagg acacacagtg agttcaaggc atggaactca gtctcctatc   4860
ttaagaatgt atgtgggccg ggcatggtgg ctcacgcctg taatcccagc gctttgggag   4920
gccaaggcag gcagatcatc tgaggtcagg agttcaagac cagcctgacc aacatggaga   4980
aaccctgtct ctactaaaaa tacaaaatta ccaggtgtg gtggtgcatg tctgtaattc     5040
cagctactca ggaggctgag gcagaagaat cacttgaacc cggaaggcag aggttgcgat   5100
gagccgagat tgtgccattg tactccagcc tgggcaacaa gagtctggaa ctctgtctca   5160
aaaagaaaa aaagaatgta tgtgtagcag gcttttttt ttttttttc ccccgagacg       5220
gaatctggct ctgtcgccca ggctggagtg cagtggcgca atcttggctc actgcaagct   5280
ccgcctccca ggttcacgcc attctcctgc ctcagcctcc cgagtagctg ggactacagg   5340
cacccgccag tacgccgggc taatttttg tattttagt agagacgggg tttcaccgtg      5400
ttagccagga tggtcttgat ctcctgacct cgtgatccac ccgcctcggc ctcccaaagt   5460
gctgggatta caggcgtgag ccaccgtgcc cggcctatgt gtagcaggct taatggtgg    5520
gcctgcagcc atgtcatgga aagaagctga cctgaagatc tcagttcttt cttcttctac    5580
taactagcaa gcatacctca gtttcttctt taaagcggga tgatccgatt attatcatgt   5640
```

-continued

```
tggggttcac ttttattt ttcagtgtgt cccaaagcag cagcacgttt aggtatagcc      5700
ctcttgctat cagcttgagg gccttagagc caggaaggga gccaggacat ttataggcac    5760
agaaactagg gtcacataca gatccccca ccgcatgtgc tagggtaca tgcagacctt     5820
cccagtgctg accaacctgc agagaagaaa tgggccctag gtattctgga tctgattctt   5880
tttggtcttc aattattt atttttattt ttttagagac agggtctcgc tgtgttgccc     5940
aggctggcct cgaacagctg ggctcaagcg atcctcctgc cctagcttct tgagtagctg   6000
gtggtcatca attcatttt agcaaattct gcagaatttt tttttttt tttttttg       6060
agacggagtc tcactctgcc gcccaggctg gagtgcagtg gcgtgatctc ggctcactac   6120
aacctccgcc tcttgggttc aagcaattct ctgtctcagc ttcctgaata gctgggactg   6180
caggcgcccg ccaccatgct tggctaattt ttttgtattt tcagtagaga cggggtttca   6240
ccatcttggc caagttggta ttgaactcct gacctcgtga tccatccgcc tcggcctccc   6300
aacgtgctgg ggtacaggc gtgagccacc gcgcccggt tctgcaggaa ttttggagag     6360
actcaggcag taataaaata ggatgtttac agaaattaaa gatggcggcc gggcgcggtg   6420
gctcacgcct gtaatcccag cactttggga ggccgaggcg ggcgcatcac gaggtcagta   6480
aatcgagacc atcctggcta accccgtgaa accccgtctc tactaaaata caaaaaaatt   6540
agccgggcgt ggtggcgggc gcctgtcgtc ccagctactc aggaggctga ggcaggagaa   6600
tggcgtgaac ccgagaggcg gagcttgcag tgagccgaga tcgcgccacc gcactccagc   6660
ctgggcgaca gagaaagact ccgtctcaaa aaaaaaaaa agaaattaaa ggtggctgga   6720
cacattggct ggtgcttgtc atccgagcta cttgacaggc ggaggcaggg ggatcgcttg   6780
aggccaggcg tttgagacca gcctgggcag catcatgaga ccctgtctct agaaaaaata   6840
aaaaaattag ctgggcatag tggcgcaggt ttgtagttcc agctaccggg gatgctgagg   6900
cgggaggatt gcttgagccc acgagttcga ggctgcagtg aactattatt gcaccactgc   6960
acccaacttg ggtgacagag accccatctg tttgtttgtt tgttttgag acagagtttc    7020
gctcttgttg cccaggctgg agtgcaatgg tgcaatcttg gctcaccgca acctctgccc   7080
ccaggttcaa gcaattctcc tgcctcaacc tcccgagtag ctgggattac aggcatgcgc   7140
caccatgccc agctattttt tttttttttt tgtattttta gtagagacgg gattttctcc   7200
atgttggtca gtctggtctc caactcccga cctcagttaa tccccaaat tggcctccca    7260
aagtgctggg attataggcg tgaaccactg tgcccagccc gagacccat ctcttaaaaa   7320
caaaataaaa caaaacaaaa acggccaggt gtggtggctc acacctgtaa tccccaaact   7380
tgggaggccg aggcgggtgg accacttgag gtcaggagtc tgtgaccagc ttgccaacat   7440
ggtgaaaccc catctctact aaaaatacaa aaattagctg gcatggtgg tgcgcacctg   7500
taatcccagc tactcagaag ggaggctgag gcaagagact caattgaacc caggaggcgg   7560
aggttgcagt gagccgagat tgccccactg cactccagcc tgggtgacaa agtgagactc   7620
gctctcaaaa aaaaaaaaa gaagaaatta agatgaaag aaacaaaca ttccaaaaag    7680
ttgagaaaga attgccttt gtccagcccc actcccaacc ccccaaccct gttgtaatgt    7740
gtgatctgtt ttcttccagt ctcgtttcct ctcagtccat ccaccttca tggggccaga   7800
gccctctctc cagaatctga gcagcaatgc cgtttgctga agacaagacc tataagtata   7860
tctgccgcaa tttcagcaat ttttgcaatg tggatgttgt agagattctg ccttacctgc   7920
cctgcctcac agcaagagac caggtgagca agggaagtga cagcccgaca ctggcctggg   7980
```

```
ggcagggctg tggaattcaa agctcagccc catcctagtt cctcacccaa gcctgggctg    8040
gctccttcct tcttcctctt gctgtgtctt gctccttgtc cttgctgctt ttctttttt     8100 tttttttttt tgagattgag tctcgttctg tcgccaggct ggagtgcagt ggcacgatct    8160
tggctcattg caacctccgc ctcctgggtt caagtgattc tcctgcctca gcctcctgag    8220
tagctgggat tacaggtgcg tgccaccacg cccagctaat ttttttgttt ttaatagaga    8280
cggggtttca ccatgttggc caggatggtc ttgatctctt gaccttgtga tccgcctgcc    8340
tcggcctccc aaagtgctgg gattacaggc gtgagccacc gcaccctttgc tgcttttcta   8400 acttttggat ggagtgtggc tcagggtggc gttgctgact tcgccgagct ccccttgtg    8460 ttgcttttgt gcactgctca aaaatatggc gctggctctc tgagatttcc tggctctggt   8520
ccacttgccc actttttttg gaacctccta tttccttcat ctctcttgcc cttccttgtc    8580
ctgctcagtt ttgattccat tctccttgtc atggggccct gtcctggcac ggagctggga   8640
ctcaggtttg agagctggca ggatcagggt cgctctagcc ccaacagaac ttgctgcagg   8700
cccctggcac tcactagctg gtgaaacggg cacaacccct ccccgttgta gctgctgttc   8760
tcagattgga cccctgtgct ccagagggta cctgttggct cttttggggc ctcctgtcct   8820
cagatttctc aggagcccca ttgttgtctc cgctgtcctc ccacacagat cgcattagta   8880
tgcaggtctg tttggagttt gctcctccct cttgtatttt ggggtttata gggatatctt   8940
gttttatagt aaatattttc tgtgggtttt ctttattttc tttaaaaaat ttttttttga   9000
gacggagtct cgctgtgttg cccaggctgc agtgcaatgg catgatctca gctcactgca   9060
acctctgcct cctgggttca agtgattctc gcgcctcagc ctcctgagta gctgggtta    9120 caggcgcatg ccaccacacc tggctgattt tgtatttgta gtagagatgg agtttcacca   9180
tgttggccag gctggtcttt attttatt tttgagacaga gtcttgctct gtcactcagg    9240
ctggagtgca gtggcacgat tttttttttt ttttgagacg gagtctcact ctgtcgccca   9300
ggctggagtg cagtggtgtg atctcggctc actgcaagct ctgcctcctg ggttcacgcc   9360
attctcctgc ctcagcctct tgagtagatg ggactacagg cgcctgccac catgcccggc   9420 taatttttg tatttttaat agagacgggg tttcactgtg ttagccagga ttgtctcgat    9480
ctcctgacct catgatccac cgcctcggc ctcccaaagt gctgggatta caggcgtgag   9540
ccactgcgcc cagcattttt ttttttttt ttttgagat ggagtctcgc tgtgtcttcc     9600
aggctggagt tgcagtggtg ccatcttggg tcaacctctg cctcctgggt tcaagcaatt   9660
ctcctgcttc agcctcctga gtagctggga ttacaggtat atgctaccac acccggctaa   9720
tttttgtgtt tttagtagag acggactttc accatgttgg tcaggctggt cttgaactcc   9780
tgaccttgtg atcctcggcc ttccaaagtg ctgggattac gggtgtgagc taccgcacct   9840 ggctatttc cttttctaa aaatctagct cctgcaggat tctgtgggtt tttgtttctg     9900
ctgtctggtt gcttgttttt atgtgagaat tcaggtagac ataaaaactc tagggctggg   9960
cacggtggct cacgcctgta atcccagcgc tttgggaggc caaggcgggt ggatcacctg   10020
aggtcaggag ttcgagacca gcctggccaa catggcgaaa ccatgtctct actaaaaata   10080
caaaaaaatt agccgggtgt ggtggtgggc cctgtaatc ccagctactc gggaggctga    10140
ggcaggagaa tcgcttgaac tcaggaggca gaggttgcag taagctgata tcacggcact   10200
gcactccagc ctgggcgacg gagtgggact ccgtctgaaa aaaaaaaaa aaaagaaac     10260 aaaaaaactc tgcagccact gtcatctgcc cacaatctcc ccagcattct cagcttcctt   10320
gtttgttatt gtcggcccc tctctttccg tcttttgccc ctttcatcat acttttgcta    10380
```

```
tctacctttt ccttctctcc taatccaaac ctttcttttt gccctggggg ccatattaat   10440
ccaaggcttt tgtatcagat taactgggtt tggattcctg ccccactgtt ttaggatctt   10500
tgctacagta ctttgcttct gctaagcctc agtttcctca ttagtaaagt ggagataata   10560
atggcattaa ataaagatga tacatgcaaa gcccttaatg gagagcccag gacatagtta   10620
attgccagtt tccggcagct gcctttattg atgtggctgc taattgctct tcctcactcc   10680
atacctggcc ctgtcctggg ctccgatcca gtttcacgtg gctgccttgc ccttgtggct   10740
ttcttggcac ccctccccc gctgtggctt cattctgggt ggggaagtgg caggggccac    10800
ctggcttgag caggacagtg gcattgtgtc ttccaggatc gactgcgggc cacctgcaca   10860
ctctcaggga accgggacac cctctggcat ctcttcaata cccttcagcg gcggcccggc   10920
tgggtggagt acttcattgc ggcactgagg ggctgtgagc tagttgatct cgcggacgaa   10980
gtggcctctg tctaccagag ctaccagcct cgtgagcgtc ctgcccttgc cctcctggac   11040
ccccagcctg ctccctggcc tccgctctcc ttttctctct ccctgtactt cctgcctttc   11100
tctgtcatcc tctttcttgt cactgtgaag cgatgaataa acctgggtgt agatccaggc   11160
tgagccactt accagctgtg tccctttggc caagtccctt aatttccctg agcctcaggc   11220
ctctcttctg taaaatgaag ctcatggcag catctgccgc ggggagctgc agtgggtgat   11280
actgcgggac gatgcgtgtt gagtattgag ctgggctggg cacttcctgt atgcccagca   11340
catggagtct cccctaactt tcacggctgt agcattcgcc tcccacccct cctcatttct   11400
tctcccccac ctactcattc accctccctc tctcctcctt ctcttccct ccctggttt     11460 accctgagag ccttcgacgc cctctatcag ctgcccagtt attctttaag tccctctcag   11520
tgtccctgcc actctgagtg ctcggaggcg atttgatgag attgagtttg atcctgagtg   11580
agatcaagac atgggaggag gctgggcgcg gtgtttcaca cctgtaatcc cagcactttg   11640
ggaggccgag gcaggcggat catgaggtca ggagatggag accacctgg ctaaaacagt    11700 gaaaccccgt ctctactaaa aatacagaaa attagccggg catgttgtcc cagctactca   11760
ggaggccgag gcaggagaat cacttgaacc agggaggcag aggttgcagt gagctgagat   11820
cgcgccactg cactccagcc tgggcgacag agtgggattc catctcaaaa aaaaaaaaa    11880 aaagacatgg gaaaaaaat caagccagcc ctatttatat ttcaaactag aggtaacccc    11940
cgagaccctg gtcacattta tagctgtggg acatccatgt ttttcttttc tttctctctc   12000
tttttttttt ttcctttag agacagagtc ttgctgcgcc acccaggctg cagtgcagtg    12060
gtgcaatcat agctcactgc agccttgacc tcctggactc aagtgatcct tctacctcag   12120
cctccagagt agctgggact acaggcatgg acaactacac ctggctaatt tttaaattt    12180 ttgtagagat gacatctcac tatgttgccc aggctggtct caaactcctg ggctgaagcg   12240
atcggcctcc cagagtgctg ggatcatagg tgtgagccac cgcgtctggc tctcatgctt   12300
gcttttctct cctttttccc ttccttgctt ttcctccctc cctccctccc ttcctctctt   12360
ccttcctttt tttccttcct tcttttttaaa tatgtctctt catgtgtgga gattaatagt   12420
gatccctggc tgggcacggt ggctcacgcc tgtaatccca gcactttggg aggccgaggc   12480
gggcggatca caaggtcagg agttcgagac cagcctggcc aatatggtga aaccctgtct   12540
gtaccaaaaa tacaaaaaaa ttagctgcgc atggtggtgc aagcctgtaa tcccagctac   12600
ttgggaggct gaggcaggag aattgcttga accggggagg tggaggttgc agtgagccga   12660
gattgcgcca ctgcactcca gcctggatga cagagtgaga ctccgtctcc aaaaaaaaaa   12720
```

```
aacccaaaaa tagtgatccc ctgaatacaa tggctgtggt agggcctgat gagggggtggg   12780 ggcaaagggg aggggctcag gtggcagcat cagggcaggg gtcagtgagc aatgatagtc   12840
atgtggagga gaaagccact gggtcctagg atgcctgggg acagagaaga gtgactgctg   12900
acacggcgtg ggtgactaga gacccacgag gcccccccat actcccttc ctcccttgct    12960 accttgtcct ccatctgctc tcaccctccc actcctgccc ccttgccaag tgatgcttgt   13020
cactcctttt tttttttgaaa tggagtttcg ctctgtcgcc caggctggag tgcagtggtg   13080
ccatctcagc tcactgcaag ctccgcctcc cgggttcacg ccattctcct gcctcagcct   13140
cccgagtagc tgggactaca ggcgcctgca accatgcccg gctaactttt tgtattttt    13200 agtagagatg gggtttcacc gtgttagcca ggatggtctc gatctcctga cctcgtgatc   13260
cacccgcctc ggcctcccaa agtgctggga ttacaggcgt gagccaccaa gcccagccct   13320
gcttgtcact cttgaggagt gggcccacat cagaacagct tttggaccta tgggtggggc   13380
ggggggtgta cccaagagca cccaagcctc tttaatcatg aggagaaccc ccaattcctt   13440 ttttttgag acagagtctt gctcagtcgc ccaggctgga gtgcagtggc atgacttcgg   13500
ctcaccacaa cctctgcctc ccgggttcaa gtggttctcc ttcctcagcc tccctatagt   13560
ccctgattcc ttctattttt tttttttttt tttgagacgg agtctcgctc ttgttgccca   13620
ggctggagtg caatggtgca atctcaggtc atggcaacct tcacttccca ggttcaagca   13680
attctcctgc ctcagcctct cgagtagctg ggattacagg catgcgcctc cacgcctggc   13740
taattttgtt attttagta gagacagggt ttctccatgt tggtcaggct ggtctcgaac   13800
tcacgacctc aggtgatcca cccacttcgg cctcccaaag tgctgggatt acaggcgtga   13860
gccaccacgt ctggcttctt tttcttttt tccccgaga cggagtcttg ctctgttgcc    13920
caggctggag tgcagtggcg cgatctcagc tcactgcaac ctccgtctcc caggttcaag   13980
caattcttct gcctcagcct cctgagtagc tgggattaca ggtgcttgcc agcacgcctg   14040
gctaattttt gtattttag tagagacggg gtttcactat gttggccagg ctggtcttga    14100
actcctgacc tcctaatcca cctgccttgg cctccccaaa tcctgggatt acaggcatga   14160
gccatcgtgc ccagccctg attccttctt ttttttctt tctttttttt tttagacgga    14220
gtctcgctct gtcgcccagg ctggagtgca gtggcgcgat cttggcttac tgcaagctcc   14280
gcctcccggg ttcacgccat tctcctgcct cagcctcctg agtagctggg actacaggg    14340 cccgccacca tgcccggcta ataataatgt tgtatttta gtagagatgg ggtttcactg    14400
tgttagccag ggtggtctcg atctgacctc gtgatctgcc tgccttggcc tcccaaagtg   14460
ctgagattac aggcatgagc cactgtgccc agccctgatt ccttcttgat atcactacat   14520
ctttgtcctc tagggacctc ggaccgtccc ccagacccac tggagccacc gtcacttcct   14580
gctgagaggc cagggccccc cacacctgct gcggcccaca gcatccccta caacagctgc   14640
agagagaagg agccaagtta ccccatgcct gtccaggaga cccaggcgcc agagtccccca  14700 ggagaggtct gtcctcatag tctaccttga gccaccactt ttgtgttcct atctgcccac   14760
ttctgcccat tgagccttcc agaaaccctc tcccgtcccc tataaatcac gcctaatctc   14820
tgctcagaac cctagggctt cctcagtggg atctgcccc agaccagctt ccaggctgct    14880
gaccaggtct tcaccctgtg gcagccctaa tcctctgtca gcaaccagct gggagaccac   14940
agttttgtgt gtgtgtgtgt gtgtgtgtgt gacagtgtct cattctgtca cccaggctgg   15000
agtgcagtgg agtgatcttg gctcactgca acctctgcct cctgggttca ggtcattctc   15060
ctgcctcagc ctcctgagta gctgggatta caggcaccca ccaccacgcc cagctaattt   15120
```

```
ttgtattttt agtagagatg gggttttgcc gtgtcagcca ggctggtctc gaactcctga   15180
cctcaggtga tctgcccacc tttgcctccc aaagtgctgg gattacaggc gtgagccacc   15240
gcacctggca atgctgtgtg ttttctgtga ggtagacgta aggacacctg tggacagagg   15300
gtctgggaat taccagaacc caggcaaggg ctcccctggc tcctgtgctc catggtgtgg   15360
gctgaggcct ataggagatg ccccaagagc acaagctgcc ctttgtgagc tcttgggaga   15420
ggcaactgcc ttattcatat tttccctcat tgcagaattc agagcaagcc ctgcagacgc   15480
tcagccccag agccatccca aggaatccag atggtggccc cctggagtcc tcctctgacc   15540
tggcagccct cagccctctg acctccagcg ggcatcagga gcaggacaca gaactgggca   15600
gtacccacac agcaggtatg catggaatct ggaattatag ggtccttctg atctctcaag   15660
tgagggtaag aattagagtt gccccatctg gcttccttga acaggagaca aggtgggaat   15720
aaagggagtt caacccagga agcaaaccag ttccttagtg ggtgtatcag ttagcatttg   15780
ctgtgtaaca aatagtccac tccagttttc caaattttt ttttagtagc ttaaaataca    15840
gccatttatt tagcatatga tcctgtgggt caggcatttg ggctacctac atgggcattt   15900
cttctggtct tggctgaatt tcctctcaag tactcaccgg tatatacata agttctgcct   15960
ctggctgttt gctgagcacc ttggttctct tctatgtagt ctctcatcct ccagcacaca   16020
aacccatcat ggcagctggg cagagttctc agagagggct caaaactggc acagtgtccc   16080
ctgtgctcca ttctgtgggc aaaagcaagt tataaggcca gcctagattc aaggagtagg   16140
gaaatagact ccctccctag acgggaggac tgacaggcac agtgcagtgg ggctgggtgg   16200
agatgagcga gataagtagg gccattttg cgctctgcca aagggactgt agggaacagc    16260
cagggcctat agggcagtgg gagagggaca gtgaagggct gcatcagctg ttggcagggg   16320
aacctttagg cactgtctta ccgcagagat ctccagttcc cagtgaatca tgaaaacttc   16380
tcagtcccca gaggaagtaa ggtcttcatc atccagtggc ctggactcaa ctccagatgt   16440
cagtgctccc cctcagaaat atatagttgt ccatctggac ctctcaggcc agcatgtctc   16500
tttcctactt cccaaactat tccacatgac gctggtgccc agtcagccct cagtgccctg   16560
ggacagccac aagacacatg agcagttaga ggctgggaga cgtcatctta gtactttgt    16620 catccccaaa ctgctccaag cacctgtctg ctttgcagtg tcacctggcc acgggatgcc   16680
tttcaggagt tgctgtagac cacagaggca gagggcgctt aggtttcagt acgtttgtag   16740
acacaggtcc catgagattc tgtggtatta gattgtggtg ggggagctgt acatcagaat   16800 cacccctgact tttgccagct gtggggcttg gcatgtgcat tccgagttcc gtggagagtc   16860
ctgctgcaac tgcctttaca gaccatcacc acctgctatc ctctgcttcc cccacccagg   16920
tcaggcagcc tcccaggggt ggctttgtcc ttgtcccctc tcttcccaag cctccgggat   16980
ggccaggcct ctcggctggt gtgagctgtt ctgcatgagc catcctgcca ccccttgccc   17040
tgatccatgg ctgctcccac tcatggtggt aggagaggga cagcagtggg ggaagtgtcc   17100
aggattgcat gaggctaagg tcaaagtaga aaaggtagac acaggagagg ggaggtttcc   17160
caggtgggag aggaaaaagc ggagagaata attaataatg gtcttcaggc tcctaggtac   17220
catttcactg tgtgccagga cagacctggg gctacaggtc aaggactgag ggcagctgtt   17280
gggctttcag gccaggaagc agtgaccaaa gggactgtgg catctcctcc aagggcagga   17340
gatttggagg cctagacaca gtagggacca tgagatctgg gccagaggga cccttctcca   17400
ggcctcaagg taatggtctt tgggtctgtg tttccacttg tgttttttcca ccggcaggtg   17460
```

```
cgacctccag cctcacacca tcccgtgggc ctgtgtctcc atctgtctcc ttccagcccc   17520
tggcccgttc cacccccagg gcaagccgct tgcctggacc cacagggtca gttgtatcta   17580
ctggcacctc cttctcctcc tcatcccctg gcttggcctc tgcaggggct gcagagggta   17640
aacagggtgc agagagtgac caggccgagc ctatcatctg ctccagtggg gcagaggcac   17700
ctgccaactc tctgccctcc aaagtgccta ccaccttgat gcctgtgaac acagtggccc   17760
tgaaagtgcc tgccaaccca gcatctgtca gcacagtgcc ctccaagttg ccaactagct   17820
caaagccccc tggtgcagtg ccttctaatg cgctcaccaa tccagcacca tccaaattgc   17880
ccatcaactc aacccgtgct ggcatggtgc catccaaagt gcctactagc atggtgctca   17940
ccaaggtgtc tgccagcaca gtccccactg acgggagcag cagaaatgag gtgagtcctc   18000
gcccttcctg gcagggatcc tggccccttc ccccgggaca gcttgcccac ctggccctgg   18060
ccttggcccc ttcccagtct gcattctgtg tccagcctgt gctgctctgt ggcctctcct   18120
tgagggcata cagacagttg agaaccagcc tcatgcaggc cccacaccat gttctccagg   18180
aggaacagtc attgagcttc taagtctgga cacctcagga gggtcagcca caggggcac    18240 ccactggtca ggtgtataag ttcatttagg gctcgtagtt cctagtgaag ccgagcggtg   18300
ccgttttgca cataaggaag cagtgacggg gacagcacag tggcccatct gcctcttgcc   18360
ttgctcttca ccaggatgcc tggtgtgtcc ctccatggcc aggctttaca gaacgcagtc   18420
ccacctggag cagccactcg gacccagcag ccccccattg ttgcctgctc caagcctcac   18480
atctaaccct agctgcggct gtctgctggg aagagccaag tccatagggc cctttgggca   18540
catggccagg cctctgaccc tgtggctgct ctctagttct caggcccagg caggatgtca   18600
gtgcaggatg gagccccgcc ctaccaaagg cttccaggtg ggcatgagct cacaggcagg   18660
ccagggagta gggaaaggct gccctggagg aggccaccat tggtgcagat tcttggtccc   18720
ctctaccccc actgctccaa gaaaaggtgg cctaggggca ttatagattg ggaattgagg   18780
ggttggagtg ttagttcatg ccctggcctg gaatgggac cgcccctacca ggttcgtctc    18840 cctgccaacc ccagtccctt ccagtgctct cctttctttc ccaggagacc ccagcagctc   18900
caacacccgc cggcgccact ggaggcagct cagcctggct agacagcagc tctgagaata   18960
ggggccttgg gtcggagctg agtaagcctg gcgtgctggc atcccaggta gacagcccgt   19020
tctcgggctg cttcgaggat cttgccatca gtgccagcac ctccttgggc atggggccct   19080
gccatggccc agaggagaat gagtataagt ccgagggcac ctttgggatc cacgtggctg   19140
agaaccccag catccagctc ctggagggca accctgggcc acctgcggac ccggatggcg   19200
gccccaggcc acaagccgac cggaagttcc aggagaggga ggtgccatgc acaggccct    19260 cacctggggc tctgtggctc caggtggctg tgacaggggt gctggtagtc acactcctgg   19320
tggtgctgta ccggcggcgt ctgcactagt gaagccctgg gctcttccca ccacccatct   19380
gttccgttcc tgcagtacac ctggcccctc tccgaagccc cttgtccctt tcttggggat   19440
tgtggaggct gggtcagagg ggagttaagg gactgcaggc ctggcagcag gacatgcctt   19500
ggctgaacca agtcctgaga gcagcatctc tgtccccacg gtgccttgtg tgggtccccg   19560
tccttggctt tctgggtcct gggctgcccc cagtgctcca gaccttcccc actggcaatc   19620
caggttatca tccatgtcct ccagaggagc ttcctcctcc aggcctcagc cctgttggcc   19680
caggtggagc aggagggacc actgaacat gtggtgcttg gaatgcctc tcctgttgca     19740 ttggtccctg aaggcctcag ggcaggtatg tggtgtgtgg gcgactccac aagacctgcc   19800
tcccatcctg gcagcccagc ctgagaccgt tgcattgagg caggcaggag cggcagggtg   19860
```

```
gctgctctcc aggagcccaa ctgccttgag ttcctgcccc actgggcccc ctcccctgct   19920
gggcaatcct gggaaggtct ggaggttcct gtggacctca gggaagccag ggcagctgt    19980 caggcctgag gaagacctgt ggagctcctc tccagcctcc tctttccctc ccctctggtc   20040
tccattctct tcagctccct acatgggctg gggaggagac acctggtggg cagagctcag   20100
gcagaggttt ggatttcagc tccctcactt ccggggctgt gtggctttgg cagatgtcag   20160
acttctggtc ttgcttctcc acgtggacag tgagtatctg gctcattctt cactgggttc   20220
ttctgagatt gaacctacag gtgtttgcca agtgcctggc ccagagcaag tggccactgc   20280
ttctcccatc tctctcctgc ccaacctggt agagctgagg gcatgagagg cagagtgcac   20340
agtggtcaag ggtgcagctc tgcagcacag gcagcctagg cctgcgtccc aacctgcctc   20400
tcaccagctc tgtgacccctg gcaagggat ttatctgtct gtcccttagt tttctcacct   20460
gtaaaaggag gataagtata tatatatatt tcccagtgtt gtgaagatta aaggagttta   20520
tcgatgtagg tcttaggatg agtcctggca tttaccaagg gttggatata tgttattatc   20580
actattaagt gttgagggtc caggcatgct gggcaacagg gaccccatct ctacaaaaaa   20640
gtttaaaaaa ttagccaggc gtggtggtgc acctgtcgtc ttagctactt gggaggctga   20700
ggtgggagga tcacttgagc ccagaagctt gaagctgcag tgagctagga tcgtgccact   20760
gcactccaac ctgggtgaga gagcgagacc ctgtctcaag aaaagaaaa atgcagagaa   20820 acaggagtct tggctactcc tttagaggca gactcagacc ctcctgcctc acagctttat   20880
ctttgtattt gccccttact ttatcttgtg ccttgagaaa ttgctgggga gagaggtatg   20940
tccactgggc agctgtacag gatggaggat atagggcgtt tccactccca gcagccaggt   21000
tccctcaccc caagctcacc cactgttggg gagattatct acaataacac cagaaacaca   21060
ttggggtgga ttgggggtat ccttatgggt tcttttcagg gaaccattgc tggacaaggc   21120
acaggagcca cctccatttc tgagctctgc aagggacaag aactagagcc atcaggggct   21180
gggctcactg tggcccccacc ccaagccgtc agcctccagg gatctacacc ctgccttggc   21240
tgctacagct ttttcactcc actgcccctag gggagttcag caacctaatg atctctatct   21300
ctgaacatct cttcatccca tgctccaagt ccagcaacct gcaccctgga accaggagtg   21360
gaccctaccc gagctgtctg tattaatccc catcccccac caccaatctt aaaaagccct   21420
ctgtccccct accctaaacc ccagttaggt acccatgctg ggcaggtcag ttaacaattt   21480
atgcacaggt actagttta ttgtattacc gttccagggt agctttgaaa aaagtatctc   21540
aaaaaggcaa catgggccga gcgcagtggc tcacgcctgt aatcccagca ctttgggagg   21600
ccaaggtggg cagatcgcct gaggtctgga gttcaagacc agcctggcca cagggtgaa    21660 accccgtctc tacaaaaata agaaaattag ccaggtgtag tggcagacgt ctgtaatccc   21720
agctattcag gaggctgagg cacgagaatt ccatgaaccc aggatgcgga ggttgcagtg   21780
agccgagatt gtgccactgc gctccagcct gggcgacaga gtggtattct gtttcaaaaa   21840
aaaaaaaaaa ggcagtatgt agccccgaag actgttgccc aagtggtaga atgttagcac   21900
actaccagcc taggtaaaaa atacaaaaag taactgggca tggcggcgcc catctatagt   21960
cccagctaca tgggaggctg aggtgggaag ataagtcact tgagcccgcc aggaggcgga   22020
ggttgtagtg agctgagatc gcaccactgc actccagcct gggtgaccga gtgatactct   22080
gtctcaaaga aaaaaaatta aattttagc acagtaacca gccatgatgg gagatacccct   22140 gggtaaggca tgtagaaagg gttgagggac cttcccagtc ccctagcccc gcctcccatc   22200
```

```
ctcccatctt tttctttttt cttttttta gagaatcacc cagcctggag cgaagtggtg    22260
caatcataac tcactgtatc cttaaactcc cgggcttaag cgatcctcct gcctcagcct    22320
tctgagtaac taggacttca ggtacctgtc accatgcctg gctaattaaa ttttttttc    22380
tttttttttt ttgagatgga gtcttgctct gtcacccagg ctggagtgca gtggcgcgat    22440
ctcagctcac tgcgacctcc acctcctggg ttcaggccat tctcccgcct cagcctccag    22500
agtagctggg actacaggcg cctgccacca cgcctggcta atttttttgc acttttagta    22560
gagacggggt ttcactgtgt tagccaggat ggtctcgatc tcctgacctt gtgatccgcc    22620
cgcctcggcc tcccaaagtg ctgggattac aggcgtgagc caccgcgccc agccaaatta    22680
aattttttat agagatgagg tcatgctgtt atgttgccca ggttggcctc atgagatctt    22740
gccttagcct cccaaagtgc tgggattaca gatgtgagac actgcaccca aaccccacca    22800
cttttttttt tcctttttct tttttgaga cagtcttact ccgttgccca ggctggagtg    22860
tagtggcatg atctcagctc actgcaacct ccgcctcccg ggttcaagca attctcctgc    22920
ctcagcctcc cgagtagctg ggattacaga ggcctgccac cacacccgac taattttcgt    22980
attttttagta gagacggggt ttctccatgt tggccaggct gttcttgaac tcctgacctc    23040
aagtgctcca cctgcgttgg cttcccaaag tgctgggata caggagtgag ccactgcgcc    23100
tggctgatcc cagcactttt caaatgatgc cgctcaaagc cgtgacttgg cctactttga    23160
acagcaaact tgttgctgct gttgtcaacc tgaaggcctc tcaaatgcca gcttcaagca    23220
gggtgtgaat tggccagtgt cagatctcag gagtcctgtg ttgagagtgt ggctttcagc    23280
tgcggggagc tgcacttggt ggggaaagcc aggcaggtca ccctcacagc cagataatgt    23340
ggaggtcaga acccaaggaa gggagtgaga cctccactcc cagtggggga cctggccacc    23400
catccttggg gacctgagaa agcgtacttc accttgggt gaaggctggg tggggccaga    23460
gggaccagtg ccctcctcag tgcttagggg cagagccacc tgcagcaatg gtatctgcat    23520
attagcccct ctccaccttc tttctcccgc tgaatcattt ccctcaaagc ccaagagctg    23580
tcactgcttc tttctcctg ggaagaatgc gtggactctg cctggtgata gactgaagcc    23640
agaacagtgc cacaccctcg ccttaattcc ttgctaggtg ttctcagatt tatgagactt    23700
cttagtcaaa tatgagggag gttggatgtg gtggcttgtg cctgtaatcc cagcattttg    23760
ggaagccgag gtgggaggat cccttgaagc caggagtttg agacaagcct gggcaacaaa    23820
gcaagaccct atctctaaaa aaaaaaaaa aaaaaaaaa aaaaaaaaa aaaaaaaatc    23880
taggagatgc tctttacccct gcctggcctc aaactattaa tagcttcctt tgagcaacat    23940
tatttattat gaactttcaa acacaaaaaa gtagagagag tagaataaca aatccccatg    24000
agcccatcac ccaacttcag taattatcaa ttcatggcca tcttgttcac ccctgcctgc    24060
ttccctgctt cccctcattc tgcagaggtt cttttctttt gagacagagt gttgctctgt    24120
tgccaggct ggagtgcagt ggtgcaactt cggctcactg caacctccgc ctcccaggtt    24180
caagtgattc tcctgcttca gcctctcaag tagctgggat tacagatgcc cgccaccaca    24240
cctggctaat tttcgtattt ttgttagaga tggggtttca ccatgttggc caggctggtc    24300
tcgaactcct gacctcaagt gatccgcccg ccttggcctc ccaaaatgct gggattacag    24360
gtgtgaacca cggtgcctgg ccactgtaca ggttatttat agaagttgga gagtgaaggg    24420
ttgagaaagc caaggggcag atgcgggtct ggaggatttt gtgcctaagg ccctctcttt    24480
gctcccagac agcatgaagt aacaatgagg catccacctc ttggttttgt ggcctctgtg    24540
gatgacgtct ctcaccttga accagttcag agttggagta gcgcaggatc ctgtcttcag    24600
```

```
aggaggggcc gaagcgggtt cctctgttgt caagctcttt ggaggtgcct ggctgctact    24660
actgtcccag agaggtgatg atgaatgatg ggtgtgtcca gtggcagttt gccccactga    24720 ggcagggct tccactaggc cctgacagag cccttccagc aggcagaaat ccctgtgcta    24780
ggcaagattc aaactccgta gcatgtctcc tgctcccatc tcttaggaat ggagtccttc    24840
aggccttgag tcccacattt tccatgatgc tccattaagc agctgatagc accccacct    24900 ccagggaaag tgagttcaga gtccttggtc taatgcatct gtgttgaaat tgaggccttc    24960
ccctgtgttc acctttctgc tcttttttctt ttagcccaag gctatgaagg cctcattcgg    25020
tgctgggcat ggtcactcct agcattcctc actctgttgc taacagcaac agcaataata    25080
ataagggtta caacttactc catacctta c tgtctgccag gcattaagct aagtgcttta    25140
catatattaa gtcatttaat cctcataatg accctatgaa agagatacca tctcaaccca    25200
attgacagct ggtttgcaag attaggaggg atgaaggacc caggggacaa tgcgagggaa    25260
aactctgacc ccggggcccc aggctggatg ttctttatgc ctgtgaacca cagcttatca    25320
catgtctgga gttagggacc ccacttaaag tgagattttg gctggaggtg gtggatcata    25380
cctataatcc cagcactttg ggagaccaag gcagaaggac tgcttgaggc caggagttca    25440
aaaccagtgt aggtaacagc tagaccctat ctctacaaaa aatttaaaaa ttagctgggt    25500
gtggtggtat gtgcctcaag ttccagctac tcaggaggct gaggtgggag gatcacttga    25560
gcacaggagt ttgaagttac agtgagctat gatggcacca ctgcacttca gcctaggcaa    25620
cagagggaga ccctgtcttt aaagtacata gaggttttc acaccaacac atctctgccc    25680
agtgtgccaa catctgccac ctgctataat agtactataa cactcaatat gtaattaatg    25740
tagtctcagg gatgttatga caatatgatt acaactatca cgtgtgtgcc agccaggct    25800 caatgcccca ggctgggcga ggtggggcag gggacacagc ctaaaatgcc aggcctcagg    25860
aagccatttg gtttagcaga cattgtttat taaaggagtt acctatgcca gatcgaaggc    25920
ctaagatgat taagacacta tgagtgcctt caagtggttg gggacgttca tgattgtggt    25980
acagacaaat aggctttcac atcattcttt tatgtaatca tacaacagat atttgcacct    26040
acatgtgcag agcactgtga taggcctcag tgacacagaa taatacggca aagaccccac    26100
ccgatgagcc ccctcccacc acccaccagt acagtagggg gtggtttaat ggagtgttcc    26160
tggaatatga agtgggggca ggcattaggg gtggcaaagg acaagtgtt tatctgatca    26220 gttatgtact gtttataata agtaaatcag cagaggggga ataatactta gaacctatag    26280
agagtaaatc tgacaagatg aaatgctgat gaaaatatgg aggaaatgaa actctcatgg    26340
gttttgcagg gaatctaagt cagtgctgtg ttgtgaatgt aggtgtaccc tttgaattca    26400
tatgttgaat cctaaccccc aaagcaatgg cattaagagg tggggccttt ggggctgggt    26460
atggtggctc atgactgtaa tcccagcact ttgggatgct ggcaggggc agatcacttg    26520 aagccaggag tctgagatca gcctggccaa catggtgaaa ccccatctgt actaaaaata    26580
caaaaattag ccaggtgtga tggcgtacat ctgtaatttc agccactcgg gaggctgaga    26640
caggagaata gcttgaaccc agtaggtgga gatttcagtg agccgagatc gtgccactgc    26700
actccagcct gggtgacaga gcgagactcc atctcaaaaa ataataaag atgtggggcc    26760 tgtgggaggt ggttaggtca tgagggtgga gatcatgaat ggggttagca ccttataaaa    26820
caggcttgag ggagcccttc tgtccccttct accatgtgtg gatgcagtga gaaggcaccg    26880
tatctctgaa gcagagagcc cgccctggac actggatctg ctggcacctt gatcttggac    26940
```

```
ttcccagcct ctagaactgt gagaaataat tttttgttgt ttacaaatta cccaggctaa    27000
ggtgttctat tgtaacctga atggaccaag ctggtgtgac cctgttggaa aactggcagt    27060
atctaccaaa agccgaacat acgtataaac tgatccagca gttccactcc tgggtatgta    27120
caccacagaa agctatgtcc accgagacat tggcaagaat gtttctaacc acacgctgac    27180
tgtagcccca aacctgaaac aacccaaatg tccatccacc aacccaaatg tccatccaca    27240
gttgaagcta cagtgaagtc acagggtcga atactactgc acagcaacga atatgaatga    27300
aaatatcgct atgcacagca acatggataa atttcacaga catgaggtca agcaaaagag    27360
gtcagagtcc tcatcatcaa gagagaattc attgtatgat tctcttccta caaaaagtac    27420
agaaataagc aaaactgatc catggtgtta gaagccaggg aacagttaa caggggaggg     27480 atactgggga ggggcatcct ggagtgctgg tctacctcat ctgggtgttg atttcacgag    27540
tattgtcagt ttgtttccag actccctgtt ggagatgtgg aaataaaaac cacctaaaca    27600
agagcagaga ggccatttgg tcaaagtttg caaaggagtc agccatgatt gcttgtattt    27660 ggcagggtc aaaggcaggc agggactgtg aaatgttata gtgaaaaaa agggaaggct     27720 ctgggtgtgc tgtgattgga gattgttggc atggggacag agcggactaa ctggaggggc    27780
atctttggtt ggttgggggg gtatatttgg ctttctctgg ttggtctgga gttggaagag    27840
ggggtgtggt ggctggggat tgggaagaag ctggcagcca ctaagttcag actgttctgg    27900
gtccgattgc tgctgaggct gtggtttggc ttccttggct tcccaggctg gtcatgggtt    27960
tctggccaga gtctattgtc atatgtggcc tggccattgt ccagttgtat gttcagtctc    28020
ttggaaggaa gggtattgac tctgagaggg gccaccatcg ctggaatggg ggacacacag    28080
tacttcctcc agctgcctac acccccctag ggtcagtggc gcctgcctgt gagggtgagc    28140
ccaatggcta gagggctctg ctccaagtca ttgcttacta cacccacaaa cattcttcgt    28200
tctttaaggc ctaacttaaa gcccagatcc tacaggaaac cttgattaga ccctctctt     28260 tattaagctt cctaagatca aaccctgctt ttgtgtaaat gctgacctcc ttgcctacat    28320
tttaaaaacc tagagctggg catgatggcc ccagcctgta atcccagtga ttcaggagac    28380
tgaggtggga ggattgctag aagccaggag ttcgagacca gcctgggtaa catagctaga    28440
ccacatctct taaaataaaa tagttaattt agccaggcat gatgatatat gcctgtagtc    28500
ccaactactt ggaaggctga ggtgtgagga tcttgagcc cgggaggtcg aggctacagt      28560
aagctatgat ctcaccactg tactccagcc tgggtgacag agcgagaccc agactcaaaa    28620
aataaaaata aaaaccctga atatcttcct tctacttctt cagtgctgtt tttattaaa     28680 aaaaaaaaa accagccaaa accacaactt tttactgaag tgtaatgtaa atgctgtaaa     28740
aggcagtgaa aggcacaagg gaggtggagg ggtaggaagg gtggaagtgg cgggaggaag    28800
tggcagggca ggcaaaatga agggaagccc tgggttcttg tcctgcatcc gcagccagct    28860
cccactttcc tcaccctcca ggacctgtaa actgtgaggc tggaccagtt atgtcaaatc    28920
tgtcctcccc cagagctcag tccctctgcc cttgggtgtc cttggcacaa ggcaggctag    28980
gctgcaccag cttcctccat ctccgtcctg cctcccccat ccccaggtgc cattcccaca    29040
ccatctgaat cactgatttc ctcgcaatca gacgctatct tccagttaat cacttcgctt    29100
gtatttaaca taagaaagaa aaacccttc attatcacat acagctggaa atcggcttct     29160
tgcaggaggc gtatccaaag gaattggaga agagataaac tggtaattgg tgaaagaatt    29220
actttaattt ttttttcctac ttgctgtcat gatgatgtcc ttagaattgt gagcccgtgg   29280
acacttctgt acaataaatc tgctattatt acttctagaa ctaca                   29325
```

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5
```